US012624375B2

(12) United States Patent
Jewett et al.

(10) Patent No.: US 12,624,375 B2
(45) Date of Patent: *May 12, 2026

(54) METHODS FOR CO-ACTIVATING IN VITRO NON-STANDARD AMINO ACID (nsAA) INCORPORATION AND GLYCOSYLATION IN CRUDE CELL LYSATES

(71) Applicant: Northwestern University, Evanston, IL (US)

(72) Inventors: Michael Christopher Jewett, Evanston, IL (US); Jessica Carol Stark, Evanston, IL (US); Jasmine Hershewe, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/343,633

(22) Filed: Jun. 28, 2023

(65) Prior Publication Data

US 2024/0026411 A1     Jan. 25, 2024

Related U.S. Application Data

(63) Continuation of application No. 17/048,331, filed as application No. PCT/US2019/027733 on Apr. 16, 2019, now Pat. No. 11,725,224.

(60) Provisional application No. 62/658,181, filed on Apr. 16, 2018.

(51) Int. Cl.

| | |
|---|---|
| *C12P 21/00* | (2006.01) |
| *C12N 1/20* | (2026.01) |
| *C12N 9/00* | (2006.01) |
| *C12N 9/02* | (2006.01) |
| *C12N 9/10* | (2006.01) |
| *C12N 9/16* | (2006.01) |
| *C12N 9/88* | (2006.01) |

(52) U.S. Cl.
CPC .............. *C12P 21/005* (2013.01); *C12N 1/20* (2013.01); *C12N 9/0051* (2013.01); *C12N 9/1051* (2013.01); *C12N 9/16* (2013.01); *C12N 9/88* (2013.01); *C12N 9/93* (2013.01); *C12Y 108/01007* (2013.01); *C12Y 301/21001* (2013.01); *C12Y 402/01047* (2013.01)

(58) Field of Classification Search
CPC ....... C12P 21/005; C12N 1/20; C12N 9/0051; C12N 9/1051; C12N 9/16; C12N 9/88; C12N 9/93; C12Y 108/01007; C12Y 301/21001; C12Y 402/01047; C07K 14/245
See application file for complete search history.

(56) References Cited

U.S. PATENT DOCUMENTS

| | | | |
|---|---|---|---|
| 4,458,066 | A | 7/1984 | Caruthers et al. |
| 4,683,195 | A | 7/1987 | Mullis et al. |
| 4,683,202 | A | 7/1987 | Mullis |
| 5,478,730 | A | 12/1995 | Alakhov et al. |
| 5,494,810 | A | 2/1996 | Barany |
| 5,556,769 | A | 9/1996 | Wu et al. |
| 5,665,563 | A | 9/1997 | Beckler |
| 6,168,931 | B1 | 1/2001 | Swartz et al. |
| 6,518,058 | B1 | 2/2003 | Biryukov et al. |
| 6,548,276 | B2 | 4/2003 | Swartz |
| 6,783,957 | B1 | 8/2004 | Biryukov et al. |
| 6,869,774 | B2 | 3/2005 | Endo et al. |
| 6,994,986 | B2 | 2/2006 | Swartz et al. |
| 7,008,651 | B2 | 3/2006 | Ambuel |
| 7,118,883 | B2 | 10/2006 | Inoue et al. |
| 7,189,525 | B2 | 3/2007 | Deleersnijder |
| 7,189,528 | B2 | 3/2007 | Higashide et al. |
| 7,235,382 | B2 | 6/2007 | Endo |
| 7,273,615 | B2 | 9/2007 | Endo |
| 7,312,049 | B2 | 12/2007 | Calhoun |
| 7,338,789 | B2 | 3/2008 | Swartz et al. |
| 7,387,884 | B2 | 6/2008 | Suzuki et al. |
| 7,399,610 | B2 | 7/2008 | Shikata et al. |
| 7,776,535 | B2 | 8/2010 | Mehl |
| 7,817,794 | B2 | 10/2010 | Galvin |
| 8,298,759 | B2 | 10/2012 | Voloshin |
| 8,357,529 | B2 | 1/2013 | Swartz |
| 8,574,880 | B2 | 11/2013 | Bond |
| 8,703,471 | B2 | 4/2014 | Aebi |

(Continued)

FOREIGN PATENT DOCUMENTS

| | | |
|---|---|---|
| WO | 2003056914 | 7/2003 |
| WO | 2004013151 | 2/2004 |

(Continued)

OTHER PUBLICATIONS

Beaucage et al., "Deoxynucleoside phosphoramidites—a new class of key intermediates for deoxypolynucleotide synthesis." Tetrahedron letters 22.20 (1981): 1859-1862.

(Continued)

*Primary Examiner* — Iqbal H Chowdhury

(74) *Attorney, Agent, or Firm* — Quarles & Brady LLP

(57) ABSTRACT

Disclosed are methods, systems, components, and compositions for cell-free synthesis of proteins and glycoproteins. The methods, systems, components, and compositions may be utilized for incorporating non-standard amino acids (nsAAs) into cell-free synthesized proteins and glycosylating or otherwise modifying the cell-free synthesized proteins in vitro. The nsAAs of the cell-free synthesized protein may be modified via glycosylation or other modification.

20 Claims, 27 Drawing Sheets

Specification includes a Sequence Listing.

(56) References Cited

U.S. PATENT DOCUMENTS

| | | | |
|---|---|---|---|
| 8,715,958 B2 | 5/2014 | Goerke | |
| 8,734,856 B2 | 5/2014 | Endo | |
| 8,835,162 B2 | 9/2014 | Kwon | |
| 8,999,668 B2 | 4/2015 | Delisa | |
| 9,005,920 B2 | 4/2015 | Kusumegi | |
| 9,410,170 B2 | 8/2016 | Calhoun | |
| 9,528,137 B2 | 12/2016 | Jewett | |
| 9,951,392 B2 | 4/2018 | Jewett | |
| 10,017,728 B2 | 7/2018 | Jewett | |
| 10,118,950 B2 | 11/2018 | Jewett | |
| 10,457,932 B2 | 10/2019 | Jewett | |
| 10,465,221 B2 | 11/2019 | Jewett | |
| 10,577,632 B2 | 3/2020 | Jewett | |
| 10,590,456 B2 | 3/2020 | Jewett | |
| 10,829,795 B2 | 11/2020 | Jewett | |
| 11,725,224 B2 * | 8/2023 | Jewett | C12N 9/93 |
| | | | 435/69.1 |
| 2004/0209321 A1 | 10/2004 | Swartz et al. | |
| 2005/0170452 A1 | 8/2005 | Wildt | |
| 2006/0211085 A1 | 9/2006 | Bobrowicz | |
| 2006/0234345 A1 | 10/2006 | Schwartz et al. | |
| 2006/0252672 A1 | 11/2006 | Betenbaugh | |
| 2006/0257399 A1 | 11/2006 | Gerngross | |
| 2006/0286637 A1 | 12/2006 | Hamilton | |
| 2007/0026485 A1 | 2/2007 | Defrees | |
| 2007/0154983 A1 | 7/2007 | Calhoun et al. | |
| 2007/0178551 A1 | 8/2007 | Gerngross | |
| 2008/0138857 A1 | 6/2008 | Swartz et al. | |
| 2014/0045267 A1 | 2/2014 | Lajoie | |
| 2014/0255987 A1 | 9/2014 | Delisa | |
| 2014/0295492 A1 | 10/2014 | Jewett et al. | |
| 2014/0349353 A1 | 11/2014 | Nomura | |
| 2015/0259757 A1 | 9/2015 | Jewett | |
| 2016/0060301 A1 | 3/2016 | Jewett | |
| 2016/0083688 A1 | 3/2016 | Jewett | |
| 2016/0362708 A1 | 12/2016 | Jewett et al. | |
| 2017/0073381 A1 | 3/2017 | Jewett | |
| 2017/0306320 A1 | 10/2017 | Jewett | |
| 2017/0349928 A1 | 12/2017 | Jewett | |
| 2018/0016612 A1 | 1/2018 | Jewett | |
| 2018/0016614 A1 | 1/2018 | Jewett | |
| 2018/0298416 A1 | 10/2018 | Jewett | |
| 2019/0284600 A1 | 9/2019 | Jewett | |
| 2020/0270665 A1 | 8/2020 | Jewett | |

FOREIGN PATENT DOCUMENTS

| | | |
|---|---|---|
| WO | 2004035605 | 4/2004 |
| WO | 2006102652 | 9/2006 |
| WO | 2006119987 | 11/2006 |
| WO | 2007120932 | 10/2007 |
| WO | 2014144583 | 9/2014 |
| WO | 2015184283 | 12/2015 |
| WO | 2017117539 | 7/2017 |

OTHER PUBLICATIONS

Bremer, H. et al. *Escherichia coli* and *Salmonella*: Cellular and Molecular Biology. 2 edn, vol. 1 1553-1569 (ASM Press, 1996).
Brown et al., "[8] Chemical synthesis and cloning of a tyrosine tRNA gene." Methods in Enzymology. vol. 68. Academic Press, 1979. 109-151.
Bryant, J. A., et al. Chromosome position effects on gene expression in *Escherichia coli* K-12. Nucleic acids research 42, 11383-11392, (2014).
Bundy, B. C. et al. Site-specific incorporation of p-propargyloxyphenylalanine in a cell-free environment for direct protein-protein click conjugation. Bioconjugate chemistry 21, 255-263, (2010).
Calhoun, K.A. et al, An economical method for cell-free protein synthesis using glucose and nucleoside monophosphates. Biotechnol Prog, 2005. 21(4): p. 1146-53.

Calhoun, K.A. et al., Energizing cell-free protein synthesis with glucose metabolism. Biotechnol Bioeng, 2005. 90(5): p. 606-13.
Carlson, E. D., et al. Cell-free protein synthesis: applications come of age. Biotechnology advances 30, 1185-1194, (2012).
Caschera, F. et al. Synthesis of 2.3 mg/ml of protein with an all *Escherichia coli* cell-free transcription-translation system. Biochimie 99, 162-168, (2014).
Catherine, C. et al. Engineering Thermal Properties of Elastin-like Polypeptides by Incorporation of Unnatural Amino Acids in a Cell-free Protein Synthesis System. Biotechnology and Bioprocess Engineering 20, 417-422, (2015).
Chappell, J., et al. Validation of an entirely in vitro approach for rapid prototyping of DNA regulatory elements for synthetic biology. Nucleic acids research 41, 3471-3481, (2013).
Chauhan, J.S., et al, In silico platform for prediction of N-, O- and C-glycosites in eukaryotic protein sequences. PLoS One, 2013. 8(6): p. e67008.
Chen, Y. J. et al. Characterization of 582 natural and synthetic terminators and quantification of their design constraints. Nature methods 10, 659-664, (2013).
Darabedian, N., et al. "Optimization of chemoenzymatic mass tagging by Strain-Promoted cycloaddition (SPAAC) for the determination of O-GlcNAc stoichiometry by western blotting." Biochemistry 57.40 (2018): 5769-5774.
Datsenko, K. A. et al. One-step inactivation of chromosomal genes in *Escherichia coli* K-12 using PCR products. Proceedings of the National Academy of Sciences of the United States of America 97, 6640-6645, (2000).
Davanloo, P., et al. Cloning and expression of the gene for bacteriophage T7 RNA polymerase. Proceedings of the National Academy of Sciences of the United States of America 81, 2035-2039 (1984).
De Boer, H. A., et al. The tac promoter: a functional hybrid derived from the trp and lac promoters. Proceedings of the National Academy of Sciences of the United States of America 80, 21-25 (1983).
Des Soye, B. J., et al. Repurposing the translation apparatus for synthetic biology. Current opinion in chemical biology 28, 83-90, (2015).
Dumas, A. E., et al. Designing logical codon reassignment—Expanding the chemistry in biology. Chemical Science 6, 50-69 (2014).
Ellinger, T. et al. Single-step purification of T7 RNA polymerase with a 6-histidine tag. BioTechniques 24, 718-720 (1998).
Espah Borujeni, A., et al. Translation rate is controlled by coupled trade-offs between site accessibility, selective RNA unfolding and sliding at upstream standby sites. Nucleic acids research 42, 2646-2659, (2014).
Feldman, M.F., et al., Engineering N-linked protein glycosylation with diverse O antigen lipopolysaccharide structures in *Escherichia coli*. Proc Natl Acad Sci U S A, 2005. 102(8): p. 3016-21.
Fritz, B. R., et al. Implications of macromolecular crowding and reducing conditions for in vitro ribosome construction. Nucleic acids research 43, 4774-4784, (2015).
Gavel, Y. et al, Sequence differences between glycosylated and non-glycosylated Asn-X-Thr/Ser acceptor sites: implications for protein engineering. Protein Eng, 1990. 3(5): p. 433-42.
Glover, K.J., et al., In vitro assembly of the undecaprenylpyrophosphate-linked heptasaccharide for prokaryotic N-linked glycosylation. Proc Natl Acad Sci U S A, 2005. 102(40): p. 14255-9.
Glover, K.J., et al., Direct biochemical evidence for the utilization of UDP-bacillosamine by PglC, an essential glycosyl-1-phosphate transferase in the Campylobacter jejuni N-linked glycosylation pathway. Biochemistry, 2006. 45 (16): p. 5343-50.
Goodchild, "Conjugates of oligonucleotides and modified oligonucleotides: a review of their synthesis and properties." Bioconjugate Chemistry 1.3 (1990): 165-187.
Gottesman, S. Proteases and their targets in *Escherichia coli*. Annual review of genetics 30, 465-506, (1996).
Grodberg, J. et al. ompT encodes the *Escherichia coli* outer membrane protease that cleaves T7 RNA polymerase during purification. Journal of bacteriology 170, 1245-1253 (1988).

(56) References Cited

OTHER PUBLICATIONS

Guarino, C. et al, A prokaryote-based cell-free translation system that efficiently synthesizes glycoproteins. Glycobiology, 2012. 22(5): p. 596-601.

Heinzelman, P., et al. pH responsive granulocyte colony-stimulating factor variants with implications for treating Alzheimer's disease and other central nervous system disorders. Protein engineering, design & selection : PEDS 28, 481-489, (2015).

Hodgman, C.E. et al, Cell-free synthetic biology: thinking outside the cell. Metab Eng, 2012. 14(3): p. 261-9.

Hong, S. H. et al. Cell-free protein synthesis from a release factor 1 deficient *Escherichia coli* activates efficient and multiple site-specific nonstandard amino acid incorporation. ACS synthetic biology 3, 398-409, (2014).

Hong, S. H. et al. Improving Cell-Free Protein Synthesis through Genome Engineering of *Escherichia coli* Lacking Release Factor 1. Chembiochem : a European journal of chemical biology, (2015).

Hong, S. H., et al. Non-standard amino acid incorporation into proteins using *Escherichia coli* cell-free protein synthesis. Frontiers in chemistry 2, 34, (2014).

Horton, R. M. PCR-mediated recombination and mutagenesis. SOEing together tailor-made genes. Molecular biotechnology 3, 93-99, (1995).

Hwang, B. Y. et al. Substrate specificity of the *Escherichia coli* outer membrane protease OmpP. Journal of bacteriology 189, 522-530, (2007).

Ikeda, R. A. et al. Enzymatic properties of a proteolytically nicked RNA polymerase of bacteriophage T7. The Journal of biological chemistry 262, 3790-3799 (1987).

Ikeda, R. A. et al. Interactions of a proteolytically nicked RNA polymerase of bacteriophage T7 with its promoter. The Journal of biological chemistry 262, 3800-3808 (1987).

Inouye, S. et al. Up-promoter mutations in the lpp gene of *Escherichia coli*. Nucleic acids research 13, 3101-3110 (1985).

International Searching Authority. International Search Report and Written Opinion for application PCT/US2019/027733. Mailed on Aug. 8, 2019. 9 pages.

Jewett, M. C. et al. Mimicking the *Escherichia coli* cytoplasmic environment activates long-lived and efficient cell-free protein synthesis. Biotechnology and bioengineering 86, 19-26, (2004).

Karim, A. S. et al. A cell-free framework for rapid biosynthetic pathway prototyping and enzyme discovery. Metabolic engineering 36, 116-126, (2016).

Kwon, Y. C. et al. High-throughput preparation methods of crude extract for robust cell-free protein synthesis. Scientific reports 5, 8663, (2015).

Laine, R.A., The Information-Storing Potential of the Sugar Code. Glycosciences: Status and Perspectives, 1997: p. 1-14.

Lajoie, M. J. et al. Genomically recoded organisms expand biological functions. Science 342, 357-360, (2013).

Lederberg, J. et al. Replica plating and indirect selection of bacterial mutants. Journal of bacteriology 63, 399-406 (1952).

Li, J. et al. Cell-free protein synthesis enables high yielding synthesis of an active multicopper oxidase. Biotechnology journal 11, 212-218, (2016).

Lian, Q., et al, The cost-efficiency realization in the *Escherichia coli*-based cell-free protein synthesis systems. Appl Biochem Biotechnol, 2014. 174(7): p. 2351-67.

Linton, D., et al., Identification of N-acetylgalactosamine-containing glycoproteins PEB3 and CgpA in Campylobacter jejuni. Mol Microbiol, 2002. 43(2): p. 497-508.

Liu, C. C. et al. Adding new chemistries to the genetic code. Annual review of biochemistry 79, 413-444, (2010).

Marin, V. L., et al. "Functional assays of membrane-bound proteins with SAMDI-TOF mass spectrometry." Angewandte Chemie International Edition 46.46 (2007): 8796-8798.

Martemyanov, K. A., et al. Cell-free production of biologically active polypeptides: application to the synthesis of antibacterial peptide cecropin. Protein expression and purification 21, 456-461, (2001).

Maue, A.C., et al, A capsule conjugate vaccine approach to prevent diarrheal disease caused by Campylobacter jejuni. Hum Vaccin Immunother, 2014. 10(6): p. 1499-504.

Mbua, N. E., et al. "Strain-promoted alkyne-azide cycloadditions (SPAAC) reveal new features of glycoconjugate biosynthesis." Chembiochem: a European journal of chemical biology 12.12 (2011): 1912.

Mosberg, J. A., et al. Lambda red recombineering in *Escherichia coli* occurs through a fully single-stranded intermediate. Genetics 186, 791-799, (2010).

Muller, D. K., et al. Processivity of proteolytically modified forms of T7 RNA polymerase. Biochemistry 27, 5763-5771 (1988).

Narang et al., "[6] Improved phosphotriester method for the synthesis of gene fragments." Methods in Enzymology. vol. 68. Academic Press, 1979. 90-98.

Nehring, S., et al. Performance analysis of orthogonal pairs designed for an expanded eukaryotic genetic code. PloS one 7, e31992, (2012).

Ohtsubo, K. et al, Glycosylation in cellular mechanisms of health and disease. Cell, 2006. 126(5): p. 855-67.

Olivier, N.B., et al., In vitro biosynthesis of UDP-N, N'-diacetylbacillosamine by enzymes of the Campylobacter jejuni general protein glycosylation system. Biochemistry, 2006. 45(45): p. 13659-69.

Ollis, A.A., et al., Engineered oligosaccharyltransferases with greatly relaxed acceptor-site specificity. Nat Chem Biol, 2014. 10(10): p. 816-22.

Owczarzy et al., "Predicting stability of DNA duplexes in solutions containing magnesium and monovalent cations." Biochemistry 47.19 (2008): 5336-5353.

Perez, J. G., et al. "Cell-free synthetic biology: engineering beyond the cell." Cold Spring Harbor perspectives in biology 8.12 (2016): a023853.

Petrov, A. S. et al. RNA-magnesium-protein interactions in large ribosomal subunit. The journal of physical chemistry. B 116, 8113-8120, (2012).

Pochechueva, T., et al. "Tumor-associated glycans and their role in gynecological cancers: accelerating translational research by novel high-throughput approaches." Metabolites 2.4 (2012): 913-939.

Raman, R., et al., Glycomics: an integrated systems approach to structure-function relationships of glycans. Nat Methods, 2005. 2(11): p. 817-24.

Raucher, D. et al. Cell-penetrating peptides: strategies for anticancer treatment. Trends in molecular medicine 21, 560-570, (2015).

Renesto, P. et al. From genes to proteins: in vitro expression of rickettsial proteins. Annals of the New York Academy of Sciences 990, 642-652 (2003).

Salis, H. M., et al. Automated design of synthetic ribosome binding sites to control protein expression. Nature biotechnology 27, 946-950, (2009).

Santoro, S. W., et al. An efficient system for the evolution of aminoacyl-tRNA synthetase specificity. Nature biotechnology 20, 1044-1048, (2002).

Sheridan, C. "Commercial interest grows in glycan analysis." Nature biotechnology 25.2 (2007): 145-146.

Shin, J. et al. An *E. coli* cell-free expression toolbox: application to synthetic gene circuits and artificial cells. ACS synthetic biology 1, 29-41, (2012).

Shin, J. et al. Efficient cell-free expression with the endogenous *E. coli* RNA polymerase and sigma factor 70. Journal of biological engineering 4, 8, (2010).

Sousa, R. in Encyclopedia of Biological Chemistry vol. 4 (eds William J. Lennarz & M. Daniel Lane) (Elsevier, 2004).

Spiro, R.G., Protein glycosylation: nature, distribution, enzymatic formation, and disease implications of glycopeptide bonds. Glycobiology, 2002. 12(4): p. 43R-56R.

Stefano, J. E. et al. Lac UV5 transcription in vitro. Rate limitation subsequent to formation of an RNA polymerase-DNA complex. Biochemistry 18, 1063-1067 (1979).

Studier, F. W. et al. Use of bacteriophage T7 RNA polymerase to direct selective high-level expression of cloned genes. Journal of molecular biology 189, 113-130 (1986).

(56)       References Cited

OTHER PUBLICATIONS

Sullivan, C. J. et al. A cell-free expression and purification process for rapid production of protein biologics. Biotechnology journal 11, 238-248, (2016).

Swartz, J. R., et al. Cell-free protein synthesis with prokaryotic combined transcription-translation. Methods in molecular biology (Clifton, N.J.) 267, 169-182, (2004).

Szymanski, C.M., et al., Evidence for a system of general protein glycosylation in Campylobacter jejuni. Mol Microbiol, 1999. 32(5): p. 1022-30.

Takahashi, M. K. et al. Characterizing and prototyping genetic networks with cell-free transcription-translation reactions. Methods 86, 60-72, (2015).

Tunitskaya, V. L. et al. Structural-functional analysis of bacteriophage T7 RNA polymerase. Biochemistry. Biokhimiia 67, 1124-1135 (2002).

Valderrama-Rincon, J. D., et al. "An engineered eukaryotic protein glycosylation pathway in *Escherichia coli*." Nature chemical biology 8.5 (2012): 434-436.

Wacker et al., "N-linked glycosylation in Campylobacter jejuni and its functional transfer into *E. coli*," Science, Nov. 29, 2002; 298(5599):1790-3.

Wang, H. H. et al. Multiplexed genome engineering and genotyping methods applications for synthetic biology and metabolic engineering. Methods in enzymology 498, 409-426, (2011).

Wang, H. H. et al. Programming cells by multiplex genome engineering and accelerated evolution. Nature 460, 894-898, (2009).

Wang, L., et al. Addition of the keto functional group to the genetic code of *Escherichia coli*. Proceedings of the National Academy of Sciences of the United States of America 100, 56-61, (2003).

Wang, L.X. et al, Realizing the Promise of Chemical Glycobiology. Chem Sci, 2013. 4(9): p. 3381-3394.

Watanabe, M. et al. Cell-free protein synthesis for structure determination by X-ray crystallography. Methods in molecular biology 607, 149-160, (2010).

Weerapana, E. et al, Asparagine-linked protein glycosylation: from eukaryotic to prokaryotic systems. Glycobiology, 2006. 16(6): p. 91R-101R.

Wetmur, J. G. "DNA probes: applications of the principles of nucleic acid hybridization." Critical reviews in biochemistry and molecular biology 26.3-4 (1991): 227-259.

Wu, I. L. et al. Multiple site-selective insertions of noncanonical amino acids into sequence-repetitive polypeptides. Chembiochem : a European journal of chemical biology 14, 968-978, (2013).

Xu, Z., et al. High-level expression of soluble human beta-defensin-2 fused with green fluorescent protein in *Escherichia coli* cell-free system. Applied biochemistry and biotechnology 127, 53-62 (2005).

Yang, W. C. et al. Cell-free production of transducible transcription factors for nuclear reprogramming. Biotechnology and bioengineering 104, 1047-1058, (2009).

Young, T. S. et al. Beyond the canonical 20 amino acids: expanding the genetic lexicon. The Journal of biological chemistry 285, 11039-11044, (2010).

Young, T. S., et al. An enhanced system for unnatural amino acid mutagenesis in *E. coli*. Journal of molecular biology 395, 361-374, (2010).

Zawada, J. et al. Effects of growth rate on cell extract performance in cell-free protein synthesis. Biotechnology and bioengineering 94, 618-624, (2006).

Zawada, J. F. et al. Microscale to manufacturing scale-up of cell-free cytokine production—a new approach for shortening protein production development timelines. Biotechnology and bioengineering 108, 1570-1578, (2011).

Zhang, X. et al. "Applications of azide-based bioorthogonal click chemistry in glycobiology." Molecules 18.6 (2013): 7145-7159.

* cited by examiner

A

Campylobacter jejuni N-glycosylation

A hpd
*Non-typeable*
*Haemophilus*
*influenzae derived*
protein D

Diptheria toxoid
*Corynebacterium*
*diptheriae*

Tetanus toxoid
*Clostridium*
*tetani*

PorA
*Neisseria*
*meningitidis*
outer membrane
protein

A

A

A

B

A

B

*Cjwt LLO*

*Cleng LLO*

Echo optimization (ACH)

A

Average - Background

| [pAzF RS] (mg/mL) | 10 | 8 | 6 | 4 | 2 | 0 |
|---|---|---|---|---|---|---|
| 1 | 3396 | 3298 | 2942 | 3396 | 3568.5 | 1072 |
| 0.8 | 3382 | 3452.5 | 3236.5 | 3379 | 2314 | 889.5 |
| 0.6 | 3318.5 | 3480.5 | 2856 | 3486 | 3316.5 | 755.5 |
| 0.4 | 3327.5 | 3328 | 3392 | 3212.5 | 3396 | 531 |
| 0.2 | 3058.5 | 3010 | 3238 | 3324.5 | 3216 | 302 |
| 0 | 0 | 0 | 0 | 0 | 0 | 0 |

[pAzF] (mM)

% Background

| [pAzF RS] (mg/mL) | 10 | 8 | 6 | 4 | 2 |
|---|---|---|---|---|---|
| 1 | 0.315665 | 0.325045 | 0.364078 | 0.315465 | 0.300406 |
| 0.8 | 0.26301 | 0.257639 | 0.274834 | 0.263244 | 0.384399 |
| 0.6 | 0.227663 | 0.216445 | 0.264531 | 0.216724 | 0.22278 |
| 0.4 | 0.159579 | 0.159555 | 0.156545 | 0.165292 | 0.15636 |
| 0.2 | 0.098741 | 0.100332 | 0.093267 | 0.090841 | 0.093905 |

[pAzF] (mM)

METHODS FOR CO-ACTIVATING IN VITRO NON-STANDARD AMINO ACID (nsAA) INCORPORATION AND GLYCOSYLATION IN CRUDE CELL LYSATES

CROSS-REFERENCE TO RELATED PATENT APPLICATIONS

This application is a continuation of U.S. application Ser. No. 17/048,331, filed Oct. 16, 2020, which is the U.S. national stage entry of PCT/US2019/027733 filed Apr. 16, 2019, which claims the benefit of priority under 35 U.S.C. § 119(e) to U.S. Provisional Application No. 62/658,181, filed Apr. 16, 2018. The content of each of the aforementioned applications is incorporated herein by reference in its entirety.

STATEMENT REGARDING FEDERALLY SPONSORED RESEARCH OR DEVELOPMENT

This invention was made with government support under MCB1413563 awarded by the National Science Foundation. The government has certain rights in the invention.

REFERENCE TO AN ELECTRONIC SEQUENCE LISTING

The contents of the electronic sequence listing (702581_02369.xml; Size: 19,800 bytes; and Date of Creation: Jun. 28, 2023) is herein incorporated by reference in its entirety.

BACKGROUND

The field of the invention relates to in vitro synthesis of proteins. In particular, the field of the invention relates to one-pot systems for incorporating non-standard amino acids and glycosylation into cell-free synthesized proteins.

Cell-free protein synthesis (CFPS) using extracts from prokaryotic source strains such as E. coli has undergone a transformational shift from an exploratory platform used in the discovery of the genetic code to a present-day, high-yielding protein production platform [1]. This shift is fueled by the open nature of this system, allowing for rapid combination, supplementation, and optimization of the physiochemical environment for increasing protein yields and batch reaction duration [2, 3]. Now, cell-free systems are seen as a complement to in vivo protein expression and can be used as both a prototyping platform due to its simplicity, easiness, and modular design for protein expression [4-6] as well as a large-scale production platform for difficult to express proteins in vivo [7]. The transition from exploratory platform to high-yielding protein production platform has come about, at least in part, by complex strain engineering to stabilize biological substrates in the cell-free reaction mixtures [8, 9]. These genetic modifications targeted the deletion of proteins known to affect the stability of DNA [10], mRNA [8, 11], protein [12], energy [13], and amino acids [14, 15] in the cell-free reaction. In addition to strain engineering efforts, activation of multiple biological pathways [16], decreases in cost [17], and improved understanding of reaction contents makes CFPS an attractive platform for the production of new kinds of high-value proteins.

One area of great interest for the application of cell-free systems is the production of modified proteins containing non-standard amino acids. Incorporating non-standard amino acids or unnatural amino acids (nsAAs) allows for the production of proteins with novel structures and functions that are difficult or impossible to create using the 20 canonical amino acids [18, 19]. Recently, cell-free protein synthesis (CFPS) systems have been employed to increase yields of proteins bearing nsAAs [20, 21], achieve direct protein-protein conjugation [22], explore drug discovery [23], and enhance enzyme activity [24, 25].

Typically, nsAA incorporation systems use amber suppression technology to insert nsAAs into proteins, a method by which an in-frame amber (TAG) stop codon is utilized as a sense codon for assigning nsAAs [26, 27]. Amber suppression technology, however, has limited efficiency for nsAA incorporation because of the presence of release factor 1 (RF1). RF1 naturally binds the amber stop codon (TAG) [28] and prematurely terminates protein translation. Methods to counteract this competitive termination of the TAG stop codon include increasing the addition of competing tRNA [21], tagging and purifying out RFT [29], release factor engineering [30], and genomically recoding strains to remove RF1 and reassigning all occurrences to the synonymous TAA codon [31]. High-yield protein production with multiple-site incorporation of NSAAs still remains a critical challenge.

Glycosylation is possible in some CFPS systems. The development of a highly active E. coli CFPS platform has prompted recent efforts to enable glycoprotein production in E. coli lysates through the addition of orthogonal glycosylation components. In one study, Guarino and DeLisa demonstrated the ability to produce glycoproteins in E. coli CFPS by adding purified lipid-linked oligosaccharides (LLOs) and the C. jejuni OST to a CFPS reaction. Yields of between 50-100 µg/mL of AcrA, a C. jejuni glycoprotein, were achieved [64]. Despite these recent advances, bacterial cell-free glycosylation systems have been limited by their inability to co-activate efficient protein synthesis and glycosylation. We recently developed a cell-free glycoprotein synthesis (CFGpS) system that addresses this limitation by enabling modular, coordinated transcription, translation, and N-glycosylation of proteins in E. coli lysates selectively enriched with glycosylation enzymes (see WO 2017/117539, the content of which is incorporated herein by reference in its entirety). Here, we demonstrate in vitro incorporation of non-standard amino acids that include a chemical moiety for glycosylation or other post-translational modifications in crude cell lysates.

SUMMARY

Disclosed are methods, systems, components, and compositions for cell-free synthesis of proteins and glycoproteins. The methods, systems, components, and compositions may be utilized for incorporating non-standard amino acids (nsAAs) into cell-free synthesized proteins and glycosylating or otherwise modifying the cell-free synthesized proteins in vitro. The nsAAs of the cell-free synthesized protein may be modified via glycosylation or other modification.

In some embodiments, the methods, systems, components, and compositions relate to genomically recoded and engineered organisms. The disclosed genomically recoded and engineered organisms may be used to prepare extracts for platforms and methods for preparing sequence defined biopolymers, proteins, or glycoproteins in vitro. In particular, the methods, systems, components, and compositions relate to genomically recoded and engineered organisms comprising a strain which is genetically modified in a manner selected from: (i) modified to be deficient in release factor 1 (RF-1) or a genetic homolog thereof; (ii) modified to be deficient in one or more of endA and gor; (iii) modified to be deficient in one or more of gmd and waal; (iv) modified to produce glycosylation components such as lipid-linked oligosaccharides (LLOs), oligosaccharyltransferases (OSTs) or both of LLOs and OSTs; (v) modified to express an orthogonal translation system(s) (OTS) including one or more of orthogonal tRNA(s), engineered aminoacyl-tRNA synthetases(s) (aaRS), engineered elongation factors (EF), or any combination of the orthogonal tRNAs, the engineered aaRSs, and the engineered EFs.

In other embodiments, the methods, systems, components, and compositions relate to a platform for preparing a sequence defined biopolymer, protein, or glycoprotein in vitro, the platform comprising a cellular extract from the genomically recoded and engineered organisms disclosed herein. In certain embodiments, a cellular extract prepared from the strain of the genomically recoded and engineered organism is capable of preparing a sequence defined biopolymer, protein, or glycoprotein utilizing coupled in vitro translation/glycosylation in greater yield and/or purity than previously disclosed strains.

In some embodiments, the platform further comprises an orthogonal translation system component configured to incorporate unnatural, nonstandard, and/or non-canonical amino acids. Suitable unnatural, nonstandard, and/or non-canonical amino acids may include, but are not limited to, amino acids comprising a moiety that reacts and conjugates with a corresponding moiety on a carbohydrate monomer (e.g., a carbohydrate monomer of a glycan) such as p-azido-L-phenylalanine (pAzF) or p-proparglyoxy-L-phenylalanine (pAcF). In certain embodiments, the orthogonal translation system component is expressed from a plasmid present in the genomically recoded organism, expressed from an integration site in the genome of the genetically recoded organism, co-expressed from both a plasmid present in the genomically recoded organism and an integration site in the genome of the genetically recoded organism, expressed in an in vitro transcription and translation reaction, or added exogenously. In some embodiments, the cellular extract from the genomically recoded organism is a component in a reaction mixture.

In some embodiments, the sequence defined biopolymer, protein, or glycoprotein prepared from the disclosed platforms and methods includes at least one unnatural amino acid that is modified to include a chemical "handle" or "moiety" (e.g., such as an azido or proparglyoxyl handle or moiety), which provides an attachment point for a glycan via an oligosaccharyltransferase of via a chemical reaction with a glycan. In some embodiments, the sequence defined biopolymer or protein encodes a therapeutic product, a diagnostic product, a biomaterial product, an adhesive product, a biocomposite product, or an agricultural product.

DETAILED DESCRIPTION

Figure 1:
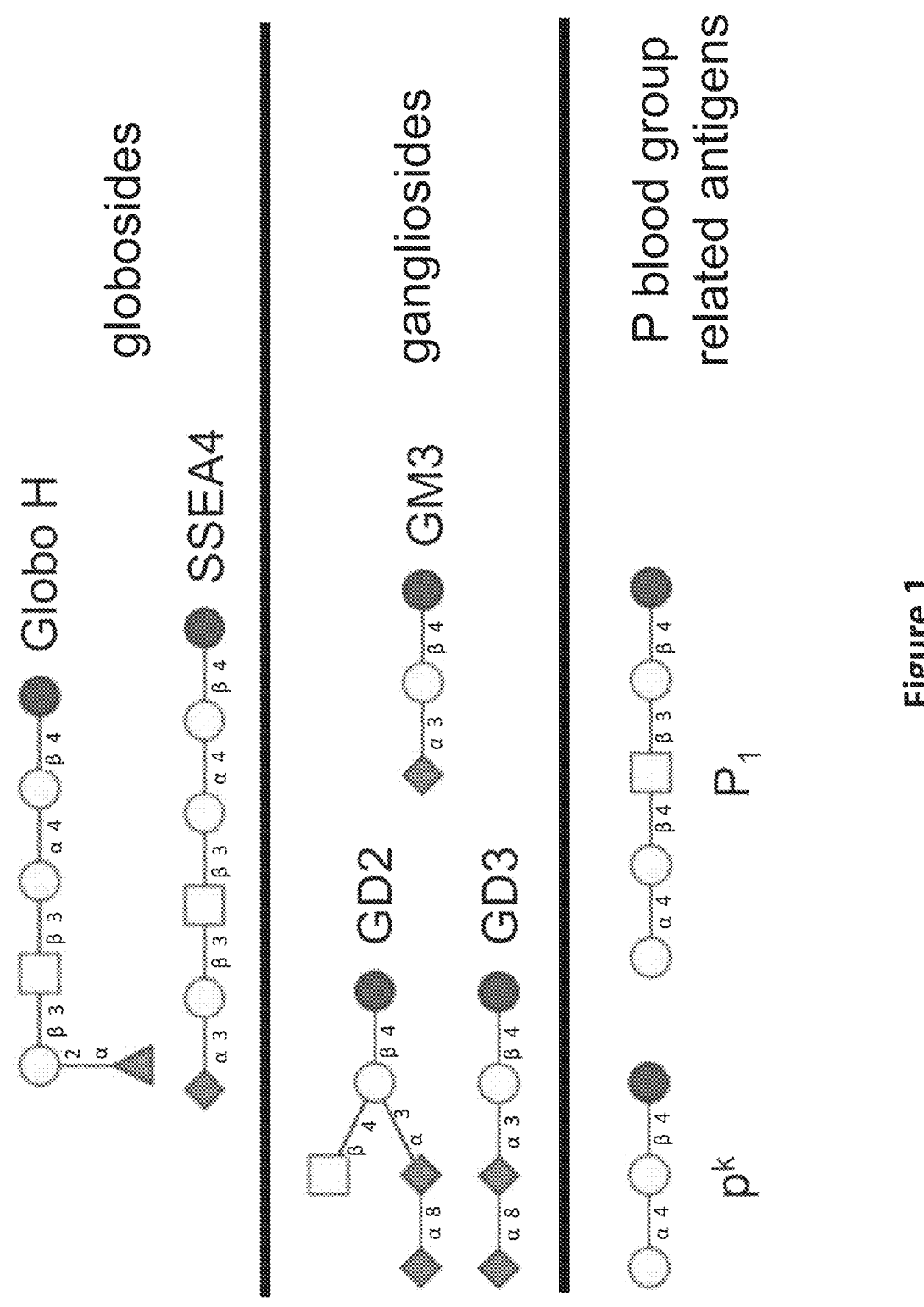
FIG. 1. Examples of tumor-associated glycans from Pochechueva et al., *Metabolites* (2012) December; 2(4): 913-939. Illustrated are some of the glycans known to be involved in gynecological cancers.

Described herein are genomically recoded and engineered organisms, platforms for preparing sequence defined biopolymers in vitro comprising a cellular extract from genomically recoded and engineered organisms, and methods for preparing sequence defined biopolymers in vitro. The organisms and platforms described herein allow for multi-site nsAA incorporation into sequence defined biopolymers prepared in vitro at high yield and purity and post-incorporation modification of the incorporated nsAA in vitro, for example, via glycosylation. The use of a cellular extract from the organisms results in a surprisingly high yield for glycoprotein production. Moreover, the use of the cellular extract resulted in surprisingly high quantities of modified glycoproteins incorporating one or more glycosylated nsAAs. Extracts produced from these genomically modified organisms show surprising promise for production of new-kinds of sequence defined biopolymers, proteins, and in particular, glycoproteins.

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target, "target sequence", "target region", and "target nucleic acid," as used herein, are synonymous and refer to a region or sequence of a nucleic acid which is to be amplified, sequenced, or detected.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, bacteriophage polymerases such as, but not limited to, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer.

Cell-Free Protein Synthesis (CFPS) and Cell-Free Glycoprotein Synthesis (CFGpS)

The disclosed subject matter relates in part to methods, systems, components, and compositions for cell-free protein synthesis. Cell-free protein synthesis (CFPS) is known and has been described in the art. (See, e.g., U.S. Pat. Nos. 6,548,276; 7,186,525; 8,734,856; 7,235,382; 7,273,615; 7,008,651; 6,994,986 7,312,049; 7,776,535; 7,817,794; 8,298,759; 8,715,958; 9,005,920; U.S. Publication No. 2014/0349353, U.S. Publication No. 2016/0060301, U.S. Publication No. 2018/0016612, and U.S. Publication No. 2018/0016614, the contents of which are incorporated herein by reference in their entireties). A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The strains and systems disclosed herein may be applied to cell-free protein methods in order to prepare glycosylated macromolecules (e.g., glycosylated peptides, glycosylated proteins, and glycosylated lipids). Glycosylated proteins that may be prepared using the disclosed strains and systems may include proteins having N-linked glycosylation (i.e., glycans attached to nitrogen of asparagine and/or arginine side-chains) and/or O-linked glycosylation (i.e., glycans attached to the hydroxyl oxygen of serine, threonine, tyrosine, hydroxylysine, and/or hydroxyproline). Glycosylated lipids may include O-linked glycans via an oxygen atom, such as ceramide.

The glycosylated macromolecules disclosed herein may include unbranched and/or branched sugar chains composed of monomers as known in the art such as, but not limited to, glucose (e.g., β-D-glucose), galactose (e.g., β-D-galactose), mannose (e.g., β-D-mannose), fucose (e.g., α-L-fucose), N-acetyl-glucosamine (GlcNAc), N-acetyl-galactosamine (GalNAc), neuraminic acid, N-acetylneuraminic acid (i.e., sialic acid), and xylose, which may be attached to the glycosylated macromolecule, growing glycan chain, or donor molecule (e.g., a donor lipid and/or a donor nucleotide) via respective glycosyltransferases (e.g., oligosaccharyltransferases, GlcNAc transferases, GalNAc transferases, galactosyltransferases, and sialyltransferases). The glycosylated macromolecules disclosed herein may include glycans as known in the art.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

Genomically Recoded Organisms

An aspect of the present invention is a genomically recoded organism (GRO) comprising a strain deficient in release factor 1 (RF1) or a genetic homolog thereof, wherein the GRO further has been engineered to express a heterologous RNA polymerase. GRO comprising a strain deficient in RFT or a genetic homolog thereof may be prepared by any method of strain engineering. In certain embodiments the strain deficient in RF1 is prepared in which all instances of the UAG codon have been removed, permitting the deletion of release factor 1 (RF1; terminates translation at UAG and UAA) and, hence, eliminating translational termination at UAG codons. This GRO allows for the reintroduction of UAG codons, along with orthogonal translation machinery to permit efficient and site-specific incorporation of NSAAs into proteins. That is, UAG may be transformed from a nonsense codon (terminates translation) to a sense codon (incorporates amino acid of choice), provided the appropriate translation machinery is present.

The strain may comprise a prokaryote strain. In some embodiments, the strain is an *E. coli* strain. In certain specific embodiments, the strain is *E. coli* strain C321.ΔprfA, *E. coli* strain rec13.ΔprfA, or a derivative of either *E. coli* strain C321.ΔprfA or *E. coli* strain rec13.ΔprfA. Other suitable strains are disclosed in U.S. Published Application No. 2016/0060301, the content of which is incorporated herein by reference in its entirety.

GROs Engineered to Express a Heterologous RNA Polymerase

In another aspect of the invention, the GRO comprising a strain deficient in RF1 or a genetic homolog thereof further comprises an additional engineered modification in that the GRO is engineered to express a heterologous RNA polymerase. Suitable RNA polymerases may include, but are not limited to, bacteriophage RNA polymerases.

Suitable bacteriophage RNA polymerases for the disclosed methods, systems, components and compositions may include the bacteriophage T7 RNA polymerase or variants thereof. The amino acid sequence of T7 RNA polymerase is provided herein as SEQ ID NO:1 and a DNA sequence encoding T7 RNA polymerase is provided as SEQ ID NO:2. The promoter sequence for T7 RNA polymerase is provided as SEQ ID NO:3 (which may be present on a transcription template for expressing a target protein in the cell-free protein synthesis systems disclosed herein). In some embodiments of the disclosed methods, systems, components and compositions, variants of T7 RNA polymerase may include polymerases having at least about 50%, 60%, 70%, 80%, 90%, 95%, 96%, 97%, 98%, or 99% amino acid sequence identity to SEQ ID NO:1 and/or polymerases encoded by a DNA having at least about 50%, 60%, 70%, 80%, 90%, 95%, 96%, 97%, 98%, or 99% nucleotide sequence identity to SEQ ID NO:2. In some embodiments, variants of T7 RNA polymerase are resistant to cleavage by a host protease of a recombinantly engineered source strain in which the variant T7 RNA polymerase is expressed. For example, a variant of T7 RNA polymerase may include a deletion of 1 or more amino acids, an insertion of one or more amino acids, and/or one or more amino acid substitutions that make the variant resistant to cleavage by a host protease of a recombinantly engineered source strain in which the variant T7 RNA polymerase is expressed. Amino acid substitutions may include replacing one or more basic amino acids (e.g., K172, R173, K179, and/or K180) with an amino acid that is not basic (e.g., a replacement amino acid for K172, R173, K179, and/or K180 selected from A, G, I, and L).

Suitable bacteriophage RNA polymerases for the disclosed methods, systems, components and compositions may include the bacteriophage T3 RNA polymerase or variants thereof. The amino acid sequence of T3 RNA polymerase is provided herein as SEQ ID NO:4 and a DNA sequence encoding T3 RNA polymerase is provided as SEQ ID NO:5. The promoter sequence for T3 RNA polymerase is provided as SEQ ID NO:6 (which may be present on a transcription template for expressing a target protein in the cell-free protein synthesis systems disclosed herein). In some embodiments of the disclosed methods, systems, components and compositions, variants of T3 RNA polymerase may include polymerases having at least about 50%, 60%, 70%, 80%, 90%, 95%, 96%, 97%, 98%, or 99% amino acid sequence identity to SEQ ID NO:4 and/or polymerases encoded by a DNA having at least about 50%, 60%, 70%, 80%, 90%, 95%, 96%, 97%, 98%, or 99% nucleotide sequence identity to SEQ ID NO:5. In some embodiments, variants of T3 RNA polymerase are resistant to cleavage by a host protease of a recombinantly engineered source strain in which the variant T3 RNA polymerase is expressed. For example, a variant of T3 RNA polymerase may include a deletion of 1 or more amino acids, an insertion of one or more amino acids, and/or one or more amino acid substitutions that make the variant resistant to cleavage by a host protease of a recombinantly engineered source strain in which the variant T3 RNA polymerase is expressed. Amino acid substitutions may include replacing one or more basic amino acids (e.g., K173, R174, K180, and/or K181) with an amino acid that is not basic (e.g., a replacement amino acid for K173, R174, K180, and/or K181 selected from A, G, I, and L).

Suitable bacteriophage RNA polymerases for the disclosed methods, systems, components and compositions may include the bacteriophage SP6 RNA polymerase or variants thereof. The amino acid sequence of SP6 RNA polymerase is provided herein as SEQ ID NO:7 and a DNA sequence encoding SP6 RNA polymerase is provided as SEQ ID NO:8. The promoter sequence for SP6 RNA polymerase is provided as SEQ ID NO:9 (which may be present on a transcription template for expressing a target protein in the cell-free protein synthesis systems disclosed herein). In some embodiments of the disclosed methods, systems, components and compositions, variants of SP6 RNA polymerase may include polymerases having at least about 50%, 60%, 70%, 80%, 90%, 95%, 96%, 97%, 98%, or 99% amino acid sequence identity to SEQ ID NO:7 and/or polymerases encoded by a DNA having at least about 50%, 60%, 70%, 80%, 90%, 95%, 96%, 97%, 98%, or 99% nucleotide sequence identity to SEQ ID NO:8. In some embodiments, variants of SP6 RNA polymerase are resistant to cleavage by a host protease of a recombinantly engineered source strain in which the variant SP6 RNA polymerase is expressed. For example, a variant of SP6 RNA polymerase may include a deletion of 1 or more amino acids, an insertion of one or more amino acids, and/or one or more amino acid substitutions that make the variant resistant to cleavage by a host protease of a recombinantly engineered source strain in which the variant SP6 RNA polymerase is expressed. Amino acid substitutions may include replacing one or more of basic amino acids with an amino acid that is not basic (e.g., a replacement amino acid for a basic amino acid selected from A, G, I, and L).

The GRO may be modified to express the heterologous RNA polymerase by methods known in the art including recombination methods known in the art and as disclosed herein. In some embodiments, the GRO is modified to express the heterologous RNA polymerase by recombining a cassette that expresses the heterologous RNA polymerase into the genome of the GRO, the cassette including the coding sequence for the heterologous RNA polymerase (e.g., any of SEQ ID NOs:2, 5, 8 or a variant thereof) operably linked to a suitable promoter for expressing the RNA polymerase. Suitable promoters may include inducible promoters or constitutive promoters. Preferably, the promoter is characterized as a "strong" promoter as described herein.

Additional GRO Modifications Including Knock-Out Mutations

Optionally, the GRO comprising a strain deficient in RF1 or a genetic homolog thereof and engineered to express a heterologous RNA polymerase further comprises at least one additional genetic knock-out mutation. The at least one additional genetic knock-out mutation is preferably a knock-out mutation that downregulates or eliminates a negative protein effector for CFPS. In certain embodiments, the at least one additional genetic knock-out mutation improves DNA stability, RNA stability, protein stability, amino acid stability, energy supply, or any combination thereof. In certain embodiments, the at least one additional genetic knock-out mutation comprises 1, 2, 3, 4, or more than 4 genetic knock-out mutations. In embodiments where the strain comprises 2 or more genetic knock-out mutations, at least 2 of the genetic knock-out mutations may both improve the same attribute, improved DNA stability, improved RNA stability, improved protein stability, improved amino acid stability, improved energy supply, or may both improve different attributes.

To improve DNA or RNA stability, the at least one additional genetic knock-out mutation may target the functional inactivation of nucleases. In vivo, nucleases play important roles in regulating DNA and mRNA turnover. However, their presence in crude cell extracts is expected to be deleterious, leading to template instability and reaction termination. A nonexhaustive list of potential negative effectors follow: RNase A (encoded by ma) degrades RNA by catalyzing the cleavage of phosodiester bonds, and identification of strains (e.g., MRE600, A19) lacking ma was important for early studies in in vitro translation. RNase II (encoded by rnb) is responsible for mRNA decay by 3' to 5' exonuclease activity, and cell extracts lacking RNase II exhibit a 70% increase in CFPS efficiency. RNase E (encoded by me) is part of a cold shock degradosome that induces mRNA decay in cold shock, which the cells experience during harvest prior to extract generation. MazF (encoded by mazF) is a toxin that degrades mRNA by sequence-specific (ACA) endoribonuclease activity, which could affect transcript stability. CsdA (encoded by csdA) is part of a cold shock degradosome along with RNase E and induces mRNA decay in cold shock, which the cells experience during harvest prior to extract generation. DNA-specific endonuclease I (encoded by endA) breaks double-stranded DNA, and its deletion has previously shown to be important for extending the duration of CFPS reactions. These and other nucleases may be functionally inactivated by the at least on additional genetic knock-out mutation.

To improve protein stability, the at least one additional genetic knock-out mutation may target the functional inactivation of proteases. In vivo, these proteases play important roles in regulating protein turnover. However, their presence in CFPS reactions is expected to be deleterious, leading to protein instability issues. A nonexhaustive list of potential negative effectors follow: Glutathione reductase (encoded by gor) reduces oxidized glutathione to maintain a reducing environment in the cytoplasm of a cell, making synthesis of disulfide-bonded proteins problematic. Lon (encoded by ion) is an ATP-dependent protease that demonstrated improved protein production in cell-free systems in BL21 strains upon transcriptional down regulation. Outer membrane protease VII (encoded by ompT) demonstrates specificity for paired basic residues and has been shown to stabilize proteins during CFPS upon removal. These and other proteases may be functionally inactivated by the at least on additional genetic knock-out mutation.

The at least one additional genetic knock-out mutation may target proteins known to negatively affect amino acid or energy supply. In vivo, these proteins play important roles in metabolism and substrate turnover. However, their presence in crude cell extracts is expected to be deleterious, leading to decreased amino acid and energy supply to support translation. A nonexhaustive list of potential negative effectors follow: Glutamate dehydrogenase (encoded by gdhA) catalyzes the deamination of glutamate, which may affect glutamate's stability. Glutamate-cysteine-ligase (encoded by gshA) catalyzes the first step of glutathione synthesis and may decrease the stability of cysteine. Serine deaminase I (encoded by sdaA) and serine deaminase II (encoded by sdaB) are two of the three enzymes involved in serine degradation. Arginine decarboxylase (encoded by speA) consumes arginine in the biosynthetic production of putrescine. Tryptophanase (encoded by tnaA) consumes tryptophan in the production of indole. Lastly, glycerol kinase (encoded by glpK) consumes ATP to phosphorylate glycerol, which could help deplete the energy supply required for cell-free reactions. These and other proteins may be functionally inactivated by the at least on additional genetic knock-out mutation.

In some embodiments, the disclosed strains may include a genomic modification that results in a deficiency in expression of endA and or gor, in particular. In some embodiments, the disclosed strains may include a genomic modification that results in a deletion of at least a portion of endA and or gor, in particular.

In some embodiments, the disclosed strains may include a genomic modification which inactivates and/or deletes a gene selected from gmd, waal or both of gmd and waal, or genetic equivalents thereof. When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2. When the modified strain is *E. coli*, the modification may include an inactivating modification in the waal gene (e.g., via a deletion of at least a portion of the waal gene). The sequence of the *E. coli* waaL gene is provided herein as SEQ ID NO:3 and the amino acid sequence of *E. coli* O-antigen ligase is provided as SEQ ID NO:4.

Strains having at least one additional genetic knock-out mutation may be prepared by any method of engineering a strain to functionally inactivate the negative effector to lessen or eliminate the negative effector from a lysate prepared from the strain. In certain embodiments, the genetic knock-out mutations may be prepared by inserting either a nonsense mutation and/or a frameshift mutation into the genome of the strain as well as deleting a vital portion of a gene coding sequence. In certain embodiments, the genetic knock-out mutations may be prepared by removing regulatory sequences (i.e. promoter, ribosome binding site) or otherwise changing these sequences in the genome as to render them non-functional. In certain embodiments, negative effectors can be functionally knocked out in lysates by introducing a unique affinity tag and subsequently using the tag to selectively remove the effector protein from the lysates. In certain embodiments a strain having at least one additional genetic knock-out mutation may be prepared by multiplex automated genome engineering (MAGE), k-Red recombinase-mediated recombination (Datsenko-Wanner), zinc-finger nucleases (ZFNs), transcription activator-like effector nucleases (TALENs), clustered regularly interspaced short palindromic repeats (CRISPR)-associated protein-9 nuclease (Cas9), and any other commonly used recombineering and genome engineering tools.

Additional GRO Modifications Including Upregulated Gene Products

Optionally, the GRO comprising a strain deficient in RF1 or a genetic homolog thereof further and engineered to express a heterologous RNA polymerase further comprises at least one additional upregulated gene product. In certain embodiments the GRO comprising a strain deficient in RF1 or a genetic homolog thereof further comprises at least one additional upregulated gene product and at least one additional genetic knock-out mutation. The at least one additional upregulated gene product is preferably an upregulated gene product that is a positive effector for CFPS. In certain embodiments, the at least one additional upregulated gene product improves energy supply, chaperone levels, translations function, ribosome recycling, or any combination thereof. In certain embodiments, the at least on additional upregulated gene product comprises 1, 2, 3, 4, or more than 4 upregulated gene products. In embodiments where the strain comprises 2 or more upregulated gene products, at least 2 of the upregulated gene products may both improve the same attribute, improved energy supply, improved chaperone levels, improved translation function, or improved ribosome recycling, or may both improve different attributes.

To improve energy supply, the at least one additional upregulated gene product may target the upregulation of kinases. In vivo, these proteins play important roles in metabolism and the transfer of phosphate groups. The upregulated presence in crude cell extracts is expected to improve energy supply to support translation. A nonexhaustive list of potential positive effectors follow: Acetate kinase (encoded by ackA) increases the overall metabolic flux of metabolites toward substrate-level ATP generation. Nucleoside-diphosphate kinase (encoded by ndk) facilitate the synthesis of NTPs from their corresponding NDPs. Pyruvate kinase monomer (encoded by pykF) helps drive ATP generation. These and other kinases may be the at least one additional upregulated gene product.

To improve energy supply, the at least one additional upregulated gene product may target the upregulate of deaminases. In vivo, these proteins may play important roles in metabolism and preparing metabolites. A nonexhaustive list of potential positive effectors follow: Cytidine deaminase (encoded by cdd) initiates the deamination of cytidine which may lead to the synthesis of UTP. These and other deaminases may be the at least one additional upregulated gene product To improve chaperone levels, the at least one upregulated gene product may target the upregulation of isomerases, foldases and/or holdases. In vivo, these proteins may play important roles in the assisting proteins to adopt functionally active conformations. The upregulated presence in crude cell extracts is expected to improve chaperone levels to support protein production into soluble and/or active confirmations. A nonexhaustive list of potential positive effectors follow: Disulfide bond isomerase (encoded by dsbC) shuffles disulfide bonds into correct positions. Chaperone protein DnaK (encoded by dnaK) aids the folding of nascent polypeptide chains and the rescue of misfolded proteins. Chaperone protein DnaJ (encoded by danJ) stimulates the ATPase activity of DnaK. Protein GrpE (encoded by grpE) stimulates the ATPas activity of DnaK. Trigger Factor (encoded by fig) aids the folding of nascent polypeptides. The 10 kDa chaperonin subunit (encoded by groS) forms part of the GroEL-GroES chaperonin complex that aids in protein folding. The 60 kDa chaperonin subunit (encoded by groL) forms part of the GroEL-GroES chaperonin complex that aids in protein folding. These and other isomerases, foldases, and/or holdases may be the at least one additional upregulated gene product.

To improve translation function, the at least one upregulated gene product may target the upregulation of initiation factors and/or elongation factors. In vivo, these proteins play important roles in the translation function. The upregulated presence in crude cell extracts is expected to improve translation function. A nonexhaustive list of potential positive effectors follow: Translation initiation factor IF-1 (encoded by infA) interacts with the 30S ribosomal subunit to initiate translations. Translation initiation faction IF-2 (encoded by infB) has a role in the proper placement of the charged initiator fMet-tRNA via a GTP-dependent mechanism. Elongations factor G (encoded by fusA) facilitates translocation of the ribosome by one codon along an mRNA. Elongation factor P (encoded by efp) stimulates the synthesis of peptide bonds. Elongation factor 4 (encoded by lepA) can alter the rate of translation, leading to increases in the rate of translation under certain stress conditions. Elongation factor TU 2 (encoded by tufB) helps shuttle charge tRNAs to ribosomes. These and other initiation factors and/or elongation factors may be the at least one additional upregulated gene product.

To improve translation function, the at least one upregulated gene product may target the upregulation of recycling factors. In vivo, these proteins play important roles in the ribosome recycling. The upregulated presence in crude cell extracts is expected to improve ribosome recycling. A nonexhaustive list of potential positive effectors follow: Heat shock protein 15 (encoded by hslR) is involved with the recycling of free 50S ribosomal subunits. Ribosome-recycling factor (encoded by frr) promotes rapid recycling of ribosomal subunits after the release of the polypeptide chain. These and other recycling factors may be the at least one additional upregulated gene product.

Strains having at least one additional genetic knock-out mutation, may be prepared by any method of engineering a strain to functionally increase a positive effector to increase the presence of the positive effector in the lysate prepared from the strain. In certain embodiments, the upregulated gene product is expressed from a plasmid present in the GRO and/or expressed from an integration site in GRO genome. Additionally, gene upregulation may be enhanced by engineering the promoter and/or ribosome binding site in front of your gene of interest located either on a plasmid or on the genome. A stronger promoter/ribosome binding site would lead to an increase in transcriptional activity. Techniques commonly employed to integrate a plasmid overexpressing a positive effector into a strain includes transformation. Techniques commonly employed to integrate a gene cassette containing a positive effector into the genome for overexpression includes X-Red recombinase-mediated recombination (Datsenko-Wanner).

Platforms for Preparing Sequence Defined Biopolymers

An aspect of the invention is a platform for preparing a sequence defined biopolymer of protein in vitro. The platform for preparing a sequence defined polymer or protein in vitro comprises a cellular extract from the GRO organism as described above. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in Application No. PCT/US2015/033221 to Michael C. Jewett et al., entitled TETHERED RIBOSOMES AND METHODS OF MAKING AND USING THEREOF, filed 29 May 2015, and now published as WO2015184283, and U.S. patent application Ser. No. 15/363,828, to Michael C. Jewett et al., entitled RIBOSOMES WITH TETHERED SUBUNITS, filed on Nov. 29, 2016, and now published as U.S. Patent Application Publication No. 2017/0073381, on Mar. 16, 2017, the contents of which are incorporated by reference. In certain embodiments, one or more orthogonal components may be prepared in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture).

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., form about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Cell-Free Glycoprotein Synthesis (CFGpS) in Prokaryotic Cell Lysates Enriched with Components for Glycosylation The disclosed GRO's, compositions, and methods may be utilized for performing cell-free glycoprotein synthesis (CFGpS). In some embodiments, the composition and methods include or utilize prokaryotic cell lysates enriched with components for glycosylation and prepared from genetically modified strains of prokaryotes.

In some embodiments, the genetically modified prokaryote is a genetically modified strain of *Escherichia coli* or any other prokaryote suitable for preparing a lysate for CFGpS. Optionally, the modified strain of *Escherichia coli* is derived from rEc.C321. Preferably, the modified strain includes genomic modifications (e.g., deletions of genes rendering the genes inoperable) that preferably result in lysates capable of high-yielding cell-free protein synthesis. Also, preferably, the modified strain includes genomic modification (e.g., deletions of genes rendering the genes inoperable) that preferably result in lysates comprising sugar precursors for glycosylation at relatively high concentrations (e.g., in comparison to a strain not having the genomic modification). In some embodiments, a lysate prepared from the modified strain comprises sugar precursors at a concentration that is at least 20%, 30%, 40%, 50%, 60%, 70%, 80%, 90%, 100%, 150%, 200%, or higher than a lysate prepared from a strain that is not modified.

In some embodiments, the modified strain includes a modification that results in an increase in the concentration of a monosaccharide utilized in glycosylation (e.g., glucose, mannose, N-acetyl-glucosamine (GlcNAc), N-acetyl-galactosamine (GalNAc), galactose, sialic acid, neuraminic acid, fucose). As such, the modification may inactivate an enzyme that metabolizes a monosaccharide or polysaccharide utilized in glycosylation. In some embodiments, the modification inactivates a dehydratase or carbon-oxygen lyase enzyme (EC 4.2) (e.g., via a deletion of at least a portion of the gene encoding the enzyme). In particular, the modification may inactivate a GDP-mannose 4,6-dehydratase (EC 4.2.1.47). When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2.

In some embodiments, the modified strain includes a modification that inactivates an enzyme that is utilized in the glycosyltransferase pathway. In some embodiments, the modification inactivates an oligosaccharide ligase enzyme (e.g., via a deletion of at least a portion of the gene encoding the enzyme). In particular, the modification may inactivate an O-antigen ligase that optionally conjugates an O-antigen to a lipid A core oligosaccharide. The modification may include an inactivating modification in the waaL gene (e.g., via a deletion of at least a portion of the waaL gene). The sequence of the *E. coli* waaL gene is provided herein as SEQ ID NO:3 and the amino acid sequence of *E. coli* O-antigen ligase is provided as SEQ ID NO:4.

In some embodiments, the modified strain includes a modification that inactivates a dehydratase or carbon-oxygen lyase enzyme (e.g., via a deletion of at least a portion of the gene encoding the enzyme) and also the modified strain includes a modification that inactivates an oligosaccharide ligase enzyme (e.g., via a deletion of at least a portion of the gene encoding the enzyme). The modified strain may include an inactivation or deletion of both gmd and waaL.

In some embodiments, the modified strain may be modified to express one or more orthogonal or heterologous genes. In particular, the modified strain may be genetically modified to express an orthogonal or heterologous gene that is associated with glycoprotein synthesis such as a glycosyltransferase (GT) which is involved in the lipid-linked oligosaccharide (LLO) pathway. In some embodiments, the modified strain may be modified to express an orthogonal or heterologous oligosaccharyltransferase (EC 2.4.1.119) (OST). Oligosaccharyltransferases or OSTs are enzymes that transfer oligosaccharides from lipids to proteins.

In particular, the modified strain may be genetically modified to express an orthogonal or heterologous gene in a glycosylation system (e.g., an N-linked glycosylation system and/or an O-linked glycosylation system). The N-linked glycosylation system of *Campylobacter jejuni* has been transferred to *E. coli*. (See Wacker et al., "N-linked glycosylation in *Campylobacter jejuni* and its functional transfer into *E. coli*," *Science* 2002, November 29; 298(5599):1790-3, the content of which is incorporated herein by reference in its entirety). In particular, the modified strain may be modified to express one or more genes of the pgl locus of *C. jejuni* or *C. lari* or one or more genes of a homologous pgl locus. The genes of the pgl locus include pglG, pglF, pglE, wlaJ, pglD, pglC, pglA, pglB, pglJ, pglI, pglH, pglK, and gne, and are used to synthesize lipid-linked oligosaccharides (LLOs) and transfer the oligosaccharide moieties of the LLOs to a protein via an oligosaccharyltransferase.

Suitable orthogonal or heterologous oligosaccharyltransferases (OST) which may be expressed in the genetically modified strains may include *C. jejuni* or *C. lari* oligosaccharyltransferase PglB. The gene for the *C. jejuni* OST is referred to as pglB, which sequence is provided as SEQ ID NO:5 and the amino acid sequence of *C. jejuni* PglB is provided as SEQ ID NO:6. PglB catalyzes transfer of an oligosaccharide to a D/E-Y-N-X-S/T motif (Y, X≠P) present on a protein.

Crude cell lysates may be prepared from the modified strains disclosed herein. The crude cell lysates may be prepared from different modified strains as disclosed herein and the crude cell lysates may be combined to prepare a mixed crude cell lysate. In some embodiments, one or more crude cell lysates may be prepared from one or more modified strains including a genomic modification (e.g., deletions of genes rendering the genes inoperable) that preferably result in lysates comprising sugar precursors for glycosylation at relatively high concentrations (e.g., in comparison to a strain not having the genomic modification). In some embodiments, one or more crude cell lysates may be prepared from one or more modified strains that have been modified to express one or more orthogonal or heterologous genes or gene clusters that are associated with glycoprotein synthesis. Preferably, the crude cell lysates or mixed crude cell lysates are enriched in glycosylation components, such as lipid-linked oligosaccharides (LLOs), glycosyltransferases (GTs), oligosaccharyltransferases (OSTs), or any combination thereof. More preferably, the crude cell lysates or mixed crude cell lysates are enriched in $Man_3GlcNAc_2$ LLOs representing the core eukaryotic glycan and/or $Man_3GlcNAc_4Gal_2Neu_5Ac_2$ LLOs representing the fully sialylated human glycan.

The disclosed crude cell lysates may be used in cell-free glycoprotein synthesis (CFGpS) systems to synthesize a variety of glycoproteins. The glycoproteins synthesized in the CFGpS systems may include prokaryotic glycoproteins and eukaryotic proteins, including human proteins. The CFGpS systems may be utilized in methods for synthesizing glycoproteins in vitro by performing the following steps using the crude cell lysates or mixtures of crude cell lysates disclosed herein: (a) performing cell-free transcription of a gene for a target glycoprotein; (b) performing cell-free translation; and (c) performing cell-free glycosylation. The methods may be performed in a single vessel or multiple vessels. Preferably, the steps of the synthesis method may be performed using a single reaction vessel. The disclosed methods may be used to synthesis a variety of glycoproteins, including prokaryotic glycoproteins and eukaryotic glycoproteins.

Methods for Preparing Proteins and Sequence Defined Biopolymers

An aspect of the invention is a method for cell-free protein synthesis of a sequence defined biopolymer or protein in vitro. The method comprises contacting a RNA template encoding a sequence defined biopolymer with a reaction mixture comprising a cellular extract from a GRO as described above. Methods for cell-free protein synthesis of a sequence defined biopolymers have been described.

In certain embodiments, a sequence-defined biopolymer or protein comprises a product prepared by the method or the platform that includes an amino acids. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. An unnatural amino acids may also be referred to as a non-standard amino acid (NSAA) or non-canonical amino acid. In certain embodiments, a sequence defined biopolymer or protein may comprise a plurality of unnatural amino acids. In certain specific embodiments, a sequence defined biopolymer or protein may comprise a plurality of the same unnatural amino acid. The sequence defined biopolymer or protein may comprise at least 5, at least 10, at least 15, at least 20, at least 25, at least 30, at least 35, or at least 40 or the same or different unnatural amino acids.

Examples of unnatural, non-canonical, and/or non-standard amino acids include, but are not limited, to a p-azido-L-phenylalanine, a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 24ufa24hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an $\alpha$-hydroxy containing acid; an amino thio acid; an $\alpha,\alpha$ disubstituted amino acid; a $\beta$-amino acid; a $\gamma$-amino acid, a cyclic amino acid other than proline or histidine, and an aromatic amino acid other than phenylalanine, tyrosine or tryptophan.

The methods described herein allow for preparation of sequence defined biopolymers or proteins with high fidelity to a RNA template. In other words, the methods described herein allow for the correct incorporation of unnatural, non-canonical, and/or non-standard amino acids as encoded by an RNA template. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and a product prepared from the method includes at least 80%, at least 85%, at least 90%, at least 95%, or 100% of the encoded unnatural, non-canonical, and/or non-standard amino acids.

The methods described herein also allow for the preparation of a plurality of products prepared by the method. In certain embodiments, at least 80%, at least 85%, at least 90%, at least 95%, or at least 98% of a plurality of products prepared by the method are full length. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and at least 80%, at least 85%, at least 90%, at least 95%, or at least 98% of a plurality of products prepared by the method include 100% of the encoded unnatural, non-canonical, and/or non-standard amino acids.

In certain embodiments, the sequence defined biopolymer or the protein encodes a therapeutic product, a diagnostic product, a biomaterial product, an adhesive product, a biocomposite product, or an agricultural product.

Strain-Promoted Alkyne-Azide Cycloadditions (SPAAC)

Strain-promoted alkyne-azide cycloadditions (SPAAC) and the use of SPAAC in cell-free glycoprotein synthesis are contemplated herein. SPAAC has been described. (See, e.g., Mbua et al., Chembiochem. 2011 Aug. 16; 12(12):1912-21; Darabedian et al., Biochemistry 2018 Oct. 9; 57 (40): 5769-5774; Zhang et al., Molecules 2013, 18, 7145-7145;

the contents of which are incorporated herein by reference in their entireties). The disclosed compositions and methods may comprise and/or utilize components for performing SPPAC reactions, which may include, but are not limited components comprising dibenzocyclooctyne (DBCO) moieties and derivatives thereof such as DBCO-amine, DBCO-acid, DBCO-N-hydroxysuccinimidyl ester, DBCO-maleimide, and PEGylated forms thereof such as DBCO-PEG4-acid. In some embodiments, the component comprising a DBCO moiety may be conjugated to a saccharide or a fluorophore (e.g., TAMRA) and the DBCO moiety may be utilized to link the saccharide or the fluorophore to a non-standard amino acid (e.g., pAzF) of an amino acid polymer via click chemistry in a cell-free glycoprotein synthesis (CFGpS) platform.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Illustrative Embodiments

The following embodiments are illustrative and should not be interpreted to limit the scope of the claimed subject matter.

Embodiment 1. *Escherichia coli* chassis strains with genomic modifications that result in lysates capable of high-yielding cell-free protein synthesis and which accumulate sugar precursors for glycosylation.

Embodiment 2. The *Escherichia coli* chassis strains of embodiment 1, wherein the *Escherichia coli* chassis strains are based on genomically recoded *E. coli* that lack release factor 1 with genomic modifications that result in lysates capable of high-yielding cell-free protein synthesis and which accumulate sugar precursors for glycosylation.

Embodiment 3. *Escherichia coli* chassis strains derived from rEc.C321 prfA-gor-endA- with genomic modifications that result in lysates capable of high-yielding cell-free protein synthesis and which accumulate sugar precursors for glycosylation.

Embodiment 4. The strains described in any of embodiments 1-3, in which the genomic modification is an inactivation or deletion of gmd.

Embodiment 5. The strains described in any of embodiments 1-4, in which the genomic modification is an inactivation or deletion of waaL.

Embodiment 6. The strains described in any of embodiments 1-5, in which the genomic modification is an inactivation or deletion of both gmd and waaL.

Embodiment 7. A method for crude cell lysate preparation in which orthogonal genes or gene clusters are expressed in the source strain, which results in lysates enriched with glycosylation components (lipid-linked oligosaccharides (LLOs), oligosaccharyltransferases (OSTs), or both LLOs and OST) and (an) orthogonal translation system(s) (OTS) (orthogonal tRNA(s), engineered aminoacyltRNA synthetase(s) (aaRS), engineered elongation factors(s) (EF), or any combination of tRNAs, aaRSs, and elongation factors), optionally wherein the crude cell lysate is prepared from any of the strains described in embodiments 1-6.

Embodiment 8. The method of embodiment 7, in which the source strain overexpresses a glycosyltransferase pathway from *C. jejuni*, resulting in the production of *C. jejuni* lipid-linked oligosaccharides (LLOs).

Embodiment 9. The method of embodiment 7 or 8, in which the source strain overexpresses a glycosyltransferase pathway from *C. lari*, resulting in the production of *C. lari* lipid-linked oligosaccharides (LLOs).

Embodiment 10. The method of any of embodiments 7-9, in which the source strain overexpresses a synthetic glycosyltransferase pathway, resulting in the production of GlcNAcGalNAc5 lipid-linked oligosaccharides (LLOs).

Embodiment 11. The method of any of embodiments 7-10, in which the OST is a naturally occurring bacterial homolog of *C. jejuni* PglB.

Embodiment 12. The method of any of embodiments 7-11, in which the OST is an engineered variant of *C. jejuni* PglB.

Embodiment 13. The method of any of embodiments 7-12, in which the OST is a naturally occurring archaeal OST.

Embodiment 14. The method of any of embodiments 7-13, in which the OST is a naturally occurring single-subunit eukaryotic OST, such as those found in *Trypanosoma bruceii*.

Embodiment 15. The method of any of embodiments 7-14, in which the source strain overexpresses a synthetic glycosyltransferase pathway, resulting in the production of Man3GlcNAc2 lipid-linked oligosaccharides (LLOs).

Embodiment 16. The method of any of embodiments 7-15, in which the source strain overexpresses a synthetic glycosyltransferase pathway, resulting in the production of Man5GlcNAc3 lipid-linked oligosaccharides (LLOs).

Embodiment 17. The method of any of embodiments 7-16, in which the source strain overexpresses a glycosyltransferase pathway and an OST, resulting in the production of LLOs and OST.

Embodiment 18. The method of any of embodiments 7-16, in which the source strain overexpresses an O antigen glycosyltransferase pathway, resulting in the production of O antigen lipid-linked oligosaccharides (LLOs).

Embodiment 19. The method of any of embodiments 7-18, in which the OTS is engineered to install p-azido-L-phenylalanine (pAzF).

Embodiment 20. The method of any of embodiments 7-19, in which the OTS is engineered to install p-propargyloxy-L-phenylalanine (pAcF).

Embodiment 21. The method of any of embodiments 7-20, in which the OTS installs phosphoserine (Sep).

Embodiment 22. The method of any of embodiments 7-21, in which the OTS installs any amino acid other than the 20 canonical amino acids.

Embodiment 23. A method for cell-free production of nsAA-containing glycoproteins that involves crude cell lysates.

Embodiment 24. The method of embodiment 23, in which the immunogenic carrier is a protein.

Embodiment 25. The method of embodiment 23 or 24, in which the immunogenic carrier is a peptide.

EXAMPLES

The following Examples are illustrative and are not intended to limit the scope of the claimed subject matter.

Example 1—Coordinated Non-Standard Amino Acid Incorporation and Protein Glycosylation in Crude Cell Lysates

Abstract

Glycosylation, or the attachment of glycans (sugars) to proteins, is the most abundant post-translational modification in nature and plays a pivotal role in protein folding, sorting, and activity. In molecular medicine, the compositions and patterns of glycans on recombinant therapeutic glycoproteins are known to impact pharmacokinetics and drug activity. The inability to precisely control protein glycosylation with current technologies represents a key challenge in the fields of glycoprotein synthesis and glycoprotein therapeutics. To address this challenge, PEGylation, or the chemical conjugation of hydrophilic poly(ethylene glycol) (PEG) polymers to proteins, has been used to mimic the effects of glycosylation to a certain extent by improving water solubility, increasing bioavailability, modulating immunogenicity, and extending therapeutic protein half-life in vivo. This strategy has been especially useful in generating long-acting forms of small protein hormones that are naturally glycosylated, such as PEGylated human erythropoietin (Mircera) and PEGylated human growth hormone (Somavert/Pegvisomant). However, the therapeutic efficacy and biochemical properties of molecules that are both PEGylated and glycosylated has not yet been explored.

Here, we describe a CFGpS system with the potential to enable controllable glycosylation of therapeutic proteins containing bio-orthogonal chemical handles for site-specific chemical conjugation of PEG or other chemical groups, including drug conjugates (e.g., antibody-drug conjugates or ADCs). This is accomplished through the co-translational incorporation of non-standard amino acids (nsAAs) and the post-translational attachment of glycans to specific amino acid sequences (sequons) in the protein of interest. Uniquely, in our platform technology, i) all the biosynthetic machinery for protein synthesis and glycosylation is supplied by the *E. coli* lysate and ii) transcription, translation (including non-standard amino acid incorporation), and glycosylation occur in an all-in-one in vitro reaction. We engineered chassis strains that are optimized for coordinated glycosylation and nsAA incorporation and produce up to 1-1.5 g/L protein in cell-free protein synthesis. We showed that an orthogonal translation system (OTS) for incorporation of the p-azidophenylalanine (pAzF) nsAA can be functionally co-expressed with the native *Campylobacter jejuni* glycosylation pathway in the chassis strain and that both OTS and glycosylation components are present in crude *E. coli* lysates and participate in coordinated, in vitro pAzF incorporation and N-linked glycosylation. This resulted in the in vitro production of pAzF-containing glycoproteins in reactions lasting 20 hours. This technology has promising applications as a high-throughput prototyping platform for glycoproteins containing bio-orthogonal chemical handles that are of potential biotechnological interest. This platform opens the door to on-demand synthesis of multiply modified glycoproteins for fundamental biology investigations or therapeutic applications

Applications

Applications of the disclosed technology include, but are not limited to: (i) rapid expression of glycosylated and PEGylated proteins as potential therapeutic candidate molecules; (ii) expression of multiply modified proteins bearing one or more site-specifically installed post-translational modifications for fundamental biology studies or therapeutic applications; (iii) prototyping novel candidate molecules for PEGylated and glycosylated protein therapeutics; and (iv) production platform for long-acting glycosylated protein therapeutics

Advantages

Advantages of the disclosed technology include, but are not limited to: (i) first prokaryotic cell-free system capable of coordinated, cell-free transcription, translation, non-standard amino acid incorporation, and glycosylation of proteins; (ii) enabled production of pAzF-containing glycoproteins in one-pot reactions lasting 20 hours; (iii) rapid prototyping of novel PEGylated or drug-conjugated glycoprotein therapeutics; and (iv) facile method for production of proteins containing multiple post-translational modifications (e.g., glycosylation and phosphorylation) for fundamental biology investigations or therapeutic applications.

Description of Technology

Attachment of chemical groups to proteins is typically accomplished through conjugation chemistries with lysine or cysteine residues, or with the N- or C-termini of the polypeptide backbone. However, these approaches typically result in heterogeneously conjugated protein products, since the conjugation can take place at any of the reactive residues within a protein and can occur with varying degrees of efficiency on the same protein substrate. To address this issue of conjugate heterogeneity, nsAA incorporation has been shown to enable site-specific conjugation of chemical groups to proteins through the introduction of a bio-orthogonal chemical handle in the side chain of the nsAA.

Here, we leverage the specificity of nsAA incorporation and further add the ability to glycosylate proteins site specifically. Others have shown the ability to site-specifically incorporate a glycan into a protein via enzymatic glycosylation of the introduction of an nsAA with a glycosylated side chain. Additionally, it has been shown that an existing glycan on a protein can be chemically modified for attachment of chemical groups. However, to our knowledge, there is no existing method for producing proteins containing both a bio-orthogonal chemical handle and a glycan. We show that this can be accomplished in a one-pot in vitro reaction, opening the door to production of multiply modified proteins for fundamental investigations or therapeutic applications.

Our technology makes it possible to synthesize glycosylated proteins bearing bio-orthogonal chemical handles in an all-in-one in vitro reaction. This advance decreases the time to produce these proteins from days to hours and has promising applications for the production of glycoproteins modified with multiple chemical groups for fundamental biology studies (e.g., combined glycosylation and phosphorylation, etc.) or for therapeutic applications.

We are not are of any previously reported prokaryotic cell-free system with the capability to produce nsAA-containing glycoproteins. There are commercial eukaryotic cell lysate systems for cell-free glycoprotein production (Promega, ThermoFisher), but these systems do not involve overexpression of orthogonal glycosylation machinery and do not enable modular, user-specified glycosylation in the manner that the presently disclosed system can. Additionally, to our knowledge, these systems have not yet been shown to be compatible with nsAA incorporation, nor have they been shown to enable coordinated nsAA incorporation and glycosylation.

There are commercial purified or prokaryotic crude lysate cell-free systems for cell-free protein synthesis (Promega, ThermoFisher). These platforms can be modified through the addition of purified OTS components for nsAA incorporation. However, unlike our engineered strains, the commercial crude lysate systems contain release-factor 1, which reduces the efficiency of nsAA incorporation. Additionally, none of the commercial purified or prokaryotic cell-free systems have the ability to carry out coordinated transcription, translation (including nsAA incorporation), and glycosylation, which we describe here.

Our technology uniquely enables the facile, one-pot production of proteins bearing both bio-orthogonal chemical handles and user-specified glycosylation. This type of molecule represents a very interesting and unexplored class of molecules that we anticipate will help advance fundamental science and have significant utility as a novel class of therapeutic proteins. In particular, given the substantial current investment from the biotechnology and pharmaceutical industries in protein conjugates such as antibody-drug conjugates (ADCs), we think the ability to synthesize glycoprotein conjugates will be of significant interest to these industries in the future.

Example 2—Customizable, In Vitro Protein Glycosylation for Antibacterial and Anti-Cancer Vaccines Reference is made to the presentation entitled "Customizable, in vitro protein glycosylation for antibacterial and anti-cancer vaccines," Stark et al., presented on Apr. 17, 2018, at the American Association for Cancer Research (AACR) Annual Meeting, and Abstract LB-304, Customizable, in vitro protein glycosylation for antibacterial and anti-cancer vaccines, Stark et al., published July 2018, Cancer Research, Volume 78, Issue 13, the contents of which are incorporated herein by reference in their entireties.

Glycans represent a potential therapeutic antigen target. FIG. 1 provides examples of tumor-associated glycans from Pochechueva et al., *Metabolites* (2012) December; 2(4): 913-939, the content of which is incorporated herein by reference in its entirety. Particularly illustrated in FIG. 1 are some of the glycans known to be involved in gynecological cancers. As such, the illustrated tumor-associated glycan may be useful as therapeutic antigen targets against cancers such as gynecological cancers.

Figure 2:
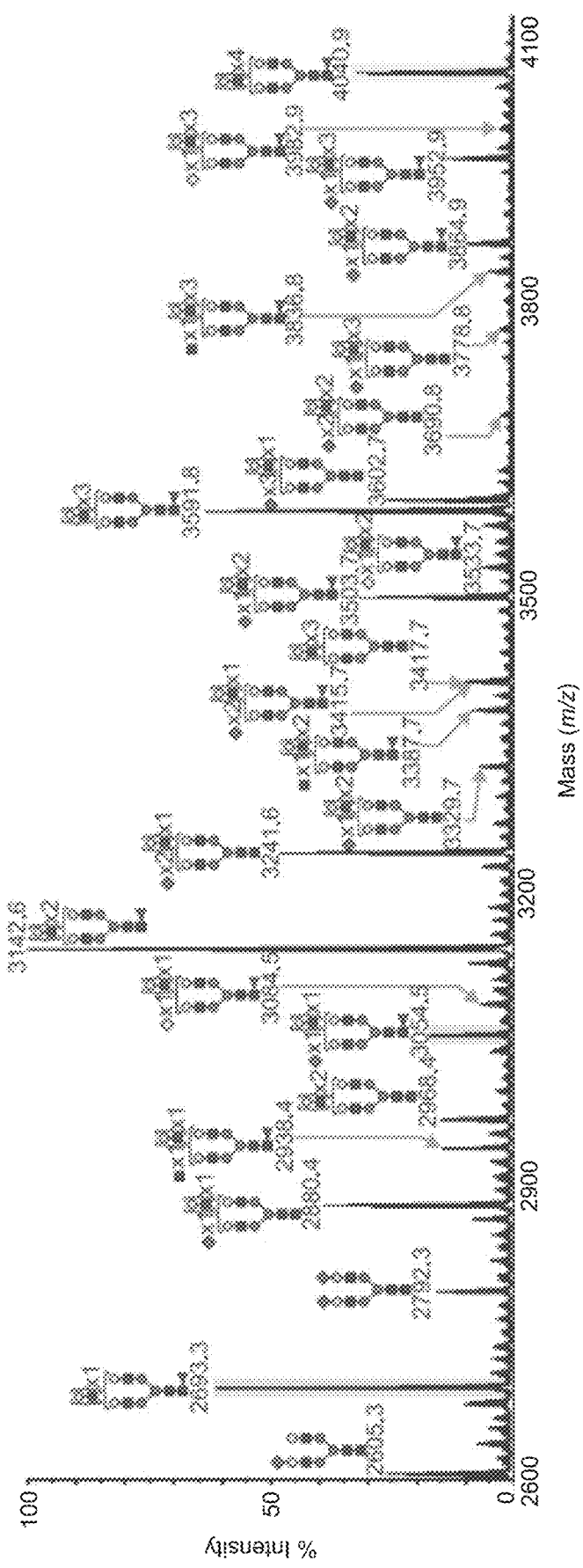
FIG. 2. Illustrative glycans observed in Chinese Hamster Ovary (CHO) cells from Sheridan et al., *Nat. Biotechnol.* (2007), volume 25, pages 145-146.

However, the inability to prepare protein carriers comprising precise glycan structures limits the utility of glycans as therapeutic targets. For example, FIG. 2 illustrates the complexity of glycans observed in Chinese Hamster Ovary (CHO) cells from Sheridan et al., *Nat. Biotechnol.* (2007), volume 25, pages 145-146, the content of which is incorporated herein by reference in its entirety.

Figure 3:
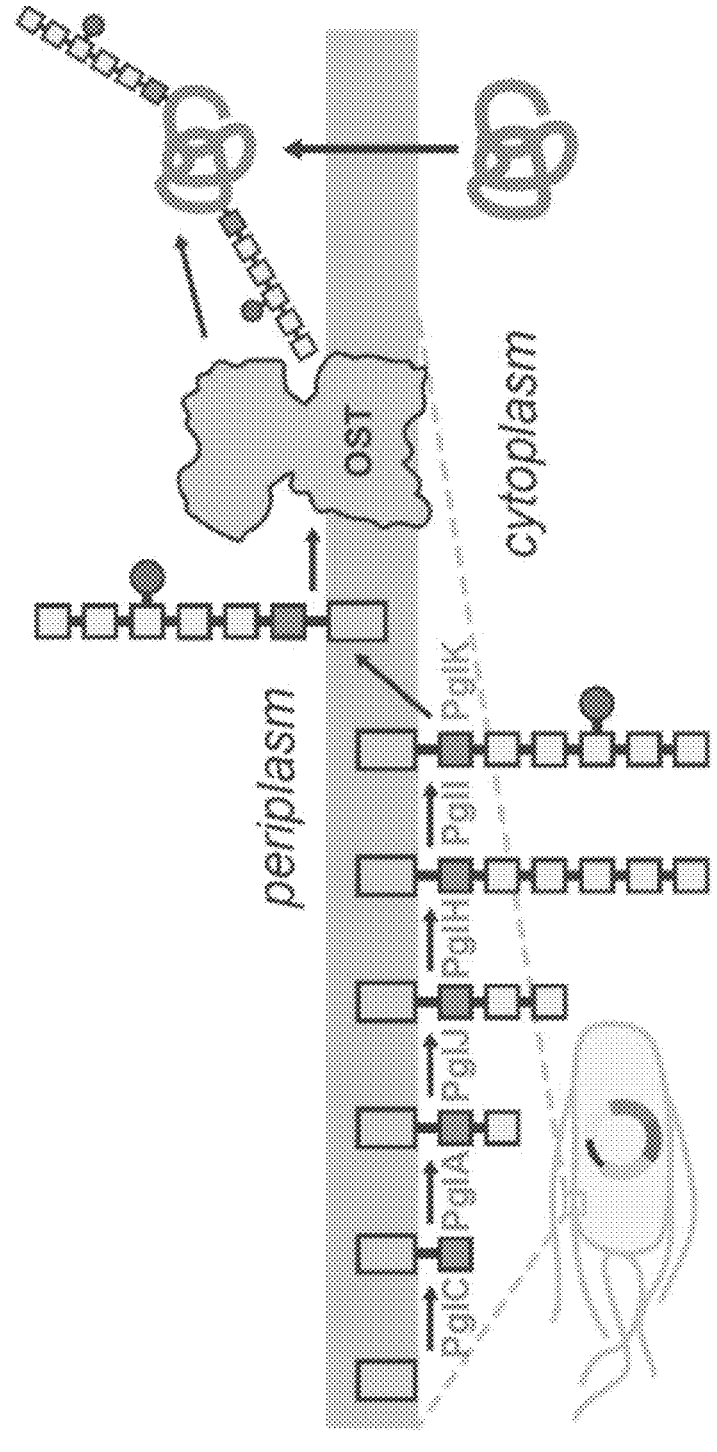
FIG. 3. Illustration of bacterial engineering enabling programmable glycosylation in *Escherichia coli*. (A) Illustration of *Campylobacter jejuni* N-glycosylation from Wacker et al., *Science* (2002), November 29; 298(5599): 1790-3. (B) Illustration of Eukaryotic trimannose core N-glycosylation from Valderrama-Rincon et al., *Nat. Chem. Biol.* (2012), March 25; 8(5):434-6. doi: 10.1038/nchembio.921.
Figure 3:
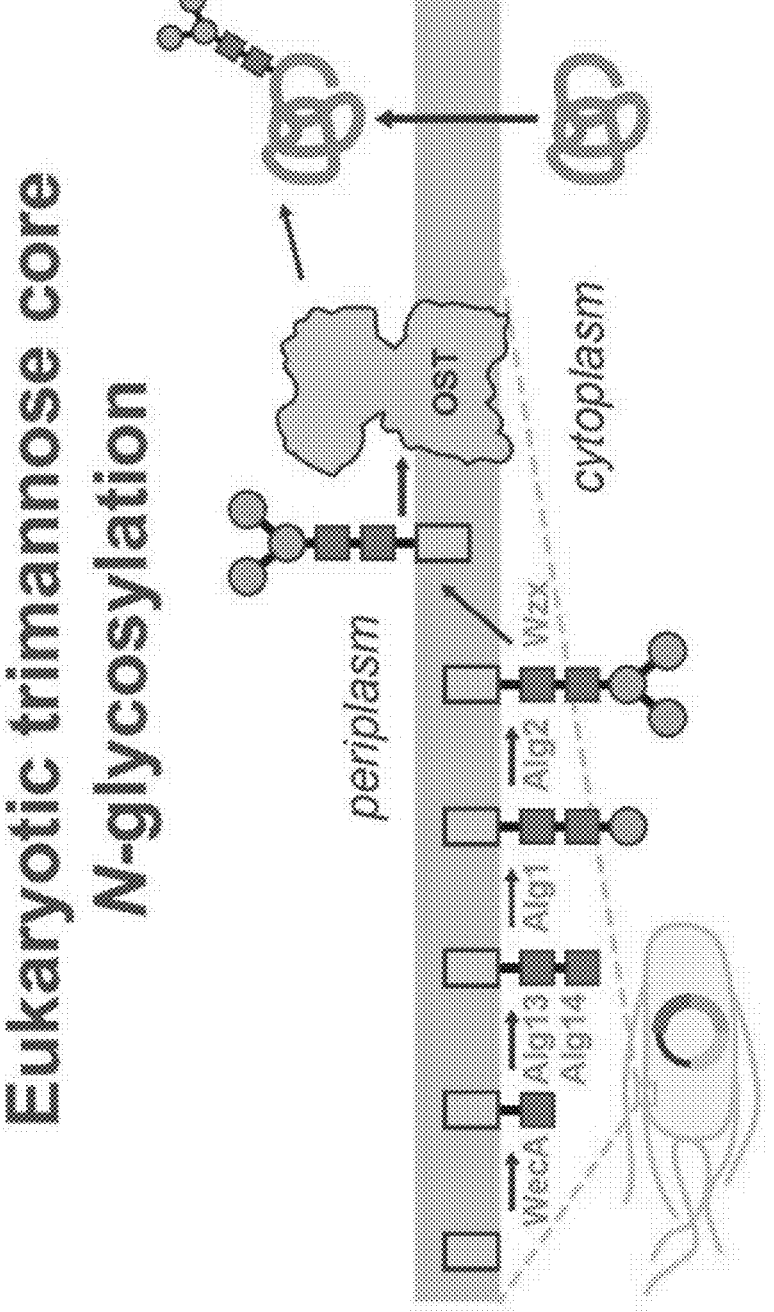

However, bacterial engineering enables programmable glycosylation in *Escherichia coli*. FIG. 3A illustrates the use of the *Campylobacter jejuni* N-glycosylation pathway in *E. coli* to prepare a recombinant glycosylated protein. (See Wacker et al., *Science* (2002), November 29; 298(5599): 1790-3, the content of which is incorporated herein by reference in its entirety. FIG. 3B illustrates eukaryotic trimannose core N-glycosylation in *E. coli* to prepare recombinant glycosylated protein. (See Valderrama-Rincon et al., *Nat. Chem. Biol.* (2012) March 25; 8(5):434-6. doi: 10.1038/nchembio.921, the content of which is incorporated herein by reference in its entirety.

Figure 4:
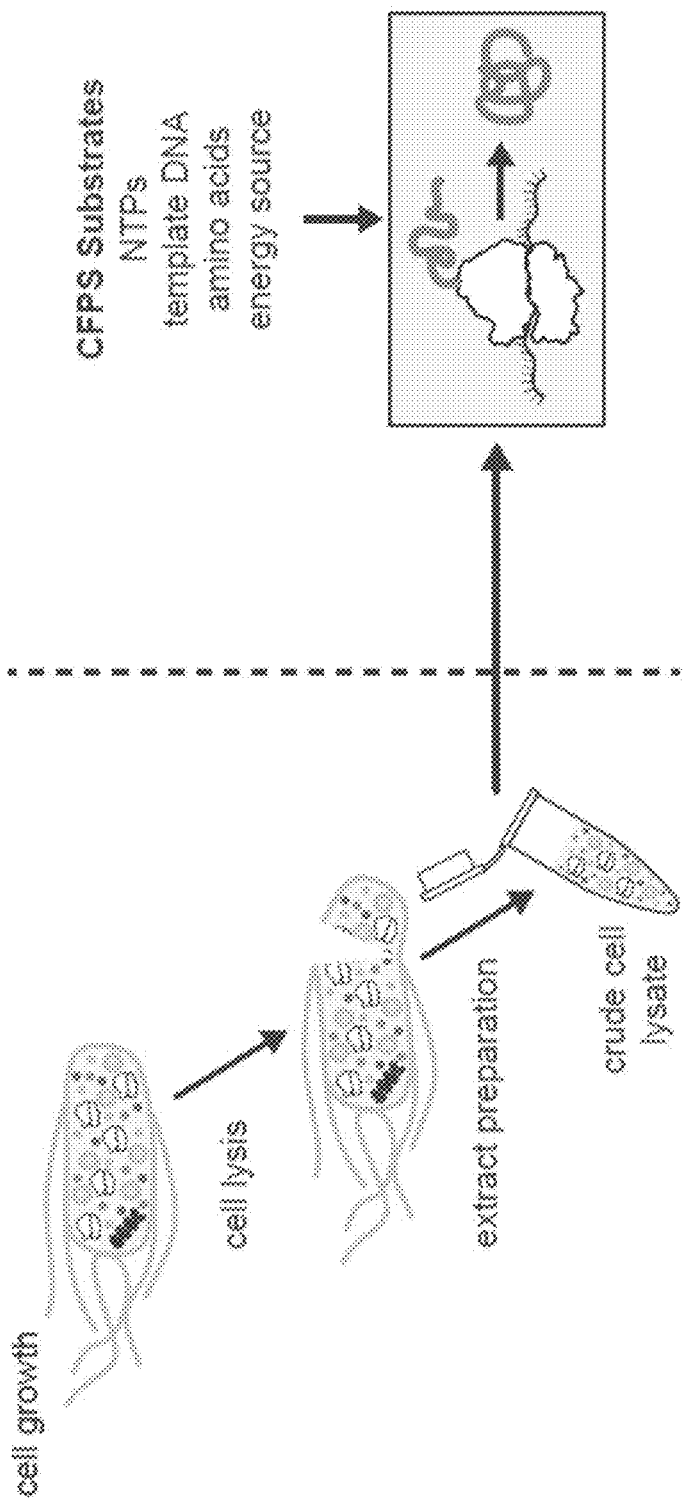
FIG. 4. Illustration of the use of cell-free biology to enable precise control over protein synthesis and glycosylation.

Cell-free systems provide additional control over protein synthesis and glycosylation in vitro. FIG. 4 illustrates the use of cell-free biology to enable precise control over protein synthesis and glycosylation. Cell-free systems offer an open reaction environment for facile addition or removal of glycosylation components and monitoring of reaction conditions.

Figure 5:
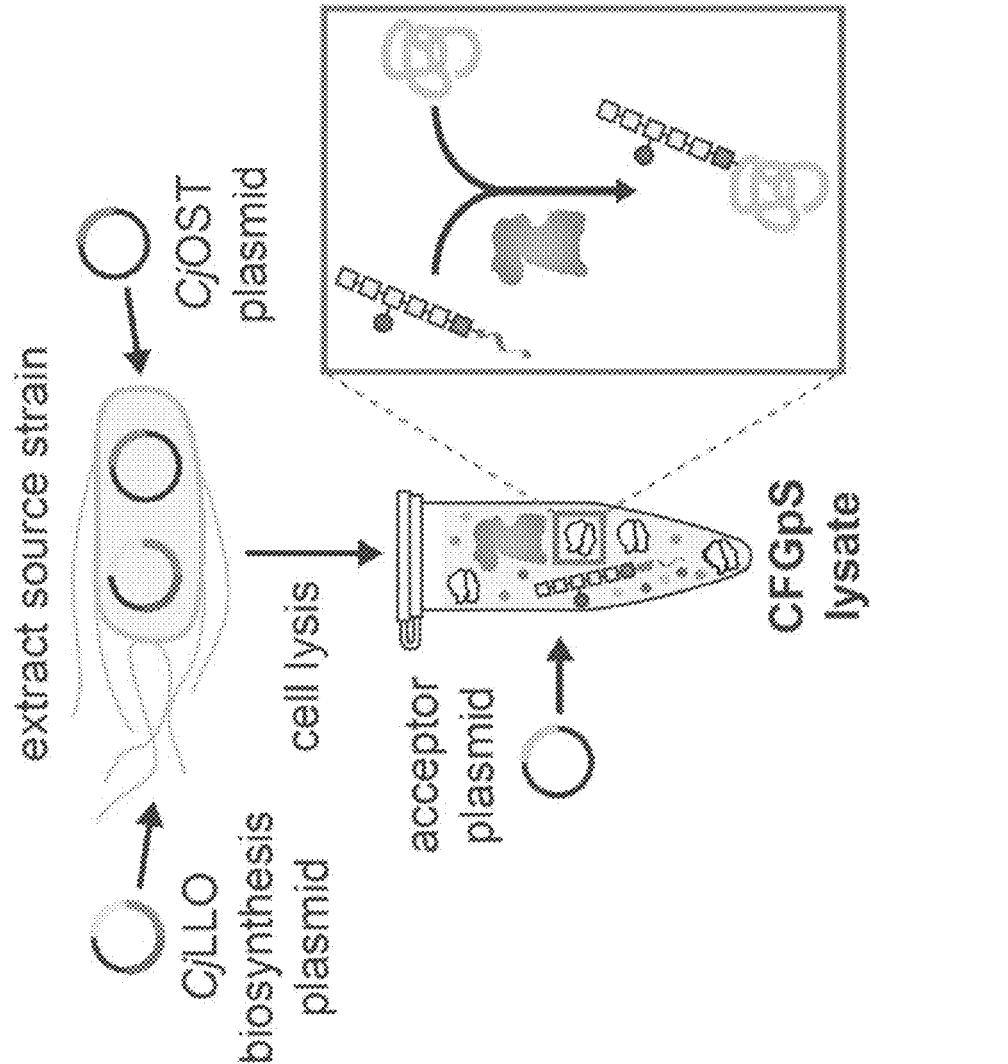
FIG. 5. Crude *E. coli* lysates can be enriched with glycosylation components via overexpression in the source strain for lysate production. (A) CjLLO plasmid which expresses *Campylobacter jejuni* lipid-linked oligosaccharides (LLO) and CjOST plasmid which expresses *Campylobacter jejuni* oligosaccharide transfersase (OST) are introduced into a source strain to provide a cell lysate enriched in LLO and OST. An acceptor plasmid expressing an acceptor polypeptide is introduced into a cell-free glycoprotein synthesis (CFGpS) reaction mixture comprising the cell lysate to prepare a glycosylated acceptor polypeptide. (B) Western blot of glycosylated single chain antibody variable fragment (scFv) and glycosylated green fluorescent protein (GFP) probed with anti-histidine antibody ($\alpha$-His) or anti-glycan antibody ($\alpha$-Glycan).
Figure 5:
Figure 5:
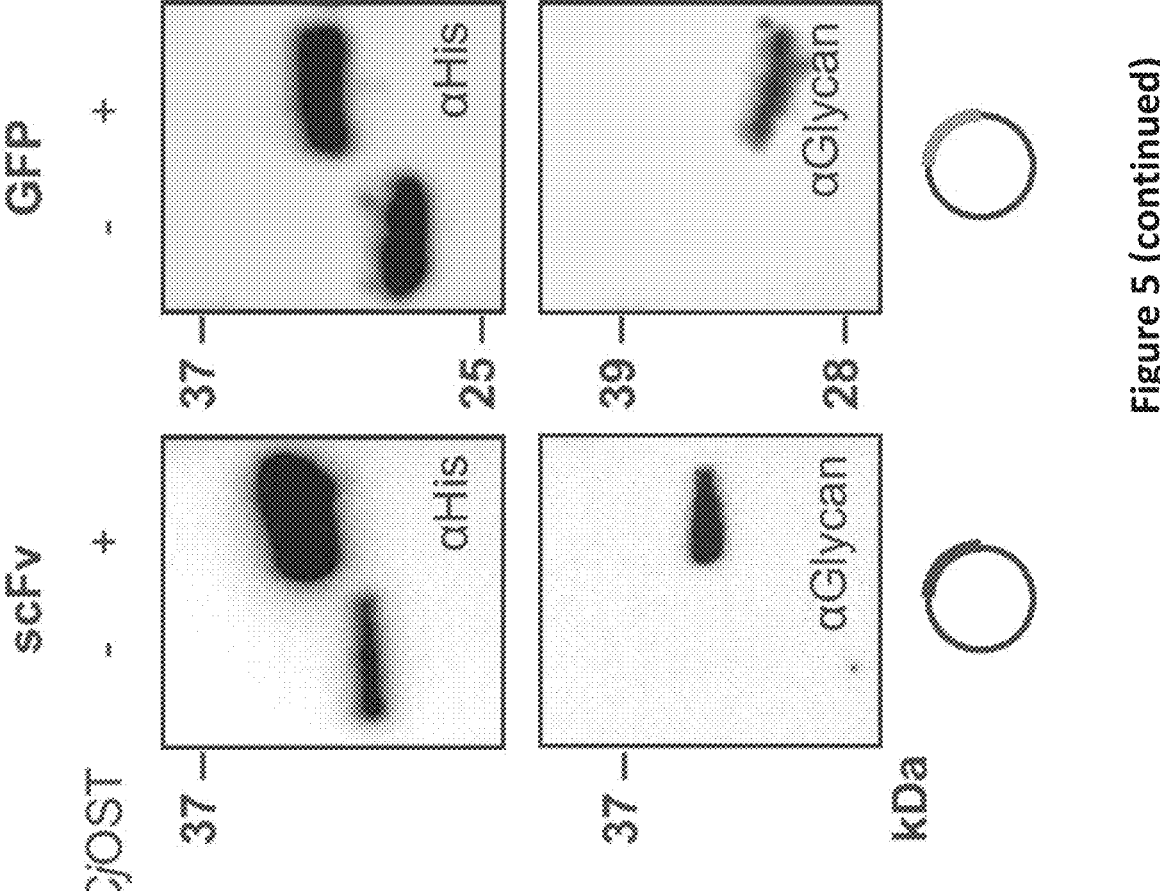
Figure 6:
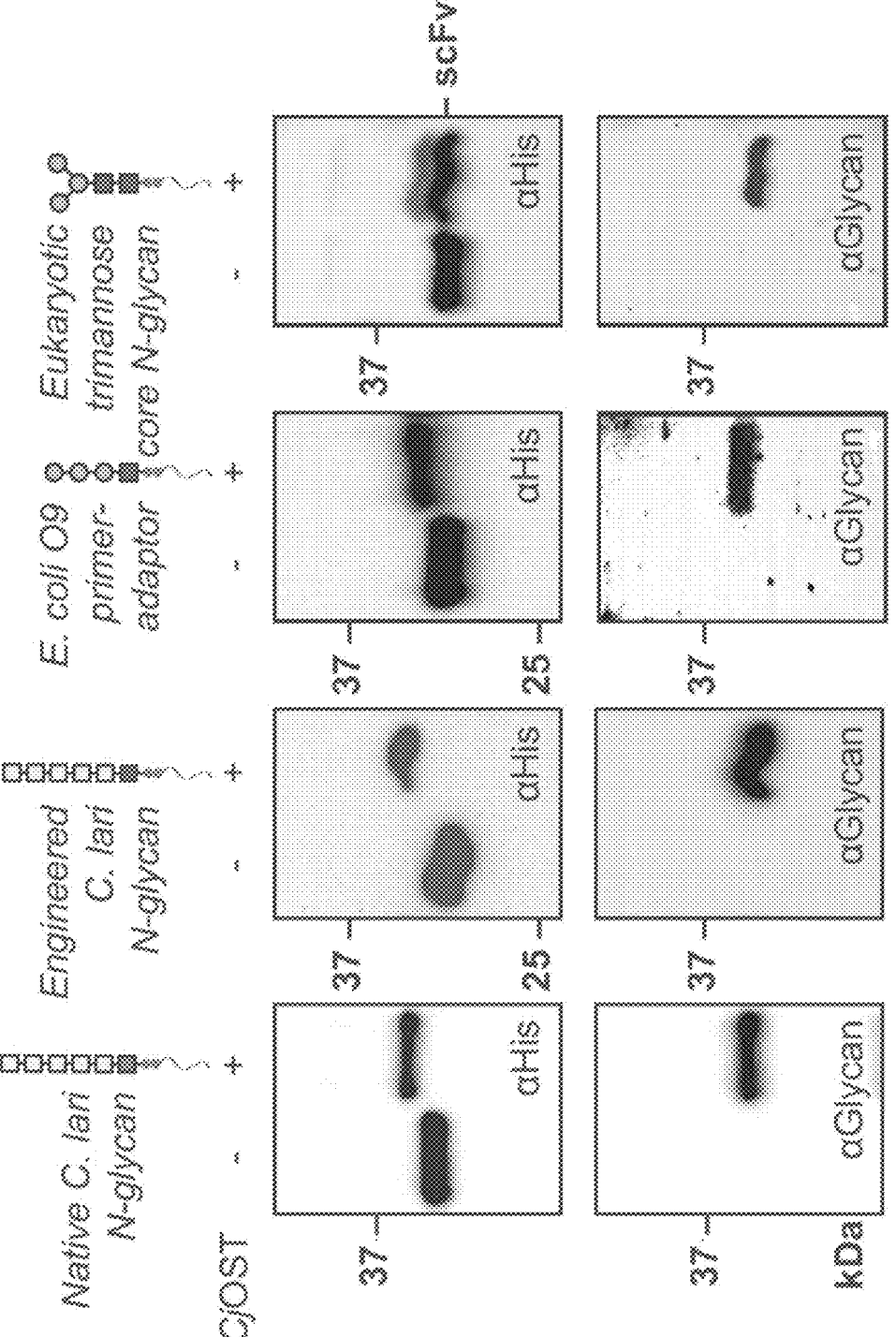
FIG. 6. Western blot illustrating that proteins such as a single chain antibody variable fragment (scFv) can be glycosylated with bacterial and eukaryotic glycans using a cell-free glycoprotein synthesis (CFGpS) platform.

FIG. 5 illustrates that crude *E. coli* lysates can be enriched with glycosylation components via overexpression in the source strain for lysate production. A CjLLO plasmid which expresses *Campylobacter jejuni* lipid-linked oligosaccharides (LLO) and CjOST plasmid which expresses *Campylobacter jejuni* oligosaccharide transfersase (OST) were introduced into a source strain to provide a cell lysate enriched in LLO and OST. (See FIG. 5A). An acceptor plasmid expressing an acceptor polypeptide for glycosylation was introduced into a cell-free glycoprotein synthesis (CFGpS) reaction mixture comprising the cell lysate to prepare a glycosylated acceptor polypeptide. (See FIG. 5A). FIG. 5B illustrates that a glycosylated single chain antibody variable fragment (scFv) and a glycosylated green fluorescent protein (GFP) were synthesized in the CFGpS reaction mixture. Similarly, FIG. 6 illustrates that proteins such as a single chain antibody variable fragment (scFv) can be glycosylated with bacterial and eukaryotic glycans using a cell-free glycoprotein synthesis (CFGpS) platform.

Figure 7:
FIG. 7. Four proteins approved by the US Food and Drug Administration (FDA) as adjuvant carriers for glycan antigens including *Neisseria meningitides* outer membrane protein (PorA), Tetanus toxoid of *Clostridium tetani*, Diptheria toxoid of *Corynebacterium diptheriae*, Non-typeable *Haemophilus influenzae* derived protein D (hpd).
Figure 7:

Regarding glycan antigens, protein carriers typically are utilized to for displaying the glycan antigens. Four proteins have been approved by the US Food and Drug Administration (FDA) as adjuvant carriers for glycan antigens. These include *Neisseria meningitides* outer membrane protein (PorA), Tetanus toxoid of *Clostridium tetani*, Diptheria toxoid of *Corynebacterium diptheriae*, Non-typeable *Haemophilus influenzae* derived protein D (hpd). (See FIG. 7).

Figure 8:
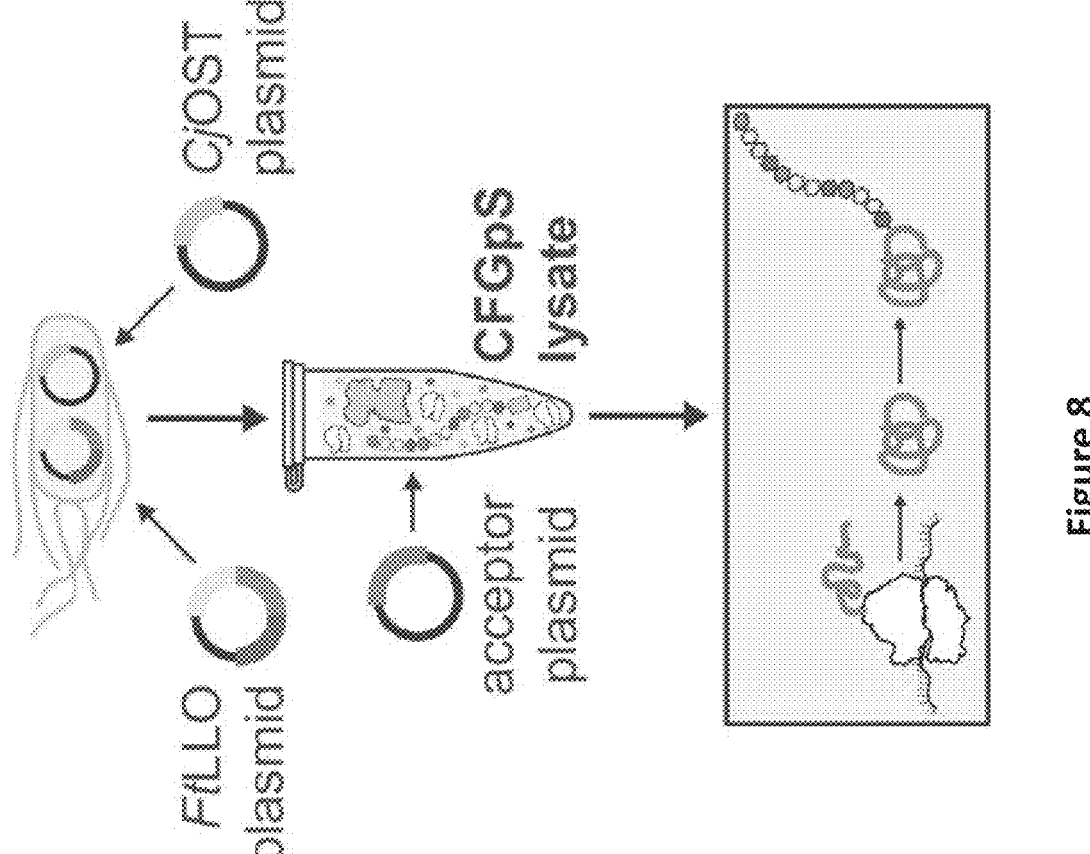
FIG. 8. Protein carriers can be glycosylated with *Franciscella tularensis* O antigen. (A) Crude *E. coli* lysates can be enriched with glycosylation components via overexpression in the source strain for lysate production. FtLLO plasmid which expresses *Franciscella tularensis* lipid-linked oligosaccharides (LLO) including glycans forming the *Franciscella tularensis* O antigen, and CjOST plasmid which expresses *Campylobacter jejuni* oligosaccharide transfersase (OST) are introduced into a source strain to provide a cell lysate enriched in LLO and OST. An acceptor plasmid expressing an FDA-approved protein carrier is introduced into a cell-free glycoprotein synthesis (CFGpS) reaction mixture comprising the cell lysate to prepare a glycosylated protein carrier. (B) Western blot of glycosylated carrier proteins (PD, PorA, CRM197, TTlight) probed with anti-histidine antibody ($\alpha$-His) or anti-*Franciscella tularensis* O polysaccharide antibody ($\alpha$-Ft O-PS).
Figure 8:
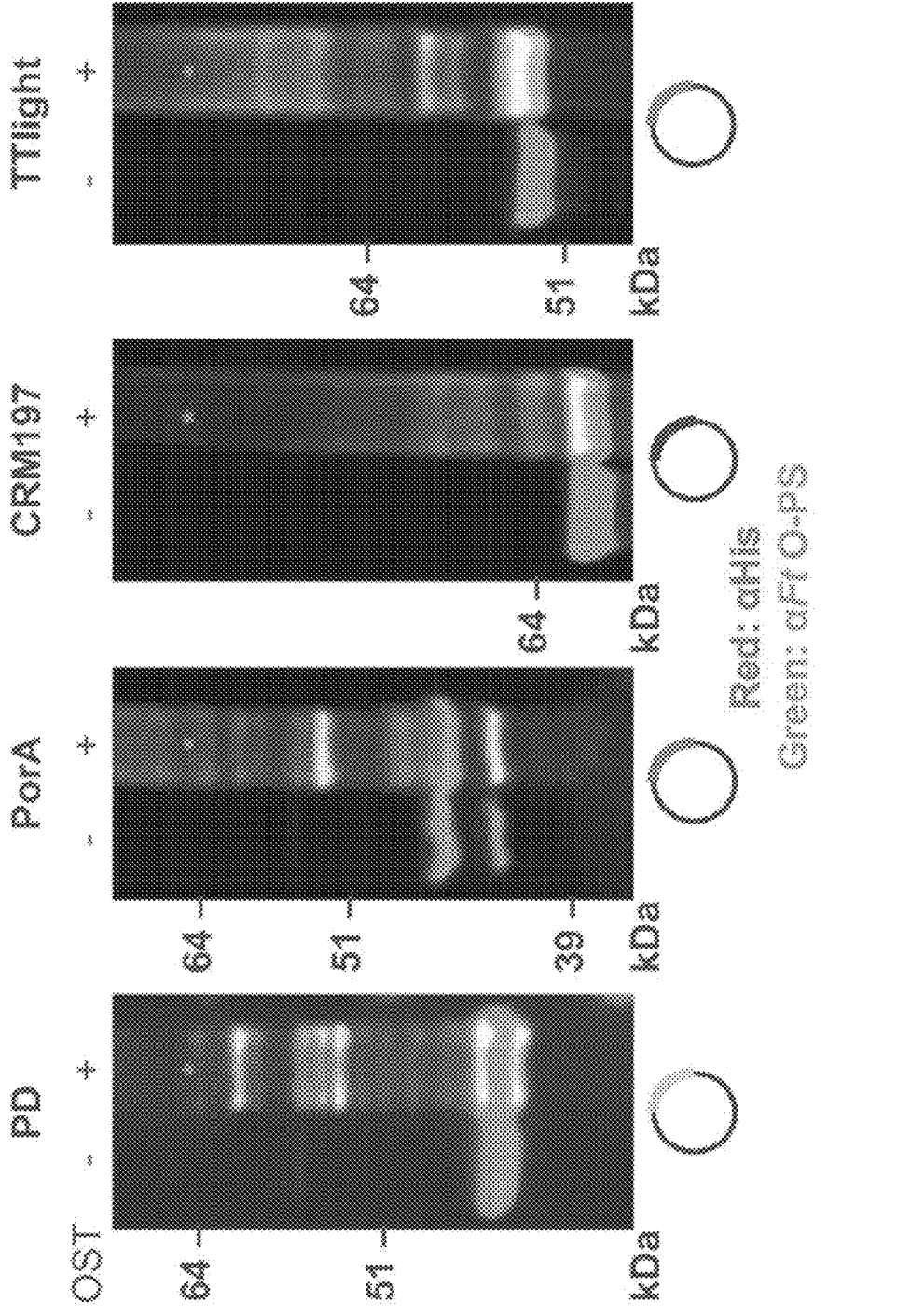

FIG. 8 illustrates that protein carriers can be synthesized and glycosylated with *Franciscella tularensis* O antigen in vitro using cell-free glycoprotein synthesis platforms. Crude *E. coli* lysates can be enriched with glycosylation components via overexpression in the source strain for lysate production. FtLLO plasmid which expresses *Franciscella tularensis* lipid-linked oligosaccharides (LLO) including glycans forming the *Franciscella tularensis* O antigen, and CjOST plasmid which expresses *Campylobacter jejuni* oligosaccharide transfersase (OST) were introduced into a source strain to provide a cell lysate enriched in LLO and OST. (See FIG. 8A). An acceptor plasmid expressing an FDA-approved protein carrier was introduced into a cell-free glycoprotein synthesis (CFGpS) reaction mixture comprising the cell lysate to prepare a glycosylated protein carrier. (See FIG. 8A). FIG. 8B illustrates that carrier proteins (PD, PorA, CRM197, TTlight can be synthesized and glycosylated with *Francisella tularensis* O polysaccharide antibody in vitro using a cell-free glycoprotein synthesis (CFGpS) platform.

Figure 9:
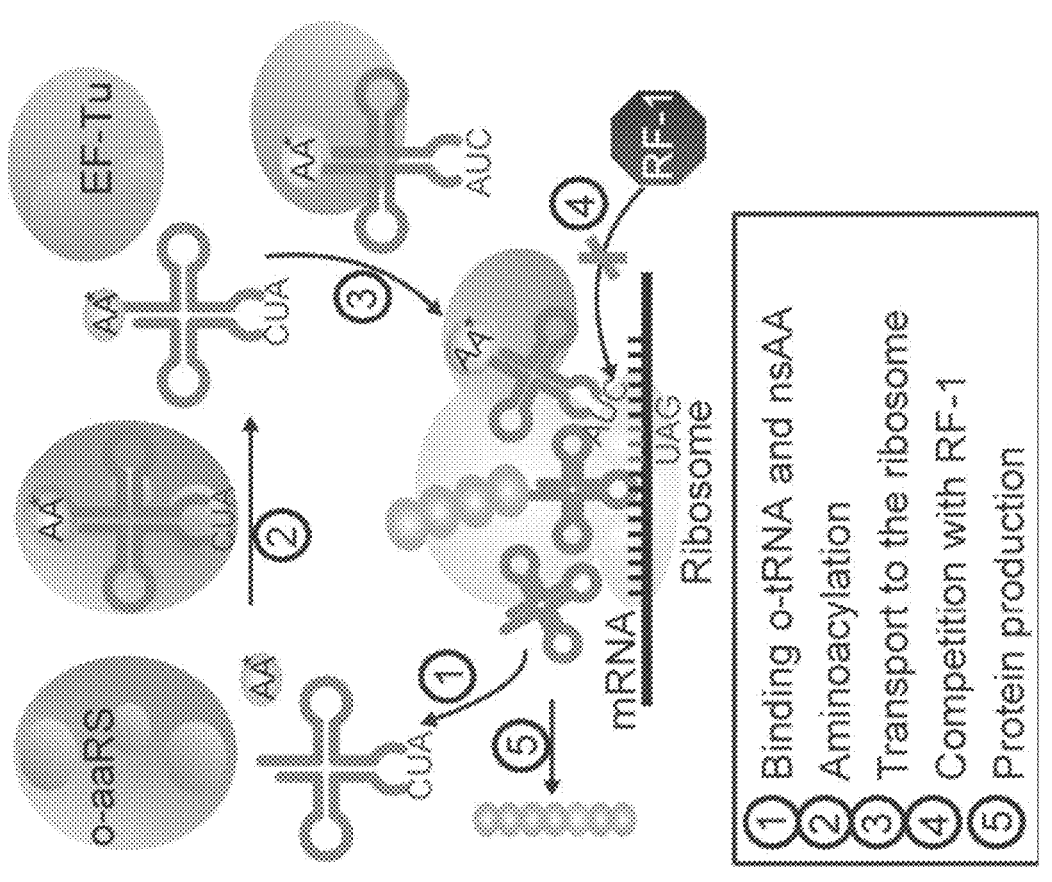
FIG. 9. Schematic illustration of the use of amber suppression in a release factor 1 (RF-1) deficient strain to incorporate a non-standard amino acid (nsAA). (See Perez, Stark, and Jewett, Cold Spring Harbor Perspect. Biol. (2016), December 1; 8(12). pii: a023853. doi: 10.1101/cshperspect.a023853). Orthogonal transfer RNA (o-tRNA) comprising the AUC anti-codon is charged with the nsAA via an orthogonal aminoacyl-tRNA synthetase (o-aaRS). Elongation factor thermos unstable (EF-Tu) then facilitates the selection and binding of the charged o-tRNA to the A-site of the ribosome and the nsAA is incorporated in the nascent peptide chain at the position of the amber (UAG) codon. Because the strain is RF-1 deficient, translation is not terminated at the amber codon.

Cell-free protein synthesis platforms can be configured to incorporate non-standard amino acids. For example, FIG. 9 provides a schematic illustration of the use of amber suppression in a release factor 1 (RF-1) deficient strain to incorporate a non-standard amino acid (nsAA). (See Perez, Stark, and Jewett, Cold Spring Harbor Perspect. Biol. (2016), December 1; 8(12). pii: a023853. doi: 10.1101/cshperspect.a023853, the content of which is incorporated herein by reference in its entirety). As illustarated in FIG. 9, an orthogonal transfer RNA (o-tRNA) comprising the AUC anti-codon can be charged with a nsAA via an orthogonal aminoacyl-tRNA synthetase (o-aaRS). Elongation factor thermo unstable (EF-Tu) then facilitates the selection and binding of the charged o-tRNA to the A-site of the ribosome and the nsAA is incorporated in the nascent peptide chain at the position of the amber (UAG) codon. Because the strain is RF-1 deficient, translation is not terminated at the amber codon via competition between RF-1 and the EF-Tu/tRNA complex.

Figure 10:
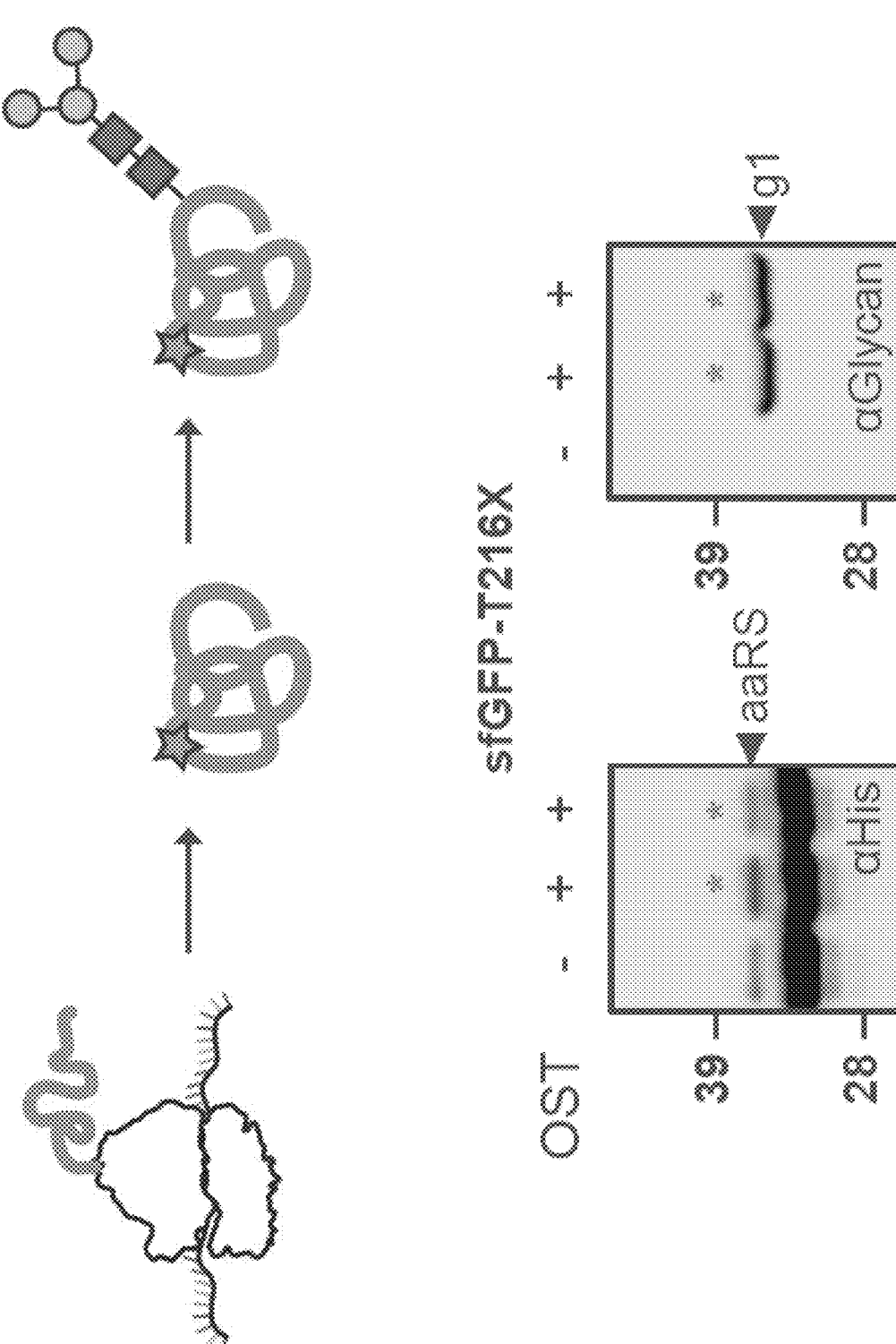
FIG. 10. (Top) Illustration of combined incorporation of a non-standard amino acid (symbolized by star) and glycan (symbolized by structure of squares and circles) into a protein chain. (Bottom) Western blot of protein having an incorporated non-standard amino acid (nsAA) and glycosylation probed with anti-His antibody ($\alpha$-His) or anti-glycan antibody (α-Glycan). aaRS designates the molecule weight of protein chain having incorporated nsAA.

As contemplated herein, incorporation of a non-standard amino acid (nsAA) into a nascent protein and glycosylation of the nascent protein can be combined in a cell-free glycoprotein synthesis (CFGpS) platform. FIG. 10 (top) schematically illustrates combined incorporation of a non-standard amino acid and glycan into a protein chain. The sfGFP-T216X protein was synthesized in vitro and the nsAA para-azido-phenylalanine was incorporated into the protein. (See FIG. 10 (bottom left panel). Additionally, the sfGFP-T216X protein was glycosylated in vitro. (See FIG. 10 (bottom right panel).

Figure 11:
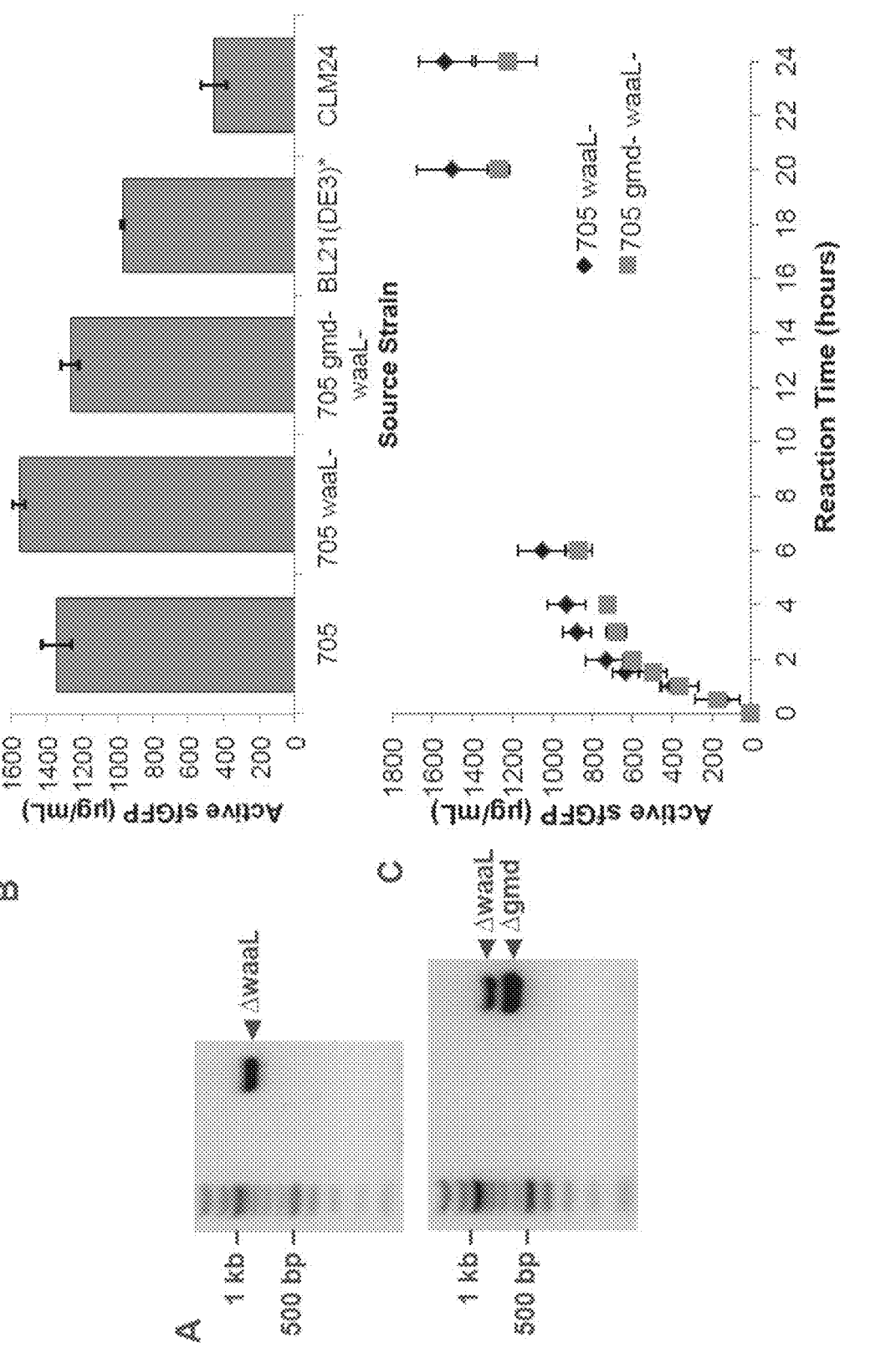
FIG. 11. Derivatives of the *E. coli* 705 strain were created that were deficient in waaL or deficient in both of waaL and gmd. (A) Analysis confirming ΔwaaL deletion and combination of ΔwaaL and Δgmd deletions in 705 strain. (B) Active sfGFP produced in cell-free protein synthesis (CFPS) reactions using cell lysates from the indicated strains. (C) Active sfGFP produced versus time in CFPS reactions using cell lysates from the 705ΔwaaL strain and the 705ΔgmdΔwaaL strain.

In order to create improved cell lysates for CFGpS, the *E. coli* strain was engineered to be deficient in in waaL or deficient in both of waaL and gmd. (See FIG. 11A). The *E. coli* waaL protein is associated with endogenous lipopolysaccharide synthesis and the *E. coli* gmd protein is a GDP-mannose 4,6-dehydratase associated with endogenous glycan synthesis. Therefore, a strain that is deficient in in waaL or deficient in both of waaL and gmd should produce a lysate having reduced components that would compete or interfere with orthogonal glycosylation. We observed that cell lysates from the 705ΔwaaL strain and the 705ΔgmdΔwaaL strain were efficient in CFGpS platforms. (See FIGS. 11A and 11B).

Figure 12:
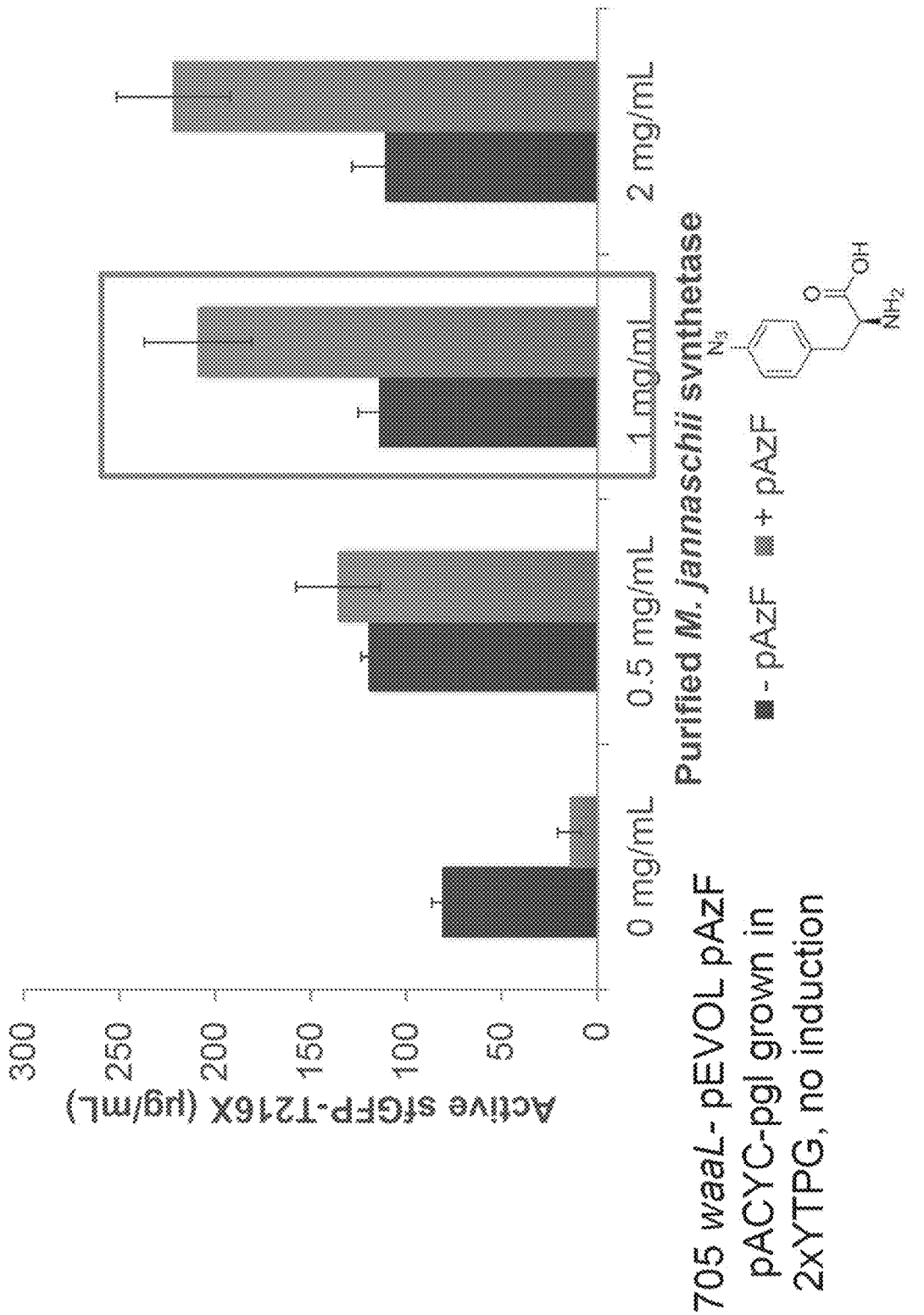
FIG. 12. Incorporation of para-azido-phenylaline (pAzF) into the sfGFP T216X protein via cell-free protein synthesis. A cell-free extract was prepare from the 705ΔwaaL strain and a purified orthogonal amino-acyl tRNA synthetase (aaRS) from *Methanococcus jannaschii* was added at increasing amounts to prepare CFPS reaction mixtures.

Using a cell lysate from the 705ΔwaaL strain we incorporated the non-standard amino acid (nsAA) para-azido-phenylaline (pAzF) into the sfGFP T216X protein via cell-free protein synthesis. (See FIG. 12). A cell-free extract was prepare from the 705ΔwaaL strain and a purified orthogonal amino-acyl tRNA synthetase (aaRS) from *Methanococcus jannaschii* was added at increasing amounts to prepare CFPS reaction mixtures.

Figure 13:
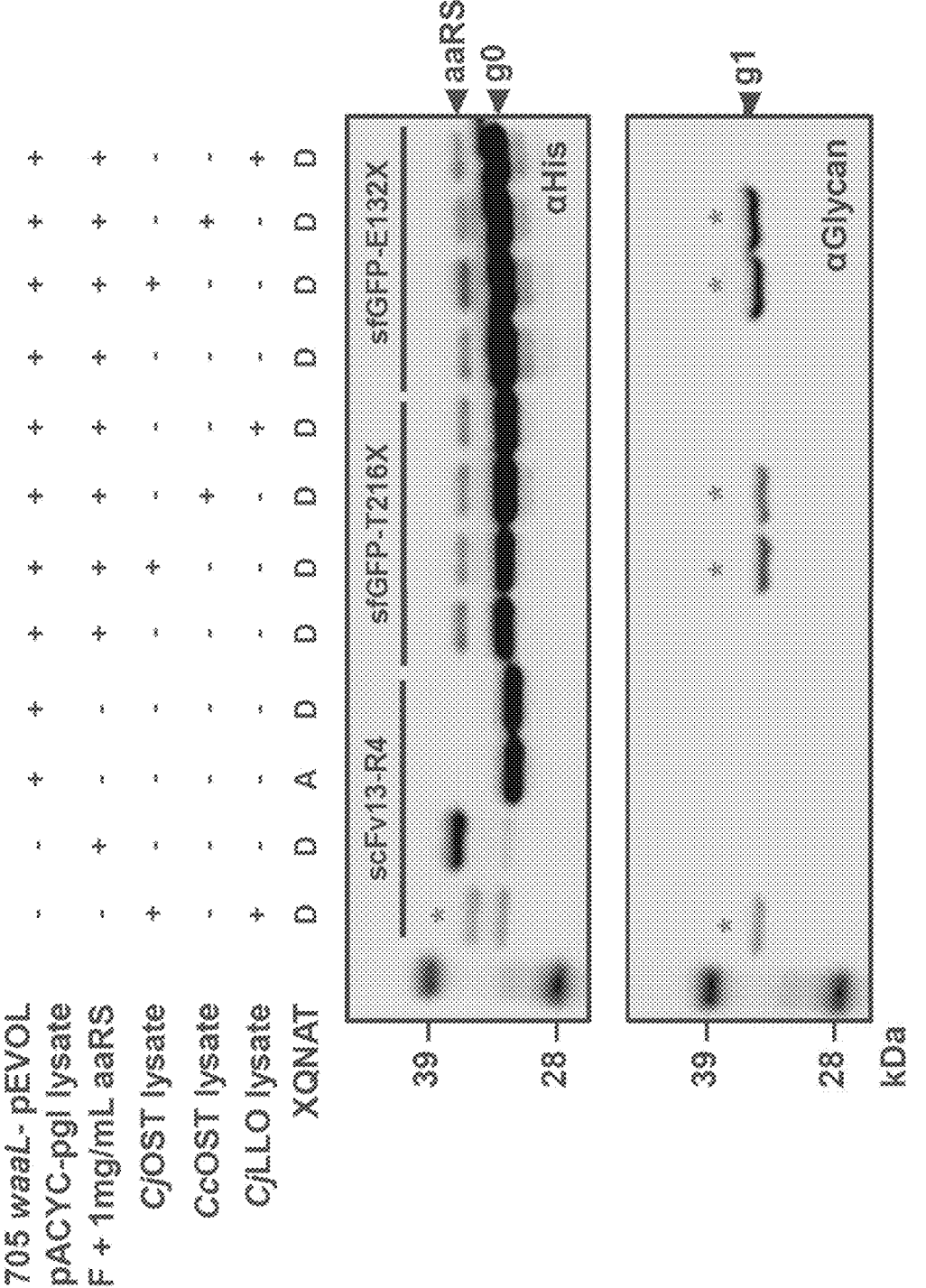
FIG. 13. Western blot illustrating coordinated amber suppression and glycosylation in cell-free glycoprotein synthesis (CFGpS) of test proteins (scFV13-R4, sfGFP-T216X, and sfGFP-E132X). A cell-free extract was prepared from the 705ΔwaaL strain and test conditions included: addition of para-azido-phenylalanine and orthogonal amino-acyl tRNA synthetase; addition of a cell free lysate comprising the oligosaccharide transferase from *C. jejuni*; addition of a cell free lysate comprising the oligosaccharide transferase from *C. c*; addition of a cell free lysate comprising lipid-linked oligosaccharides from *C. jejuni*; and presence of the glycosylated sequon DQNAT or non-glycosylated variant AQNAT in the synthesized protein.

We next tested cell-free glycoprotein synthesis (CFGpS) of test proteins (scFV13-R4, sfGFP-T216X, and sfGFP-E132X) and incorporation of non-standard anino acid (nsAA) para-azido-phenylalanine (pAzF). (See FIG. 13). A cell-free extract was prepared from the 705ΔwaaL strain and test conditions included: addition of para-azido-phenylalanine pAzF and orthogonal amino-acyl tRNA synthetase; addition of a cell free lysate comprising the oligosaccharide transferase (OST) from *Campylobacter jejuni*; addition of a cell free lysate comprising the oligosaccharide transferase (OST) from *Campylobacter coli*; addition of a cell free lysate comprising lipid-linked oligosaccharides (LLO) from *Campylobacter jejuni*; and presence of the glycosylation sequon DQNAT or non-glycosylated variant AQNAT in the synthesized protein. The nsAA pAzF was incorporated into each of scFV13-R4, sfGFP-T216X, and sfGFP-E132X. In addition, sfGFP-T216X, and sfGFP-E132X were observed to be glycosylated. (See FIG. 13).

Example 3—Toward Engineering Designer Glycoproteins with Site-Specific Functionalization Handles, and Editable Glycans We generated glycoproteins that can be site-specifically labeled with user-specified ligands and glycosylation patterns. Toward building eukaryotic-like glycosylation, we developed a system that can be interfaced with bacterial glycosylation to site-specifically install the base glycan for eukaryotic N-linked glycosylation, which can be subsequently elaborated by glycosyltransferases to build glycans of choice on a target protein.

The benefits of site-specific labeling of glycoproteins are vast. For example, numerous molecular therapeutics are labeled with polyethylene glycol (PEG), as this modification has been attributed to boosts in stability and half life of molecular therapeutics. Additionally, conjugating chemotherapeutic or antibiotic drugs to antibodies has been shown to improve tumor or bacterial cell killing, respectively. Common protein labeling approaches, including the popular maleimide/cysteine and NHS-ester/lysine chemistries, have known drawbacks including incomplete labeling and batch-to-batch heterogeneity. Additionally, non-specific labeling techniques can often affect the structure and function of folded protein molecules in unexpected ways.

Figure 14:
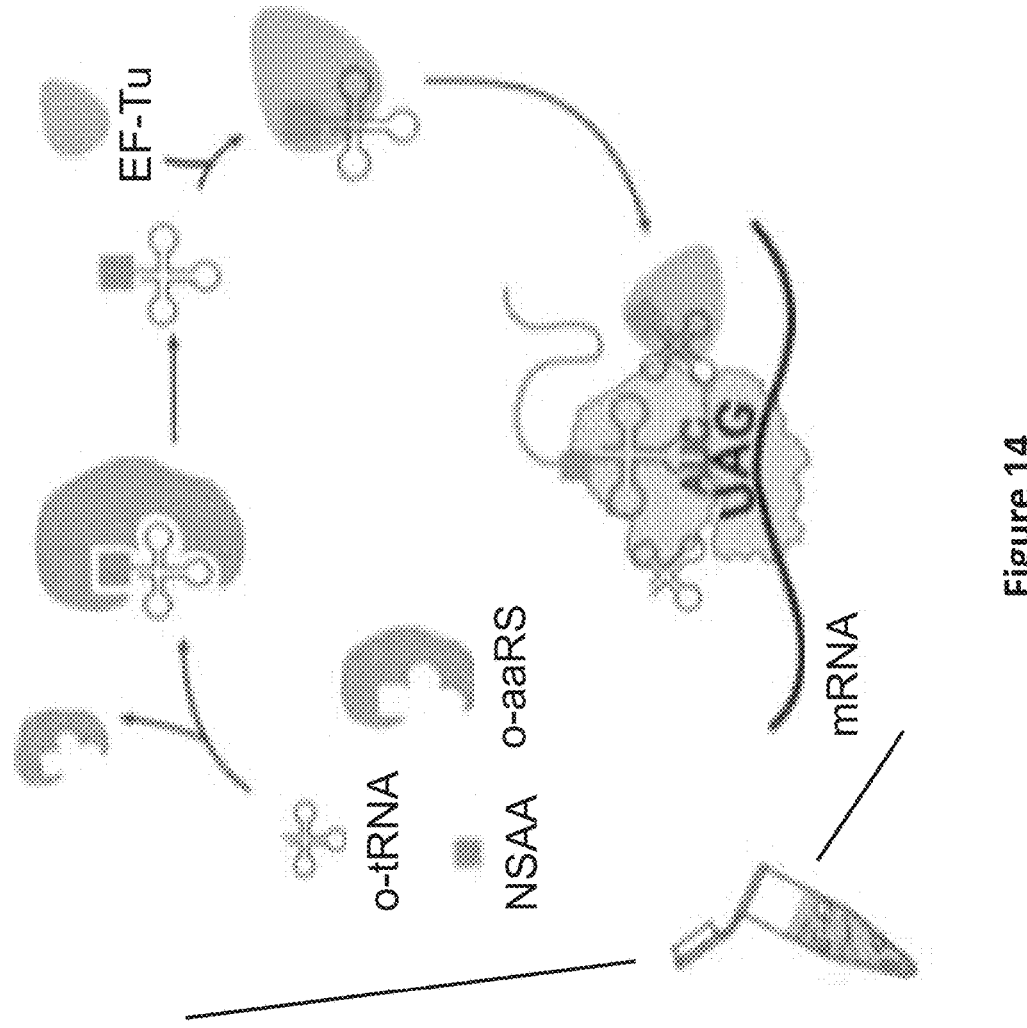
FIG. 14. Site-specific incorporation of a click-active ncAA into target protein using *E. coli* systems. (A) Schematic of the OTS used to site-specifically install ncAAs. (B) In-gel fluorescence image of SDS-PAGE gel demonstrating installation of the ncAA (para-azido-phenylalanine) into a 23 kDa target protein. Gel shows biorthogonal labeling of the target protein with a fluorophore via SPAAC.
Figure 14:
Figure 14:
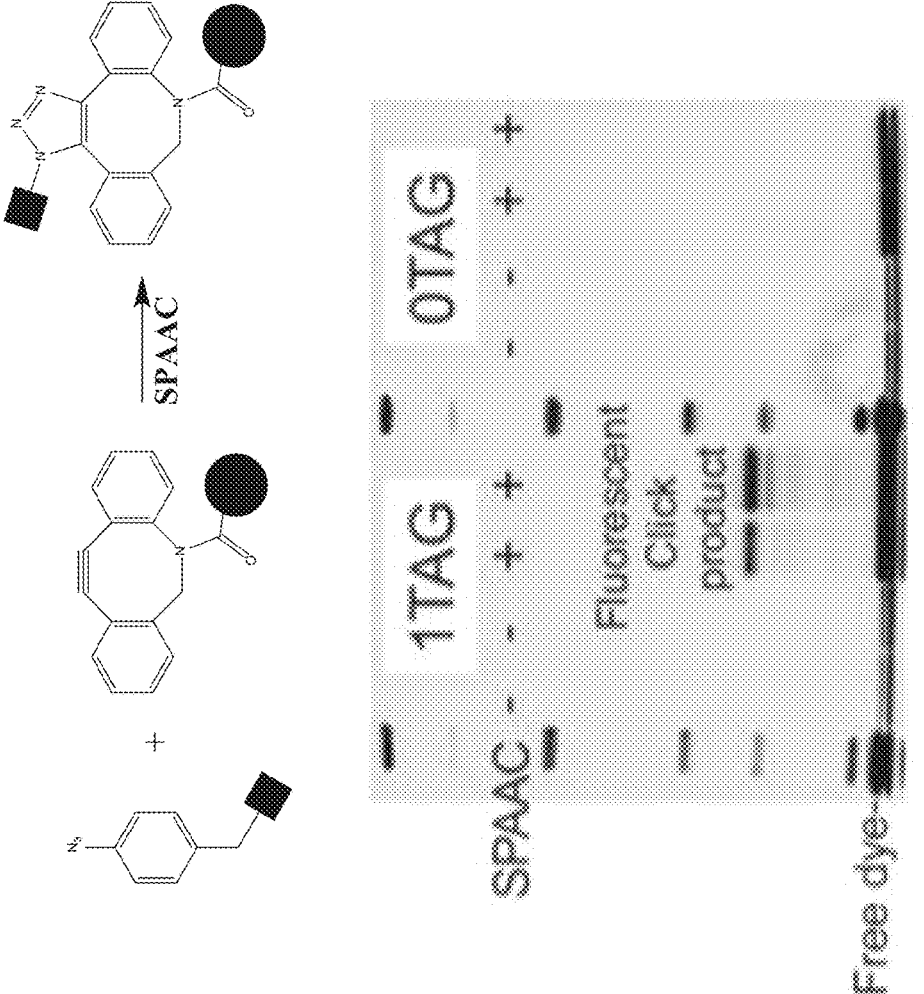

To address these issues, we developed a system for combined glycosylation and non-canonical amino acid (ncAA) incorporation that will enable site-specific labeling of glycoproteins via bio-orthogonal conjugation chemistries. Broadly, the site-specific incorporation of ncAAs is useful for increasing the chemical diversity of polypeptide substrates. This work leverages recent advances in synthetic biology which have led to the development of a suite of strains and orthogonal translation systems (OTSs) (FIG. 14A) that allow for ncAA incorporation (ncAAi), both inside of cells, and in cell-free, at high-fidelities and titers. This technique, termed amber suppression refers to the reassignment of a native E. coli stop codon for the desired ncAA. Specifically for this work, we have focused on incorporating the ncAA para-azido-phenylalanine (pAzF), which is a partner in the strain-promoted azide-alkyne cycloaddition (SPAAC) reaction (FIG. 14). This reaction is robust at a range of pH's and temperatures, and does not cross-react with any side groups found in the 20 canonical amino acids (FIG. 14B).

Figure 15:
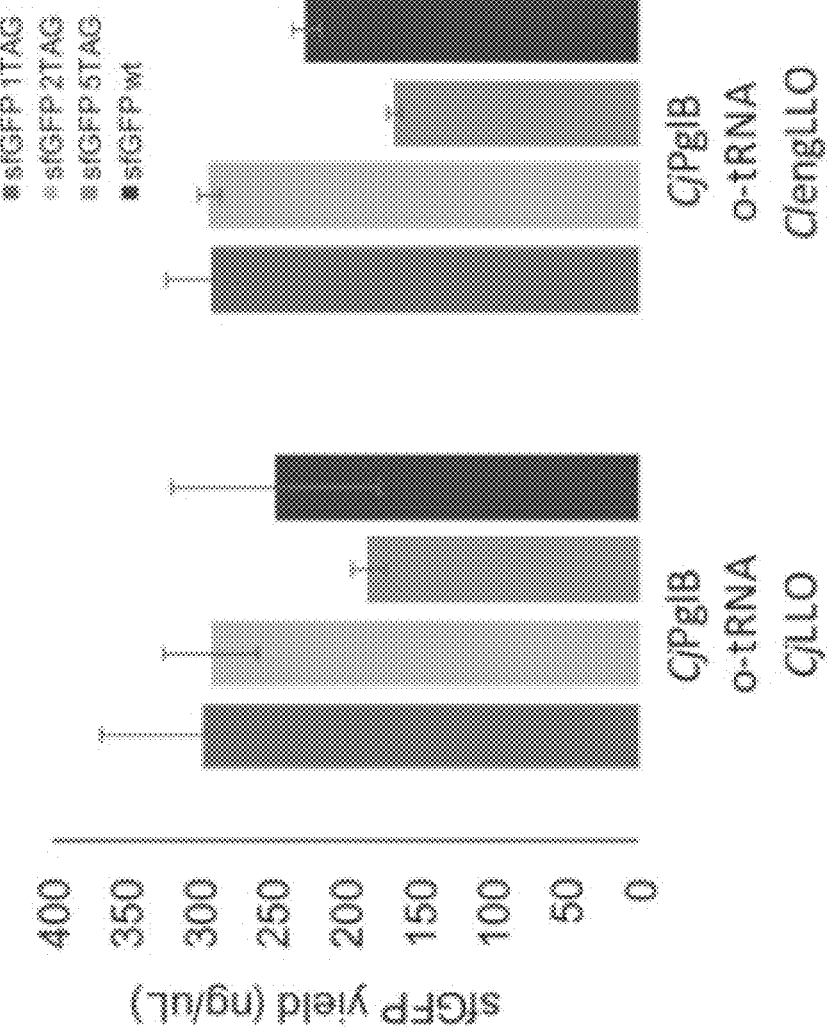
FIG. 15. CFGpS lysates enriched with o-tRNA are active for ncAA incorporation and for efficient glycosylation (A) CFPS yields of sfGFP encoded by plasmids containing 0, 1, 2, or 5 amber stop codons in CFGpS lysates enriched with bacterial LLO variants and containing all components of the pAzF-OTS (B) Lysates containing amber suppression and glycosylation machinery efficiently, glycosylate a model protein construct (sfGFP with C-terminal sequon fusions for DQNAT and AQNAT). Glycosylation is confirmed by an anti-6×His western blot against the target glycoprotein, and checked for cross-reactivity with an anti-glycan serum (α-glycan).
Figure 15:
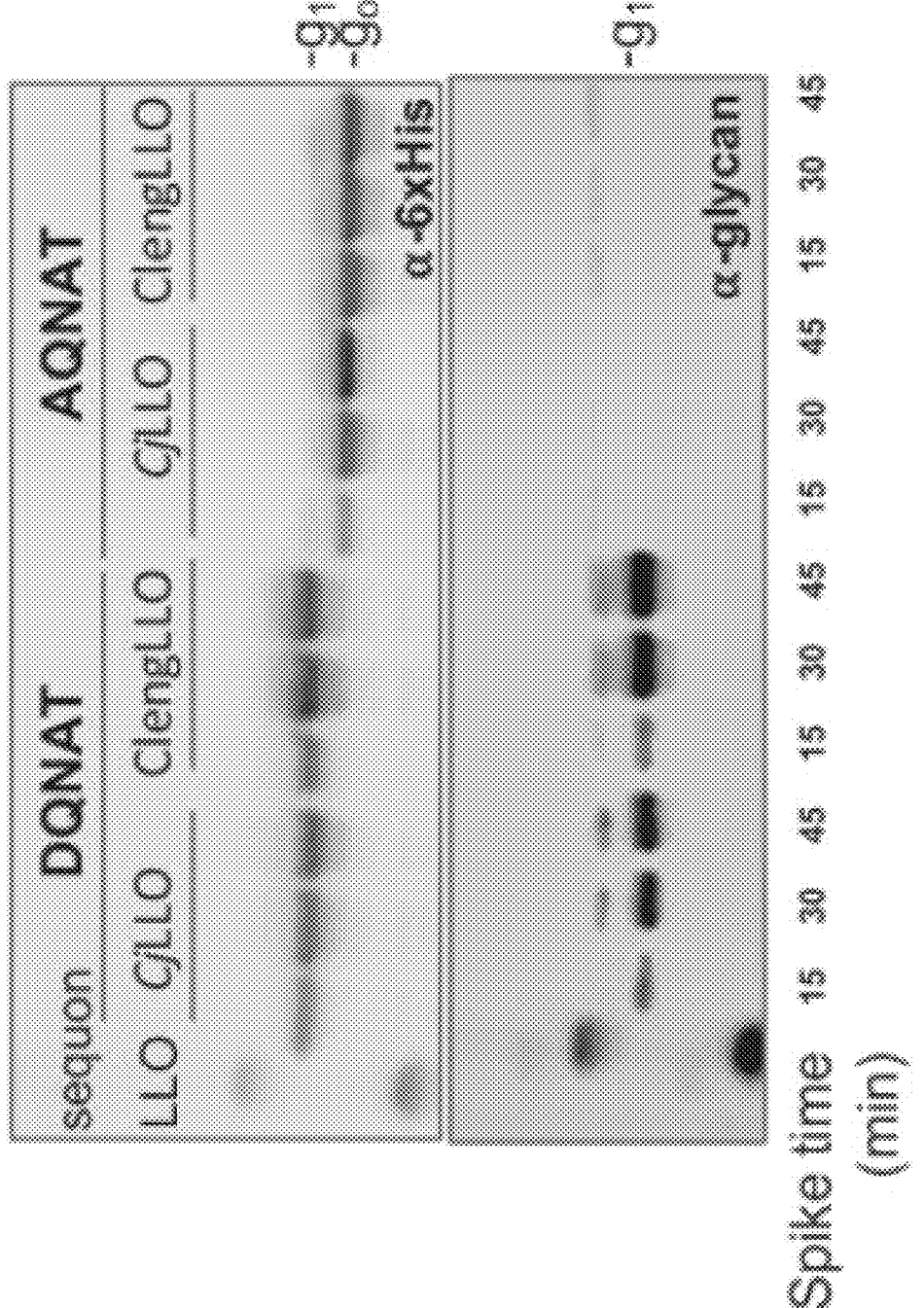

We prepared CFGpS lysates using a chassis strain of E. coli that has been genomically recoded for optimized glycosylation and amber suppression (strain 705 ΔwaaL). Lysates were prepared from cells overexpressing the CjPglB enzyme and orthogonal pAzF tRNA (o-tRNA) with either CjLLO or ClengLLO (FIG. 15). To test for ncAAi, we supplied template plasmids encoding sfGFP, bearing 0, 1, 3, or 5 amber codons. In both lysates, we observed production of sfGFP containing pAzF (FIG. 15A). These lysates were then tested for glycosylation activity at three different spike times, to test glycosylation efficiency over time as more protein is synthesized (FIG. 15B). In both cases, we observed ~100% glycosylation efficiency under all conditions tested.

Figure 16:
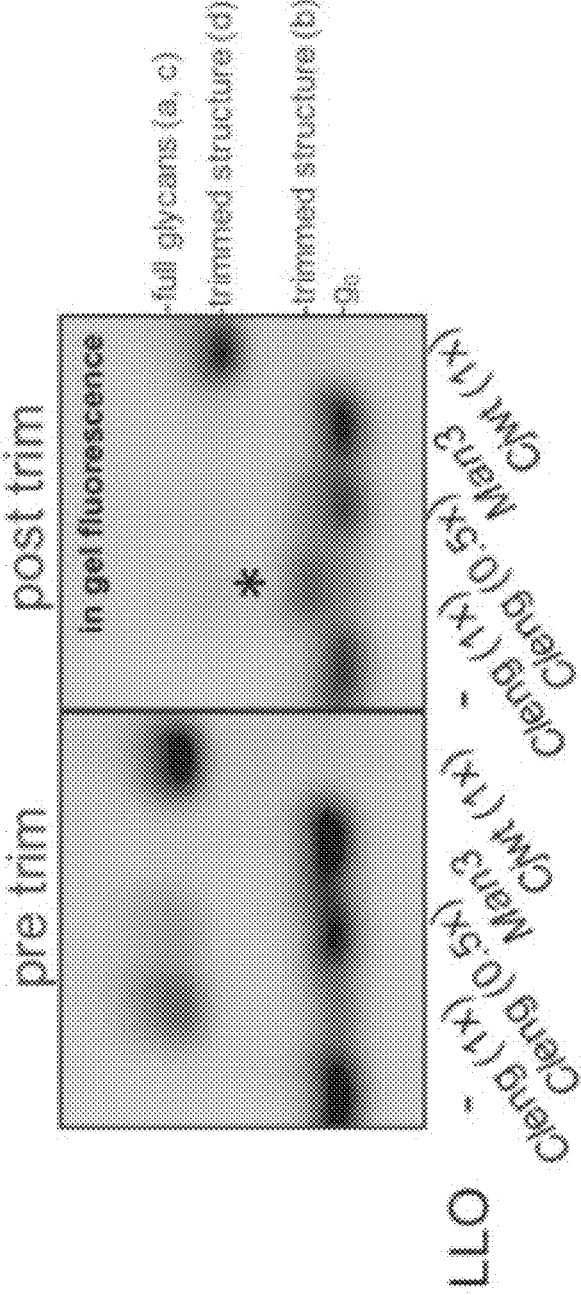
FIG. 16. Glycan trimming with N-acetylgalactosaminidase enzyme on polypeptide substrates allows for further customization of target glycoproteins bearing engineered bacterial glycans. (A) In-gel florescence of a FITC-labeled polypeptide substrate bearing a DQNAT sequon under various glycosylation and trimming reaction conditions. Left-hand panel shows mobility shifts corresponding with full glycans, and right-hand panel shows the resulting mobility shifts for trimmed polypeptides. X-labels show the glycans used for in-vitro glycosylation, with dilution factors in parenthesis if appropriate. (B) Glycan structures pre- and post-trimming with N-acetylgalactosaminidase, where (a) and (c) correspond with full glycans, and (b) and (d) correspond with trimmed structures.
Figure 16:
Figure 16:
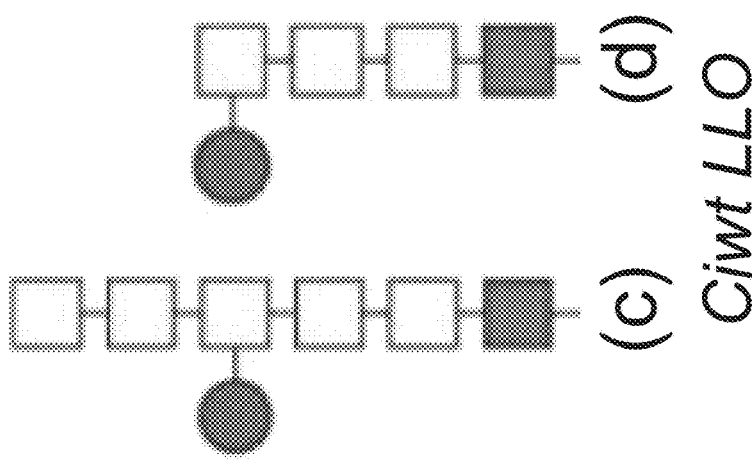
Figure 16:
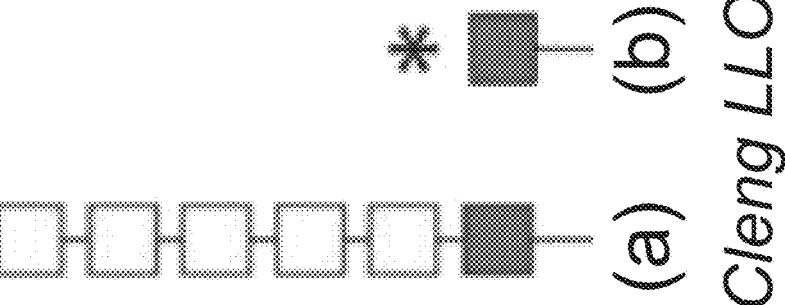

We also developed methods for tailoring glycan structures on polypeptide substrates using enzymes to produce glyco-proteins that are modified with a single GlcNAc for further elaboration (FIG. 16). Briefly, several glycosylated polypeptides were incubated with an enzyme that trims through poly GalNAc residues, run on a denaturing peptide gel, then imaged vial in-gel florescence of an N-terminal fluorophore. The mass shift of these peptides indicates that efficient trimming was achieved, leaving behind a truncated pentasaccharide when the substrate is glycosylated with a C. jejuni glycan, and a single GlcNAc residue when the glycan substrate is a linear glycan from C. lari (containing GlcNAc at the reducing end). These results have been confirmed by MALDI-MS. See FIG. 16B for expected oligosaccharide structures pre- and post-glycan trimming. In future work, we plan to combine our novel methods for ncAAi, glycan trimming, and in vitro glycan building to produce therapeutic proteins bearing eukaryotic-like glycan structures and containing bio-orthogonal amino acids for site-specific chemical labeling.

Figure 17:
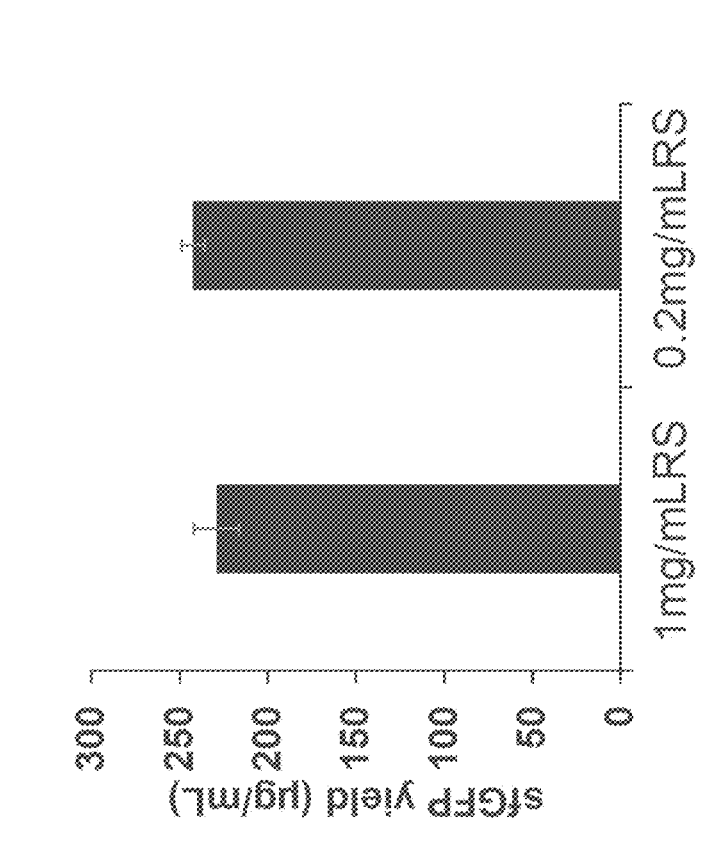
FIG. 17. Analysis of pAzF-incorporation in a cell-free glycoprotein synthesis (CFGpS) system. (A) Echo optimization (ACH). Background levels of incorporation in a CFGpS system were measured by adding increasing amounts of pAzF and pAzF-FS. (B) Scaled-up CFGpS and purification. CFGpS reactions were performed at two different concentrations of aaRS. Purification yields were 13.6 μM and 15.4 μM from 200 μl reaction volumes.

We also analyzed pAzF-incorporation in a cell-free glycoprotein synthesis (CFGpS) system. First, we determined optimum concentrations of pAzF and pAzF-FS and measured background levels of incorporation in a CFGpS system by adding increasing amounts of pAzF and pAzF-FS. (See FIG. 17). We next scaled-up CFGpS and purification. CFGpS reactions were performed at two different concentrations of aaRS, and purification yields were 13.6 μM and 15.4 μM from 200 μl reaction volumes. (See FIG. 17).

Figure 18:
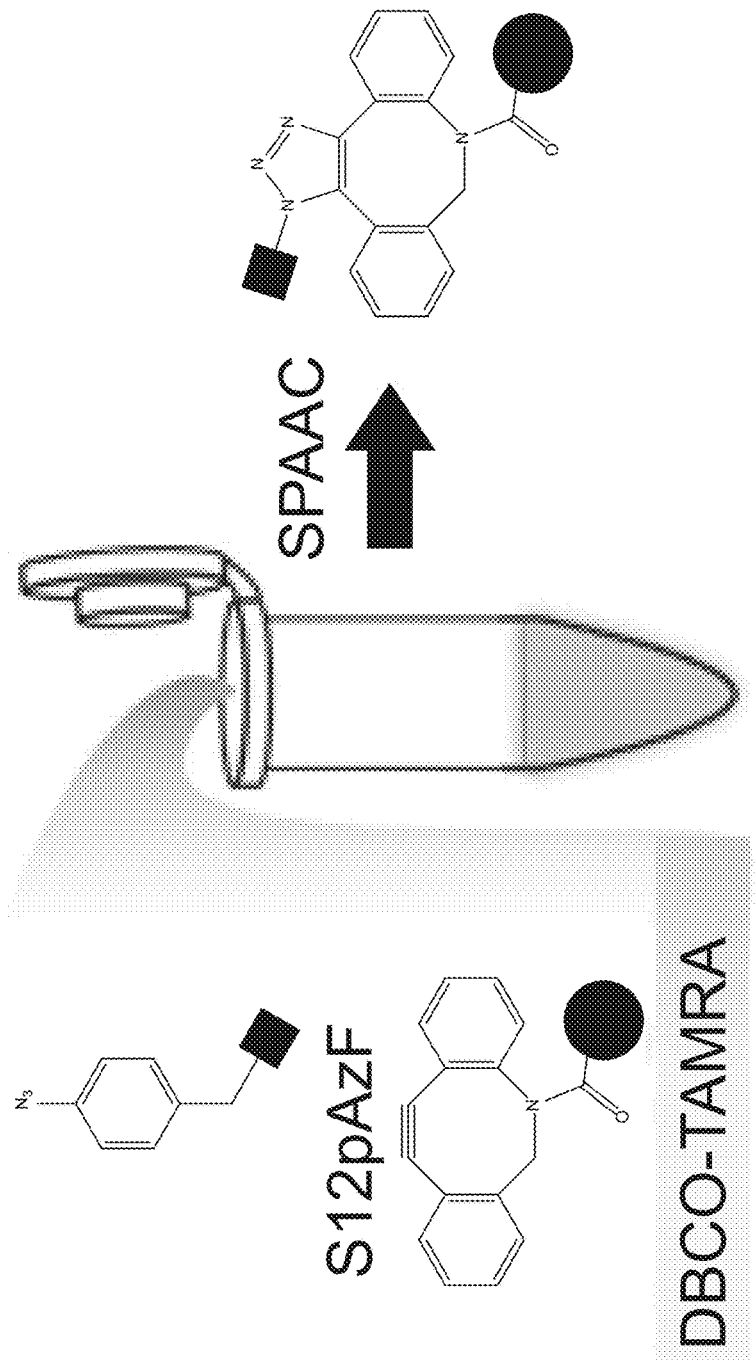
FIG. 18. Cell-free glycoprotein synthesis (CFGpS) combined with strain-promoted alkyne-azide cycloadditions (SPAAC) to conjugate a fluorophore to pAzF incorporated into a synthesized amino acid polymer. (A) Schematic of CFGpS and click chemistry using a TAMRA-labeled dibenzocyclooctyne compound. (B) and (C) SDS-PAGE analysis of purified, clicked products indicates full conversion of pAzF-incorporated acceptor protein. (B) Coomasie Bright Blue stained (total protein). (C) In-gel fluorescence (detection of fluor).
Figure 18:
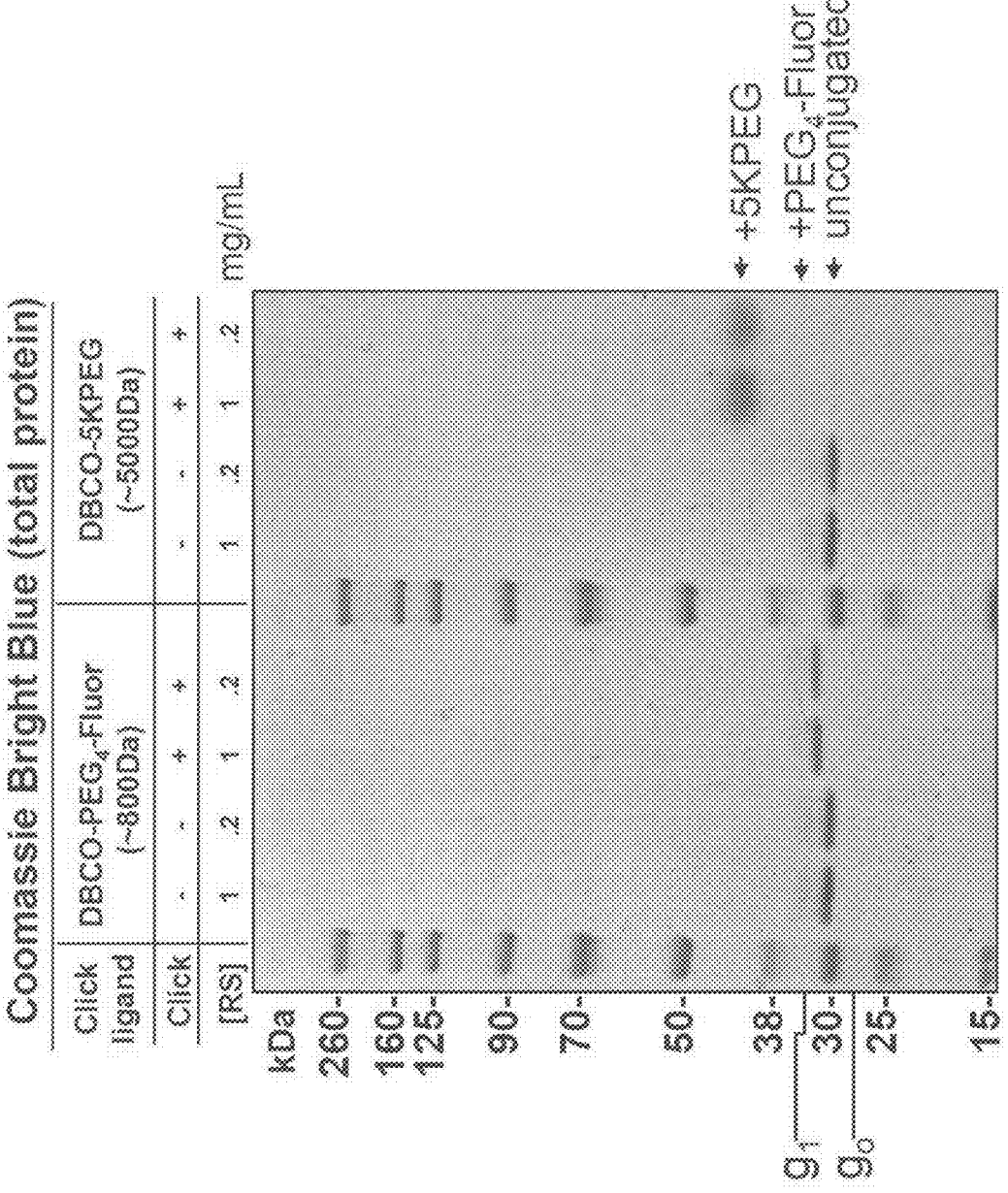
Figure 18:
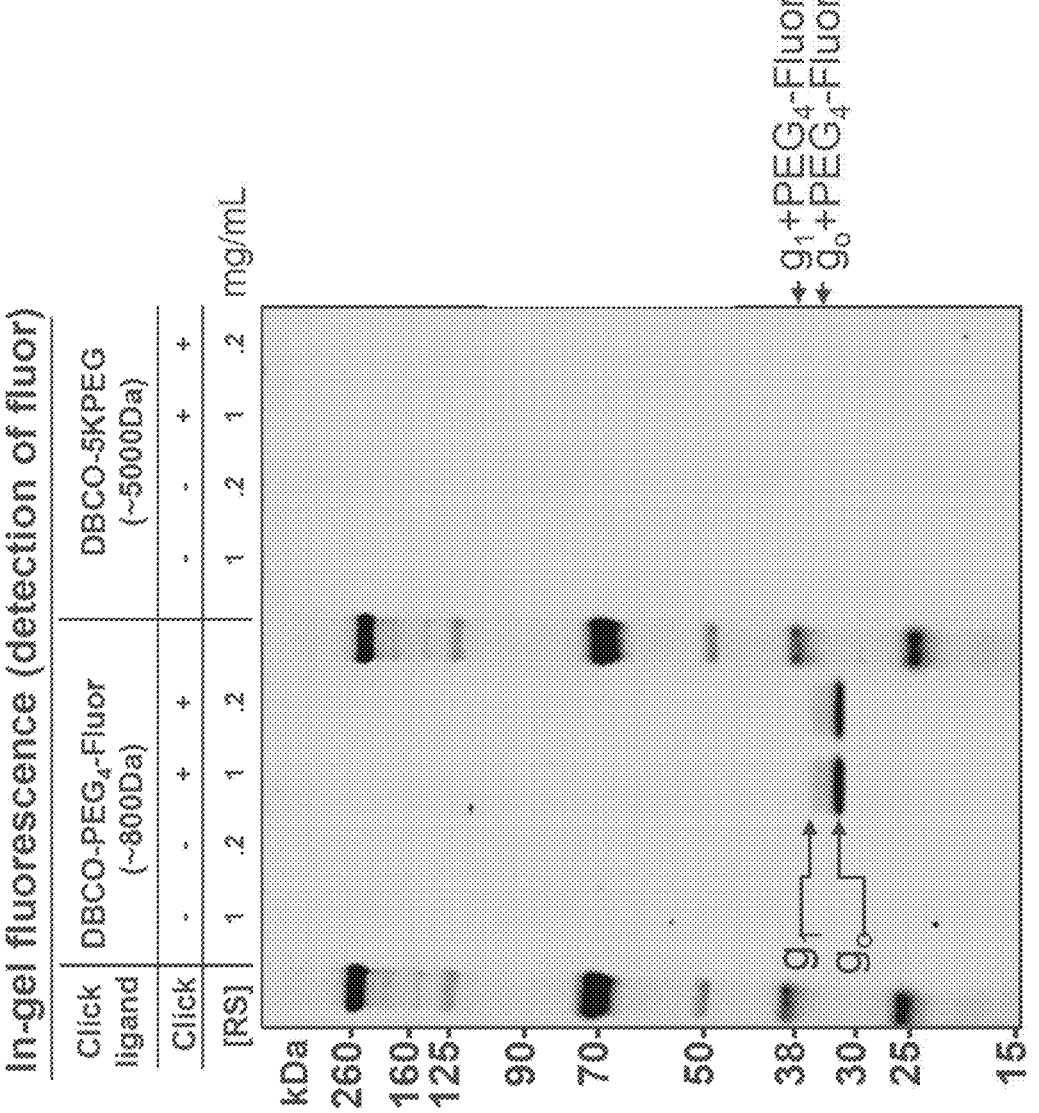

Finally, we performed cell-free glycoprotein synthesis (CFGpS) combined with strain-promoted alkyne-azide cycloadditions (SPAAC) to conjugate a fluorophore to pAzF incorporated into a synthesized amino acid polymer. (See FIG. 18). SDS-PAGE analysis of purified, clicked products indicated full conversion of pAzF-incorporated acceptor protein to fluorophore-labeled product. (See FIG. 18).

REFERENCES

1. Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
2. Jewett, M. C. & Swartz, J. R. Mimicking the Escherichia coli cytoplasmic environment activates long-lived and efficient cell-free protein synthesis. Biotechnology and bioengineering 86, 19-26, doi:10.1002/bit.20026 (2004).
3. Caschera, F. & Noireaux, V. Synthesis of 2.3 mg/ml of protein with an all Escherichia coli cell-free transcription-translation system. Biochimie 99, 162-168, doi:10.1016/j.biochi.2013.11.025 (2014).
4. Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).
5. Hong, S. H. et al. Improving Cell-Free Protein Synthesis through Genome Engineering of Escherichia coli Lacking Release Factor 1. Chembiochem: a European journal of chemical biology, doi:10.1002/cbic.201402708 (2015).
6. Yang, W. C. et al. Cell-free production of transducible transcription factors for nuclear reprogramming. Biotechnology and bioengineering 104, 1047-1058, doi:10.1002/bit.22517 (2009).
7. Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).

8. Takahashi, M. K. et al. Characterizing and prototyping genetic networks with cell-free transcription-translation reactions. Methods 86, 60-72, doi:10.1016/j.ymeth.2015.05.020 (2015).

9. Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).

10. Watanabe, M. et al. Cell-free protein synthesis for structure determination by X-ray crystallography. Methods in molecular biology 607, 149-160, doi:10.1007/978-1-60327-331-2_13 (2010).

11. Martemyanov, K. A., Shirokov, V. A., Kurnasov, O. V., Gudkov, A. T. & Spirin, A. S. Cell-free production of biologically active polypeptides: application to the synthesis of antibacterial peptide cecropin. Protein expression and purification 21, 456-461, doi:10.1006/prep.2001.1400 (2001).

12. Renesto, P. & Raoult, D. From genes to proteins: in vitro expression of rickettsial proteins. Annals of the New York Academy of Sciences 990, 642-652 (2003).

13. Xu, Z., Chen, H., Yin, X., Xu, N. & Cen, P. High-level expression of soluble human beta-defensin-2 fused with green fluorescent protein in *Escherichia coli* cell-free system. Applied biochemistry and biotechnology 127, 53-62 (2005).

14. Sullivan, C. J. et al. A cell-free expression and purification process for rapid production of protein biologics. Biotechnology journal 11, 238-248, doi:10.1002/biot.201500214 (2016).

15. Li, J. et al. Cell-free protein synthesis enables high yielding synthesis of an active multicopper oxidase. Biotechnology journal 11, 212-218, doi:10.1002/biot.201500030 (2016).

16. Heinzelman, P., Schoborg, J. A. & Jewett, M. C. pH responsive granulocyte colony-stimulating factor variants with implications for treating Alzheimer's disease and other central nervous system disorders. Protein engineering, design & selection: PEDS 28, 481-489, doi:10.1093/protein/gzv022 (2015).

17. Shin, J. & Noireaux, V. Efficient cell-free expression with the endogenous *E. Coli* RNA polymerase and sigma factor 70. Journal of biological engineering 4, 8, doi:10.1186/1754-1611-4-8 (2010).

18. Shin, J. & Noireaux, V. An *E. coli* cell-free expression toolbox: application to synthetic gene circuits and artificial cells. ACS synthetic biology 1, 29-41, doi:10.1021/sb200016s (2012).

19. Studier, F. W. & Moffatt, B. A. Use of bacteriophage T7 RNA polymerase to direct selective high-level expression of cloned genes. Journal of molecular biology 189, 113-130 (1986).

20. Kwon, Y. C. & Jewett, M. C. High-throughput preparation methods of crude extract for robust cell-free protein synthesis. Scientific reports 5, 8663, doi:10.1038/srep08663 (2015).

21. Des Soye, B. J., Patel, J. R., Isaacs, F. J. & Jewett, M. C. Repurposing the translation apparatus for synthetic biology. Current opinion in chemical biology 28, 83-90, doi:10.1016/j.cbpa.2015.06.008 (2015).

22. Hong, S. H., Kwon, Y. C. & Jewett, M. C. Non-standard amino acid incorporation into proteins using *Escherichia coli* cell-free protein synthesis. Frontiers in chemistry 2, 34, doi:10.3389/fchem.2014.00034 (2014).

23. Dumas, A. e., Lercher, L., Spicer, C. D. & Davis, B. G. Designing logical codon reassignment—Expanding the chemistry in biology. Chemical *Science* 6, 50-69 (2014).

24. Liu, C. C. & Schultz, P. G. Adding new chemistries to the genetic code. Annual review of biochemistry 79, 413-444, doi:10.1146/annurev.biochem.052308.105824 (2010).

25. Santoro, S. W., Wang, L., Herberich, B., King, D. S. & Schultz, P. G. An efficient system for the evolution of aminoacyl-tRNA synthetase specificity. Nature biotechnology 20, 1044-1048, doi:10.1038/nbt742 (2002).

26. Nehring, S., Budisa, N. & Wiltschi, B. Performance analysis of orthogonal pairs designed for an expanded eukaryotic genetic code. PloS one 7, e31992, doi:10.1371/journal.pone.0031992 (2012).

27. Bundy, B. C. & Swartz, J. R. Site-specific incorporation of p-propargyloxyphenylalanine in a cell-free environment for direct protein-protein click conjugation. Bioconjugate chemistry 21, 255-263, doi:10.1021/bc9002844 (2010).

28. Young, T. S. & Schultz, P. G. Beyond the canonical 20 amino acids: expanding the genetic lexicon. The Journal of biological chemistry 285, 11039-11044, doi:10.1074/jbc.R109.091306 (2010).

29. Hong, S. H. et al. Cell-free protein synthesis from a release factor 1 deficient *Escherichia coli* activates efficient and multiple site-specific nonstandard amino acid incorporation. ACS synthetic biology 3, 398-409, doi:10.1021/sb400140t (2014).

30. Lajoie, M. J. et al. Genomically recoded organisms expand biological functions. *Science* 342, 357-360, doi:10.1126/science.1241459 (2013).

31. Datsenko, K. A. & Wanner, B. L. One-step inactivation of chromosomal genes in *Escherichia coli* K-12 using PCR products. Proceedings of the National Academy of Sciences of the United States of America 97, 6640-6645, doi:10.1073/pnas.120163297 (2000).

32. Mosberg, J. A., Lajoie, M. J. & Church, G. M. Lambda red recombineering in *Escherichia coli* occurs through a fully single-stranded intermediate. Genetics 186, 791-799, doi:10.1534/genetics.110.120782 (2010).

33. Wang, H. H. et al. Programming cells by multiplex genome engineering and accelerated evolution. Nature 460, 894-898, doi:10.1038/nature08187 (2009).

34. Zawada, J. & Swartz, J. Effects of growth rate on cell extract performance in cell-free protein synthesis. Biotechnology and bioengineering 94, 618-624, doi:10.1002/bit.20831 (2006).

35. Bremer, H. & Dennis, P. *Escherichia coli* and *Salmonella*: Cellular and Molecular Biology. 2 edn, Vol. 1 1553-1569 (ASM Press, 1996).

36. Stefano, J. E. & Gralla, J. Lac UV5 transcription in vitro. Rate limitation subsequent to formation of an RNA polymerase-DNA complex. Biochemistry 18, 1063-1067 (1979).

37. de Boer, H. A., Comstock, L. J. & Vasser, M. The tac promoter: a functional hybrid derived from the trp and lac promoters. Proceedings of the National Academy of Sciences of the United States of America 80, 21-25 (1983).

38. Inouye, S. & Inouye, M. Up-promoter mutations in the lpp gene of *Escherichia coli*. Nucleic acids research 13, 3101-3110 (1985).

39. Espah Borujeni, A., Channarasappa, A. S. & Salis, H. M. Translation rate is controlled by coupled trade-offs between site accessibility, selective RNA unfolding and sliding at upstream standby sites. Nucleic acids research 42, 2646-2659, doi:10.1093/nar/gktl 139 (2014).

40. Salis, H. M., Mirsky, E. A. & Voigt, C. A. Automated design of synthetic ribosome binding sites to control protein expression. Nature biotechnology 27, 946-950, doi:10.1038/nbt.1568 (2009).

41. Ellinger, T. & Ehricht, R. Single-step purification of T7 RNA polymerase with a 6-histidine tag. BioTechniques 24, 718-720 (1998).

42. Bryant, J. A., Sellars, L. E., Busby, S. J. & Lee, D. J. Chromosome position effects on gene expression in *Escherichia coli* K-12. Nucleic acids research 42, 11383-11392, doi:10.1093/nar/gku828 (2014).

43. Grodberg, J. & Dunn, J. J. ompT encodes the *Escherichia coli* outer membrane protease that cleaves T7 RNA polymerase during purification. Journal of bacteriology 170, 1245-1253 (1988).

44. Muller, D. K., Martin, C. T. & Coleman, J. E. Processivity of proteolytically modified forms of T7 RNA polymerase. Biochemistry 27, 5763-5771 (1988).

45. Ikeda, R. A. & Richardson, C. C. Enzymatic properties of a proteolytically nicked RNA polymerase of bacteriophage T7. The Journal of biological chemistry 262, 3790-3799 (1987).

46. Ikeda, R. A. & Richardson, C. C. Interactions of a proteolytically nicked RNA polymerase of bacteriophage T7 with its promoter. The Journal of biological chemistry 262, 3800-3808 (1987).

47. Gottesman, S. Proteases and their targets in *Escherichia coli*. Annual review of genetics 30, 465-506, doi:10.1146/annurev.genet.30.1.465 (1996).

48. Hwang, B. Y. et al. Substrate specificity of the *Escherichia coli* outer membrane protease OmpP. Journal of bacteriology 189, 522-530, doi:10.1128/JB.01493-06 (2007).

49. Tunitskaya, V. L. & Kochetkov, S. N. Structural-functional analysis of bacteriophage T7 RNA polymerase. Biochemistry. Biokhimiia 67, 1124-1135 (2002).

50. Petrov, A. S. et al. RNA-magnesium-protein interactions in large ribosomal subunit. The journal of physical chemistry. B 116, 8113-8120, doi:10.1021/jp304723w (2012).

51. Sousa, R. in Encyclopedia of Biological Chemistry Vol. 4 (eds William J. Lennarz & M. Daniel Lane) (Elsevier, 2004).

52. Young, T. S., Ahmad, I., Yin, J. A. & Schultz, P. G. An enhanced system for unnatural amino acid mutagenesis in *E. coli*. Journal of molecular biology 395, 361-374, doi:10.1016/j.jmb.2009.10.030 (2010).

53. Wang, L., Zhang, Z., Brock, A. & Schultz, P. G. Addition of the keto functional group to the genetic code of *Escherichia coli*. Proceedings of the National Academy of Sciences of the United States of America 100, 56-61, doi:10.1073/pnas.0234824100 (2003).

54. Raucher, D. & Ryu, J. S. Cell-penetrating peptides: strategies for anticancer treatment. Trends in molecular medicine 21, 560-570, doi:10.1016/j.molmed.2015.06.005 (2015).

55. Catherine, C. et al. Engineering Thermal Properties of Elastin-like Polypeptides by Incorporation of Unnatural Amino Acids in a Cell-free Protein Synthesis System. Biotechnology and Bioprocess Engineering 20, 417-422, doi:10.1007/s12257-015-0190-1 (2015).

56. Wu, L. L. et al. Multiple site-selective insertions of noncanonical amino acids into sequence-repetitive polypeptides. Chembiochem: a European journal of chemical biology 14, 968-978, doi:10.1002/cbic.201300069 (2013).

57. Chen, Y. J. et al. Characterization of 582 natural and synthetic terminators and quantification of their design constraints. Nature methods 10, 659-664, doi:10.1038/nmeth.2515 (2013).

58. Horton, R. M. PCR-mediated recombination and mutagenesis. SOEing together tailor-made genes. Molecular biotechnology 3, 93-99, doi:10.1007/BF02789105 (1995).

59. Wang, H. H. & Church, G. M. Multiplexed genome engineering and genotyping methods applications for synthetic biology and metabolic engineering. Methods in enzymology 498, 409-426, doi:10.1016/B978-O-12-385120-8.00018-8 (2011).

60. Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).

61. Lederberg, J. & Lederberg, E. M. Replica plating and indirect selection of bacterial mutants. Journal of bacteriology 63, 399-406 (1952).

62. Davanloo, P., Rosenberg, A. H., Dunn, J. J. & Studier, F. W. Cloning and expression of the gene for bacteriophage T7 RNA polymerase. Proceedings of the National Academy of Sciences of the United States of America 81, 2035-2039 (1984).

63. Fritz, B. R., Jamil, O. K. & Jewett, M. C. Implications of macromolecular crowding and reducing conditions for in vitro ribosome construction. Nucleic acids research 43, 4774-4784, doi:10.1093/nar/gkv329 (2015).

64. Guarino, C. and M. P. DeLisa, A prokaryote-based cell-free translation system that efficiently synthesizes glycoproteins. Glycobiology, 2012. 22(5): p. 596-601.

65. Maue, A. C., F. Poly, and P. Guerry, A capsule conjugate vaccine approach to prevent diarrheal disease caused by *Campylobacter jejuni*. Hum Vaccin Immunother, 2014. 10(6): p. 1499-504.

66. Feldman, M. F., et al., Engineering N-linked protein glycosylation with diverse O antigen lipopolysaccharide structures in *Escherichia coli*. Proc Natl Acad Sci USA, 2005. 102(8): p. 3016-21.

67. Szymanski, C. M., et al., Evidence for a system of general protein glycosylation in *Campylobacter jejuni*. Mol Microbiol, 1999. 32(5): p. 1022-30.

68. Linton, D., et al., Identification of N-acetylgalactosamine-containing glycoproteins PEB3 and CgpA in *Campylobacter jejuni*. Mol Microbiol, 2002. 43(2): p. 497-508.

69. Spiro, R. G., Protein glycosylation: nature, distribution, enzymatic formation, and disease implications of glycopeptide bonds. Glycobiology, 2002. 12(4): p. 43R-56R.

70. Lame, R. A., The Information-Storing Potential of the Sugar Code. Glycosciences: Status and Perspectives, 1997: p. 1-14.

71. Raman, R., et al., Glycomics: an integrated systems approach to structure-function relationships of glycans. Nat Methods, 2005. 2(11): p. 817-24.

72. Ohtsubo, K. and J. D. Marth, Glycosylation in cellular mechanisms of health and disease. Cell, 2006. 126(5): p. 855-67.

73. Wang, L. X. and B. G. Davis, Realizing the Promise of Chemical Glycobiology. Chem Sci, 2013. 4(9): p. 3381-3394.

74. Chauhan, J. S., A. Rao, and G. P. Raghava, In silico platform for prediction of N-, O- and C-glycosites in eukaryotic protein sequences. PLoS One, 2013. 8(6): p. e67008.

75. Gavel, Y. and G. von Heijne, Sequence differences between glycosylated and non-glycosylated Asn-X-Thr/Ser acceptor sites: implications for protein engineering. Protein Eng, 1990. 3(5): p. 433-42.

76. Walt, D., et al., Transforming Glycoscience: A Roadmap for the Future. 2012: The National Academies Press.

77. Weerapana, E. and B. Imperiali, Asparagine-linked protein glycosylation: from eukaryotic to prokaryotic systems. Glycobiology, 2006. 16(6): p. 91R-101R.

78. Wacker, M., et al., N-linked glycosylation in *Campylobacter jejuni* and its functional transfer into *E. coli*. Science, 2002. 298(5599): p. 1790-3.

79. Glover, K. J., et al., Direct biochemical evidence for the utilization of UDP-bacillosamine by PglC, an essential glycosyl-1-phosphate transferase in the *Campylobacter jejuni* N-linked glycosylation pathway. Biochemistry, 2006. 45(16): p. 5343-50.

80. Glover, K. J., E. Weerapana, and B. Imperiali, In vitro assembly of the undecaprenylpyrophosphate-linked heptasaccharide for prokaryotic N-linked glycosylation. Proc Natl Acad Sci USA, 2005. 102(40): p. 14255-9.

81. Olivier, N. B., et al., In vitro biosynthesis of UDP-N, N'-diacetylbacillosamine by enzymes of the *Campylobacter jejuni* general protein glycosylation system. Biochemistry, 2006. 45(45): p. 13659-69.

82. Carlson, E. D., et al., Cell-free protein synthesis: applications come of age. Biotechnol Adv, 2012. 30(5): p. 1185-94.

83. Hodgman, C. E. and M. C. Jewett, Cell-free synthetic biology: thinking outside the cell. Metab Eng, 2012. 14(3): p. 261-9.

84. Caschera, F. and V. Noireaux, Synthesis of 2.3 mg/ml of protein with an all *Escherichia coli* cell-free transcription-translation system. Biochimie, 2014. 99: p. 162-8.

85. Calhoun, K. A. and J. R. Swartz, An economical method for cell-free protein synthesis using glucose and nucleoside monophosphates. Biotechnol Prog, 2005. 21(4): p. 1146-53.

86. Calhoun, K. A. and J. R. Swartz, Energizing cell-free protein synthesis with glucose metabolism. Biotechnol Bioeng, 2005. 90(5): p. 606-13.

87. Lian, Q., H. Cao, and F. Wang, The cost-efficiency realization in the *Escherichia coli*-based cell-free protein synthesis systems. Appl Biochem Biotechnol, 2014. 174 (7): p. 2351-67.

88. Ollis, A. A., et al., Engineered oligosaccharyltransferases with greatly relaxed acceptor-site specificity. Nat Chem Biol, 2014. 10(10): p. 816-22.

PATENT DOCUMENTS

U.S. Pat. Nos.: U.S. Pat. Nos. 5,478,730; 5,556,769; 5,665,563; 6,168,931; 6,518,058; 6,783,957; 6,869,774; 6,994,986; 7,118,883; 7,189,528; 7,338,789; 7,387,884; 7,399,610; 8,357,529; 8,574,880; 8,703,471; 8,999,668; and 9,410,170; the contents of which are incorporated herein by reference in their entirety.

U.S. Patent Publications: US20040209321; US20050170452; US20060211085; US20060234345; US20060252672; US20060257399; US20060286637; US20070026485; US20070154983; US20070178551; US20080138857; US20140295492; US20160060301; US20180016612; and US20180016614; the contents of which are incorporated herein by reference in their entirety.

Published International Applications: WO2003056914A1; WO2004013151A2; WO2004035605A2; WO2006102652A2; WO2006119987A2; WO2007120932A2; WO2014144583; and WO2017117539; the contents of which are incorporated herein by reference in their entirety.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A cell-free glycoprotein synthesis (CFGpS) platform, wherein components of the platform are combined in a single reaction vessel, the platform comprising:

(1) a cell lysate from a genomically recoded strain of *Escherichia coli* (*E. coli*) comprising:

(a) a mutation in an endogenous peptide chain release factor RF1 (prfA) gene resulting in a deficiency of the encoded release factor 1 protein;

(b) a mutation in an endogenous DNA-specific endonuclease I (endA) gene encoding a DNA-specific endonuclease I protein resulting in a deficiency of the endonuclease I protein;

(c) an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO);

(2) a DNA template for expressing a sequence-defined amino acid polymer, a DNA-dependent RNA polymerase for transcribing an mRNA encoding the sequence-defined amino acid polymer, nucleotide triphosphates, amino acids, and an energy source; and (3) a non-standard amino acid (nsAA), an orthogonal amino-acyl tRNA synthetase (aaRS), or both of an nsAA and an aaRS, wherein the non-standard amino acid (nsAA) comprises a moiety that reacts with a corresponding moiety on a saccharide to conjugate the nsAA to the saccharide; and (4) one or more components for performing a strain-promoted alkyne-azide cycloaddition (SPAAC) reaction.

2. The platform of claim 1, wherein the strain is derived from *Escherichia coli* strain rEc.C321.

3. The platform of claim 1, wherein the strain further comprises a mutation in a glutathione reductase (gor) gene encoding a glutathione reductase protein, resulting in a knock-out of the encoded glutathione reductase protein.

4. The platform of claim 1, wherein the strain comprises an episomal or genomic vector for expressing an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO).

5. The platform of claim 1, wherein the nsAA is selected from para-azidophenylalanine (pAzF) and para-propargly-oxy-phenylalanine (pAcF).

6. The platform of claim 5, wherein the one or more components for performing the strain-promoted alkyne-azide cycloaddition (SPAAC) reaction comprise a dibenzocyclooctyne (DBCO) moiety.

7. A method for preparing a sequence defined amino acid polymer comprising:

reacting the components of the platform of claim 1 to prepare the sequence defined amino acid polymer.

8. A cell-free glycoprotein synthesis (CFGpS) platform, wherein the components of the platform are combined in a single reaction vessel, the platform comprising:

(1) a cell lysate from a genomically recoded strain of *Escherichia coli* (*E. coli*) comprising:

(a) a mutation in an endogenous peptide chain release factor RF1 (prfA) gene resulting in a deficiency of the encoded release factor 1 protein;

(b) a mutation in an endogenous DNA-specific endonuclease I (endA) gene encoding a DNA-specific endonuclease I protein resulting in a deficiency of the endonuclease I protein;

(c) a mutation in an endogenous guanosine diphosphate (GDP)-mannose 4,6-dehydratase (gmd) gene encoding a GDP-mannose 4,6-dehydratase protein resulting in reduced expression and/or activity of GDP-mannose 4,6-dehydratase as compared to wild-type *E. coli*; and (d) an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO);

(2) a DNA template for expressing a sequence-defined amino acid polymer, a DNA-dependent RNA polymerase for transcribing an mRNA encoding the sequence-defined amino acid polymer, nucleotide triphosphates, amino acids, and an energy source; and (3) a non-standard amino acid (nsAA), an orthogonal amino-acyl tRNA synthetase (aaRS), or both of an nsAA and an aaRS, wherein the non-standard amino acid (nsAA) comprises a moiety that reacts with a corresponding moiety on a saccharide to conjugate the nsAA to the saccharide; and (4) one or more components for performing a strain-promoted alkyne-azide cycloaddition (SPAAC) reaction.

9. The platform of claim 8, wherein the strain is derived from *Escherichia coli* strain rEc.C321.

10. The platform of claim 8, wherein the strain further comprises a mutation in a glutathione reductase (gor) gene encoding a glutathione reductase protein, resulting in a knock-out of the encoded glutathione reductase protein.

11. The platform of claim 8, wherein the strain comprises an episomal or genomic vector for expressing an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO).

12. The platform of claim 8, wherein the nsAA is selected from para-azidophenylalanine (pAzF) and para-propargly-oxy-phenylalanine (pAcF).

13. The platform of claim 12, wherein the one or more components for performing the strain-promoted alkyne-azide cycloaddition (SPAAC) reaction comprise a dibenzocyclooctyne (DBCO) moiety.

14. A method for preparing a sequence defined amino acid polymer comprising:

reacting the components of the platform of claim 8 to prepare the sequence defined amino acid polymer.

15. A cell-free glycoprotein synthesis (CFGpS) platform, wherein the components of the platform are combined in a single reaction vessel, the platform comprising:

(1) a cell lysate from a genomically recoded strain of *Escherichia coli* (*E. coli*) comprising:

(a) a mutation in an endogenous peptide chain release factor RF1 (prfA) gene resulting in a deficiency of the encoded release factor 1 protein;

(b) a mutation in an endogenous O-antigen ligase (waaL) gene encoding an O-antigen ligase protein resulting in a deficiency of the O-antigen ligase protein;

(c) a mutation in an endogenous DNA-specific endonuclease I (endA) gene encoding a DNA-specific endonuclease I protein resulting in a deficiency of the endonuclease I protein;

(d) an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO).

16. The platform of claim 15, wherein the strain further comprises a mutation in a glutathione reductase (gor) gene encoding a glutathione reductase protein, resulting in a knock-out of the encoded glutathione reductase protein.

17. The platform of claim 15, wherein the strain comprises an episomal or genomic vector for expressing an orthogonal oligosaccharide transferase (OST), an orthogonal ligase for synthesizing lipid-linked oligosaccharides (LLO), or both of an orthogonal oligosaccharide transferase (OST) and an orthogonal ligase for synthesizing lipid-linked oligosaccharides (LLO).

18. The platform of claim 15, wherein the nsAA is selected from para-azidophenylalanine (pAzF) and para-proparglyoxy-phenylalanine (pAcF).

19. The platform of claim 18, wherein the one or more components for performing the strain-promoted alkyne-azide cycloaddition (SPAAC) reaction comprise a dibenzo-cyclooctyne (DBCO) moiety.

20. A method for preparing a sequence defined amino acid polymer comprising:

reacting the components of the platform of claim 15 to prepare the sequence defined amino acid polymer.

*     *     *     *     *

SEQUENCE LISTING

```
Sequence total quantity: 9
SEQ ID NO: 1            moltype = AA  length = 883
FEATURE                 Location/Qualifiers
source                  1..883
                        mol_type = protein
                        organism = Teseptimavirus T7
SEQUENCE: 1
MNTINIAKND FSDIELAAIP FNTLADHYGE RLAREQLALE HESYEMGEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
```

```
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 2              moltype = DNA   length = 2877
FEATURE                  Location/Qualifiers
source                   1..2877
                         mol_type = genomic DNA
                         organism = Teseptimavirus T7
SEQUENCE: 2
tcgcgctgca ctggcgtaat gctgaccgga tggctatcgc taatggtctt acgctcaaca   60
ttgataagca acttgacgca atgttaatgg gctgatagtc ttatcttaca ggtcatctgc   120
gggtggcctg aataggtacg atttactaac tggaagaggc actaaatgaa cacgattaac   180
atcgctaaga acgacttctc tgacatcgaa ctggctgcta tcccgttcaa cactctggct   240
gaccattacg gtgagcgttt agctcgcgaa cagttggccc ttgagcatga gtcttacgag   300
atgggtgaag cacgcttccg caagatgttt gagcgtcaac ttaaagctgg tgaggttgcg   360
gataacgctg ccgccaagcc tctcatcact accctactcc ctaagatgat tgcacgcatc   420
aacgactggt ttgaggaagt gaaagctaag cgcggcaagc gcccgacagc cttccagttc   480
ctgcaagaaa tcaagccgga agccgtagcg tacatcacca ttaagaccac tctggcttgc   540
ctaaccagtg ctgacaatac aaccgttcag gctgtagcaa gcgcaatcgg tcgggccatt   600
gaggacgagg ctcgcttcgg tcgtatccgt gaccttgaag ctaagcactt caagaaaaac   660
gttgaggaac aactcaacaa gcgcgtaggg cacgtctaca agaaagcatt tatgcaagtt   720
gtcgaggctg acatgctctc taagggtcta ctcggtggcg aggcgtggtc ttcgtggcat   780
aaggaagact ctattcatgt aggagtacgc tgcatcgaga tgctcattga gtcaaccgga   840
atggttagct tacaccgcca aaatgctggc gtagtaggtc aagactctga gactatcgaa   900
ctcgcacctg aatacgctgg ggctatcgca acccgtcag gtgcgctggc tggcatctct   960
ccgatgttcc aaccttgcgt agttcctcct aagccgtgga ctggcattac tggtggtggc   1020
tattgggcta acggtcgtcg tcctctggcg ctggtgcgta ctcacagtaa gaaagcactg   1080
atgcgctacg aagacgttta catgcctgag gtgtacaaag cgattaacat tgcgcaaaac   1140
accgcatgga aatcaacaa gaaagtccta gcggtcgcca acgtaatcac caagtggaaa   1200
cattgtccgg tcgaggacat ccctgcgatt gagcgtgaag aactcccgat gaaaccggaa   1260
gacatcgaca tgaatcctga ggctctcacc gcgtggaaac gtgctgccgc tgctgtgtac   1320
cgcaaggaca gggctcgcaa gtctcgccgt atcagccttg agttcatgct tgagcaagcc   1380
aataagtttg ctaaccataa ggccatctgg ttcccttaca aatggactg gcgcggtcgt   1440
gtttacgccg tgtcaatgtt caacccgcaa ggtaacgata tgaccaaagg actgcttacg   1500
ctggcgaaag gtaaaccaat cggtaaggaa ggttactact ggctgaaaat ccacggtgca   1560
aactgtgcgg gtgtcgataa ggttccgttc cctgagcgca tcaagttcat tgaggaaaac   1620
cacgagaaca tcatggcttg cgctaagtct ccactggaga cacttggtg ggctgagcaa   1680
gattctccgt tctgcttcct tgcgttctgc tttgagtacg ctggggtaca gcaccacggc   1740
ctgagctata actgctccct tccgctggcg tttgacgggg cttgctctgg catccagcac   1800
ttctccgcga tgctccgaga tgaggtaggt ggtcgcgcgg ttaacttgct tcctagtgag   1860
accgttcagg acatctacgg gattgttgct aagaaagtca acgagattct acaagcagac   1920
gcaatcaatg ggaccgataa cgaagtagtt accgtgacca gtagaacac tggtgaaatc   1980
tctgagaaag tcaagctggg cactaaggca ctggctggtc aatggctggc tcacggtgtt   2040
actcgcagtg tgactaagcg ttcagtcatg acgctggctt acgggtccaa agagttcggc   2100
ttccgtcaac aagtgctgga agataccatt cagccgcta ttgattccgg caagggtccg   2160
atgttcactc agccgaatca ggctgctgga tacatgccta agctgatttg ggaatctgtg   2220
agcgtgacgg tggtagctgc ggttgaagca atgaactggc ttaagtctgc tgctaagctg   2280
ctggctgctg aggtcaaaga taagaagact ggagagattc ttcgcaagcg ttgcgctgtg   2340
cattgggtaa ctcctgatgg tttccctgtg tggcaggaat acaagaagcc tattcagacg   2400
cgcttgaacc tgatgttcct cggtcagttc cgcttacagc ctacaattaa caccaacaaa   2460
gatagcgaga ttgatgcaca caaacaggag tctggtatcg ctcctaactt gtacacagc   2520
caagacggta gccaccttcg taagactgta gtgtgggcac acgagaagta cggaatcgaa   2580
tcttttgcac tgattcacga ctccttcggt accattccgg ctgacgctgc gaacctgttc   2640
aaagcagtgc gcgaaactat ggttgacaca tatgagtctt gtgatgtact ggctgatttc   2700
tacgaccagt tcgctgacca gttgcacgag tctcaattgg acaaaatgcc agcacttccg   2760
gctaaaggta acttgaacct ccgtgacatc ttagagtcgg acttcgcgtt cgcgtaacgc   2820
caaatcaata cgactcacta tagagggaca aactcaaggt cattcgcaag agtggcc     2877

SEQ ID NO: 3              moltype = DNA   length = 18
FEATURE                  Location/Qualifiers
source                   1..18
                         mol_type = genomic DNA
                         organism = Teseptimavirus T7
SEQUENCE: 3
taatacgact cactatag                                                18

SEQ ID NO: 4              moltype = AA   length = 884
FEATURE                  Location/Qualifiers
source                   1..884
                         mol_type = protein
                         organism = Teetrevirus T3
SEQUENCE: 4
MNIIENIEKN DFSEIELAAI PFNTLADHYG SALAKEQLAL EHESYELGER RFLKMLERQA   60
KAGEIADNAA AKPLLATLLP KLTTRIVEWL EEYASKKGRK PSAYAPLQLL KPEASAFITL   120
KVILASLTST NMTTIQAAAG MLGKAIEDEA RFGIRDLEA KHFKKHVEEQ LNKRHGQVYK   180
KAFMQVVEAD MIGRGLLGGE AWSSWDKETT MHVGIRLIEM LIESTGLVEL QRHNAGNAGS   240
DHEALQLAQE YVDVLAKRAG ALAGISPMFQ PCVVPPKPWV AITGGGYWAN GRRPLALVRT   300
HSKKGLMRYE DVYMPEVYKA VNLAQNTAWK INKKVLAVVN EIVNWKNCPV ADIPSLERQE   360
```

-continued

```
LPPKPDDIDT NEAALKEWKK AAAGIYRLDK ARVSRRISLE FMLEQANKFA SKKAIWFPYN  420
MDWRGRVYAV PMFNPQGNDM TKGLLTLAKG KPIGEEGFYW LKIHGANCAG VDKVPFPERI  480
AFIEKHVDDI LACAKDPINN TWWAEQDSPF CFLAFCFEYA GVTHHGLSYN CSLPLAFDGS  540
CSGIQHFSAM LRDEVGGRAV NLLPSETVQD IYGIVAQKVN EILKQDAING TPNEMITVTD  600
KDTGEISEKL KLGTSTLAQQ WLAYGVTRSV TKRSVMTLAY GSKEFGFRQQ VLDDTIQPAI  660
DSGKGLMFTQ PNQAAGYMAK LIWDAVSVTV VAAVEAMNWL KSAAKLLAAE VKDKKTKEIL  720
RHRCAVHWTT PDGFPVWQEY RKPLQKRLDM IFLGQFRLQP TINTLKDSGI DAHKQESGIA  780
PNFVHSQDGS HLRMTVVYAH EKYGIESFAL IHDSFGTIPA DAGKLFKAVR ETMVITYENN  840
DVLADFYSQF ADQLHETQLD KMPPLPKKGN LNLQDILKSD FAFA                   884
```

```
SEQ ID NO: 5              moltype = DNA   length = 2896
FEATURE                   Location/Qualifiers
source                    1..2896
                          mol_type = genomic DNA
                          organism = Teetrevirus T3
SEQUENCE: 5
gatgaggtgc gcattgtggg gcaaaccgtt acacatagac gcataccttg acaagcgtct   60
acaaggctga tagagtcttt tcttacaggt catcatgagg tggcctgaat aggaacgatt  120
tattcacaat gaggtaagca atgaacatca tcgaaaacat cgaaaagaat gacttctcag  180
aaatcgaact ggctgctatc ccgttcaaca cactggctga ccactacgga agcgccttgg  240
ctaaagagca gttggctta gaacatgagt cttatgagct aggcgagcgc cgcttcctca  300
agatgcttga gcgtcaagcg aaagctggtg agattgcaga caacgcagcc gctaagccgt  360
tactcgctac gcttctccct aagttaacca cacgtatcgt cgagtggctc gaagagtacg  420
catcgaagaa aggccgcaag cctagcgcat acgcaccgct ccagttactc aagcggagg   480
cctccgcgtt tatcaccctg aaagttatcc ttgcgtcact aaccagtacg aacatgacaa  540
ccattcaggc cgctgctggt atgctgggga aagccattga ggacgaggca cgatttgggc  600
gcatccgtga cctagaagcg aagcacttca agaagcacgt tgaggaacag cttaacaagc  660
gccacgggca agtctacaag aaaagcattta tgcaggtggt cgaggccgat atgattggtc  720
gaggtctgct tggtggcgag gcgtggtcta gctgggataa agaaaccacg atgcacgtag  780
ggattcgcct gattgaaatg ctgattgaat ccacgggtct ggtggaatta cagcgccaca  840
acgcaggtaa cgcaggctct gaccatgagg cactgcaact ggcccaagag tacgtggacg  900
tattagcgaa gcgtgcaggc gctctggcgg gtatctctcc gatgttccag ccgtgtgtcg  960
taccgccgaa accttgggta gcaatcacag ggggcggcta ttgggctaac ggtcgcagac 1020
ctttggcact cgttcgcact cactctaaga agggcttgat gcgctacgaa gacgtttaca 1080
tgccagaagt ctacaaggct gtgaacctcg cgcaaaacac cgcatggaaa atcaacaaga 1140
aagttcttgc tgttgtcaat gagattgtta actggaagaa ttgcccggta gcagacattc 1200
catcgctgga gcgccaagag ttaccgccta agcctgacga cattgacacc aacgaggcag 1260
cgctcaagga gtggaagaaa gccgctgctg gtatctatcg cttggacaag gcacgagtgt 1320
ctcgccgtat cagcttagag ttcatgctgg agcaggccaa caagttcgca agtaagaaag 1380
caatctggtt cccttacaac atggactggc gcggtcgtgt gtacgctgtg ccgatgttca 1440
acccgcaagg caacgacatg acgaaaggtc tgctgaccct tgctaaaggc aagccaatcg 1500
gtgaggaagg tttctactgg ctgaaaatcc acggtgcgaa ctgtgcgggt gttgataagg 1560
ttccattccc ggagcgcatc gcgttcattg agaagcacgt agacgacatt ctggcttgcg 1620
ctaaagaccc aatcaataac acttggtggg ctgagcagga ttcaccgttc tgtttcctcg 1680
cgttttgctt cgagtatgca ggcgttacgc accacggtct gagctacaat tgctctctgc 1740
cgctggcgtt cgacgggtct tgctctggta tccagcactt ctccgcgatg ctccgcgatg 1800
aggtaggcgg tcgtgcggtt aacctgctgc caagcgaaac cgtgcaggac atttacggca 1860
tcgttgcaca gaaagtaaac gagattctca aacaggatgc aatcaacggc acgcctaacg 1920
agatgattac cgtgaccgac aaggacaccg gggaaatctc agagaagctc aaacttggaa 1980
cctcaacgct ggcgcaacag tggctggcat atggtgtaac ccgtagcgta actaaacgtt 2040
cggtcatgac gctggcttac ggttccaagg agttcggcttc tcgtcaacag gtattggata 2100
acaccattca gcctgcaatt gacagcggta agggcttgat gttcacccaa ccgaaccaag 2160
cggctggcta tatggctaag ctgatttggg atgcgggtaag cgtgaccgta gttgcagcgg 2220
ttgaggcgat gaactggctc aaatctgccg ctaagctgct ggctgctgag gtcaaggaca 2280
agaagaccaa ggagattctg cgccaccgtt gcgcggttca ctggactacg ccggacggct 2340
tcccggtctg gcaggaatac cgcaagccac tccagaagcg tctcgatatg attttcttag 2400
ggcaattccg tctgcaaccg acgattaata ccctcaagga ttcaggcatt gacgcacaca 2460
agcaggagtc tggcatcgct cctaactttg ttcactcaca ggacggtagc cacctccgca 2520
tgacgtcgt ttatgctcac gagaagtatg gcattgagtc ctttgcgctc atccatgaca 2580
gctttgggac tatcccggca gacgctggta agctctttaa ggctgtgcgt gaaacgatgg 2640
ttatcacgta tgagaacaac gatgtgctgg cagacttcta ctctcagttt gccgaccagc 2700
tacacgagac ccaactggac aagatgcctc cgcttccgaa gaaaggaaac ctgaacctgc 2760
aagacatttct caagtctgac tttgcctttg cataacaagc acttagcatt aaccctcact 2820
aacgggagac tacttaaggt ctcccactt aagacactta aggtactaag agattaaatt 2880
tatgattaac attaag                                                 2896
```

```
SEQ ID NO: 6              moltype = DNA   length = 18
FEATURE                   Location/Qualifiers
source                    1..18
                          mol_type = genomic DNA
                          organism = Teetrevirus T3
SEQUENCE: 6
aattaaccct cactaaag                                                 18
```

```
SEQ ID NO: 7              moltype = AA   length = 874
FEATURE                   Location/Qualifiers
source                    1..874
                          mol_type = protein
                          organism = Zindervirus SP6
```

-continued

```
SEQUENCE: 7
MQDLHAIQLQ LEEEMFNGGI RRFEADQQRQ IAAGSESDTA WNRRLLSELI APMAEGIQAY  60
KEEYEGKKGR APRALAFLQC VENEVAAYIT MKVVMDMLNT DATLQAIAMS VAERIEDQVR  120
FSKLEGHAAK YFEKVKKSLK ASRTKSYRHA HNVAVVAEKS VAEKDADFDR WEAWPKETQL  180
QIGTTLLEIL EGSVFYNGEP VFMRAMRTYG GKTIYYLQTS ESVGQWISAF KEHVAQLSPA  240
YAPCVIPPRP WRTPFNGGFH TEKVASRIRL VKGNREHVRK LTQKQMPKVY KAINALQNTQ  300
WQINKDVLAV IEEVIRLDLG YGVPSFKPLI DKENKPANPV PVEFQHLRGR ELKEMLSPEQ  360
WQQFINWKGE CARLYTAETK RGSKSAAVVR MVGQARKYSA FESIYFVYAM DSRSRVYVQS  420
STLSPQSNDL GKALLRFTEG RPVNGVEALK WFCINGANLW GWDKKTFDVR VSNVLDEEFQ  480
DMCRDIAADP LTFTQWAKAD APYEFLAWCF EYAQYLDLVD EGRADEFRTH LPVHQDGSCS  540
GIQHYSAMLR DEVGAKAVNL KPSDAPQDIY GAVAQVVIKK NALYMDADDA TTFTSGSVTL  600
SGTELRAMAS AWDSIGITRS LTKKPVMTLP YGSTRLTCRE SVIDYIVDLE EKEAQKAVAE  660
GRTANKVHPF EDDRQDYLTP GAAYNYMTAL IWPSISEVVK APIVAMKMIR QLARFAAKRN  720
EGLMYTLPTG FILEQKIMAT EMLRVRTCLM GDIKMSLQVE TDIVDEAAMM GAAAPNFVHG  780
HDASHLILTV CELVDKGVTS IAVIHDSFGT HADNTLTLRV ALKGQMVAMY IDGNALQKLL  840
EEHEERWMVD TGIEVPEQGE FDLNEIMDSE YVFA  874

SEQ ID NO: 8        moltype = DNA  length = 2630
FEATURE             Location/Qualifiers
source              1..2630
                    mol_type = genomic DNA
                    organism = Zindervirus SP6
SEQUENCE: 8
gatgcaagat ttacacgcta tccagcttca attagaagaa gagatgttta atggtggcat  60
tcgtcgcttc gaagcagatc aacaacgcca gattgcagca ggtagcgaga gcgacacagc  120
atggaaccgc cgcctgttgt cagaacttat tgcacctatg gctgaaggca ttcaggctta  180
taaagaagag tacgaaggta agaaaggtcg tgcacctcgc gcattggctt tcttacaatg  240
tgtagaaaat gaagttgcag catacatcac tatgaaagtt gttatggata tgctgaatac  300
ggatgctacc cttcaggcta ttgcaatgag tgtagcagaa cgcattgaag accaagtgcg  360
cttttctaag ctagaaggtc acgccgctaa atactttgag aaggttaaga agtcactcaa  420
ggctagccgt actaagtcat atcgtcacgc tcataacgta gctgtagttg ctgaaaaatc  480
agttgcagaa aaggacgcgg actttgaccg ttgggaggcg tggccaaaag aaactcaatt  540
gcagattggt actaccttgc ttgaaatctt agaaggtagc gttttctata tggtgaacc  600
tgtatttatg cgtgctatgc gcacttatgg cggaaagact atttactact tacaaacttc  660
tgaaagtgta ggccagtgga ttagcgcatt caaagagcac gtagcgcaat taagcccagc  720
ttatgcccct tgcgtaatcc ctcctcgtcc ttggagaact ccatttaatg gagggttcca  780
tactgagaag gtagctagcc gtatccgtct tgtaaaaggt aaccgtgagc atgtacgcaa  840
gttgactcaa aagcaaatgc caaaggttta taaggctatc aacgcattac aaaatacaca  900
atggcaaatc aacaaggatg tattagcagt tattgaagaa gtaatccgct tagaccttgg  960
ttatggtgta ccttccttca agccactgat tgacaaggag aacaagccag ctaacccggt  1020
acctgttgaa ttccaacacc tgcgcggtcg tgaactgaaa gagatgctat cacctgagca  1080
gtggcaacaa ttcattaact ggaaaggcga atgcgcgcgc ctatataccg cagaaactaa  1140
gcgcggttca aagtccgccg ccgttgttcg catggtagga caggcccgta aatatagcgc  1200
ctttgaatcc atttacttcg tgtacgcaat ggatagccgc agccgtgtct atgtgcaatc  1260
tagcacgctc tctccgcagt ctaacgactt aggtaaggca ttactccgct ttaccgaggg  1320
acgccctgtg aatggcgtag aagcgcttaa atggttctgc atcaatggtg ctaacctttg  1380
gggatgggac aagaaaactt ttgatgtgcg cgtgtctaac gtattagatg aggaattcca  1440
agatatgtgt cgagacatcg ccgcagaccc tctcacattc acccaatggg ctaaagctga  1500
tgcaccttat gaattcctcg cttggtgctt tgagtatgct caataccttg atttggtgga  1560
tgaaggaagg gccgacgaat ccgcactca cctaccagta catcaggacg ggtcttgttc  1620
aggcattcag cactatagtg ctatgcttcg cgacgaagta ggggccaaag tgttaacct  1680
gaaaccctcc gatgcaccgc aggatatcta tggggcggtg gcgcaagtgg ttatcaagaa  1740
gaatgcgcta tatatggatg cggacgatgc aaccacgttt acttctggta gcgtcacgct  1800
gtccggtaca gaactgcgag caatggctag cgcatgggat agtattggta ttacccgtag  1860
cttaaccaaa aagcccgtga tgaccttgcc atatggttct actcgcttaa cttgccgtga  1920
atctgtgatt gattacatcg tagacttaga ggaaaaagag gcgcagaagg cagtagcaga  1980
agggcggacg gcaaacaagg tacatccttt tgaagacgat cgtcaagatt acttgactcc  2040
gggcgcagct tacaactaca tgacggcact aatctggcct tctatttctg aagtagttaa  2100
ggcaccgata gtagctatga agatgatacg ccagcttgca cgctttgcag cgaaacgtaa  2160
tgaaggcctg atgtacaccc tgcctactgg cttcatctta gaacagaaga tcatggcaac  2220
cgagatgcta cgcgtgcgta cctgtctgat gggtgatatc aagatgtccc ttcaggttga  2280
aacggatatc gtagatgaag ccgctatgat gggagcagca gcacctaatt tcgtacacgg  2340
tcatgacgca agtcacctta tccttaccgt atgtgaattg gtagacaagg gcgtaactag  2400
tatcgctgta atccacgact cttttggtac tcatgcagat aacaccctca ctcttagagt  2460
ggcacttaaa gggcagatgg ttgcaatgta tattgatggt aatgcgcttc agaaactact  2520
ggaggagcat gaagagcgct ggatggttga tacaggtatc gaagtacctg agcaagggga  2580
gttcgacctt aacgaaatca tggattctga atacgtattt gcctaataga  2630

SEQ ID NO: 9        moltype = DNA  length = 16
FEATURE             Location/Qualifiers
source              1..16
                    mol_type = genomic DNA
                    organism = Zindervirus SP6
SEQUENCE: 9
taatccactg tgatat  16
```